(12) United States Patent
Holland et al.

(10) Patent No.: US 12,178,896 B2
(45) Date of Patent: Dec. 31, 2024

(54) FRAGRANCE COMPOSITIONS AND USES THEREOF

(71) Applicant: Coty Inc., New York, NY (US)

(72) Inventors: Lynette Anne Makins Holland, Abbots Langley (GB); Neil Dring, Buckinghamshire (GB)

(73) Assignee: Coty Inc., New York, NY (US)

( * ) Notice: Subject to any disclaimer, the term of this patent is extended or adjusted under 35 U.S.C. 154(b) by 0 days.

(21) Appl. No.: 16/967,920

(22) PCT Filed: Jul. 25, 2018

(86) PCT No.: PCT/US2018/043721
§ 371 (c)(1),
(2) Date: Aug. 6, 2020

(87) PCT Pub. No.: WO2019/156708
PCT Pub. Date: Aug. 15, 2019

(65) Prior Publication Data
US 2021/0361547 A1    Nov. 25, 2021

Related U.S. Application Data

(60) Provisional application No. 62/627,437, filed on Feb. 7, 2018.

(51) Int. Cl.
*A61K 8/34* (2006.01)
*A61K 8/35* (2006.01)
(Continued)

(52) U.S. Cl.
CPC ............... *A61K 8/342* (2013.01); *A61K 8/35* (2013.01); *A61K 8/37* (2013.01); *A61K 8/735* (2013.01); *A61K 8/86* (2013.01); *A61Q 13/00* (2013.01)

(58) Field of Classification Search
CPC . A61K 8/86; A61K 8/35; A61K 8/735; A61K 8/342; A61K 8/37; A61Q 13/00
See application file for complete search history.

(56) References Cited

U.S. PATENT DOCUMENTS

| 4,324,703 A | 4/1982 | Seldner |
| 9,814,661 B2 | 11/2017 | Bonnet et al. |

(Continued)

FOREIGN PATENT DOCUMENTS

| CN | 102933193 A | 2/2013 |
| CN | 106061459 A | 10/2016 |

(Continued)

OTHER PUBLICATIONS

"International Application Serial No. PCT/US2018/043700, International Search Report mailed Oct. 26, 2018", 9 pgs.

(Continued)

*Primary Examiner* — Jianfeng Song
(74) *Attorney, Agent, or Firm* — Schwegman Lundberg & Woessner, P.A.

(57) ABSTRACT

According to various embodiments, a composition includes a fragrance component present in an amount of from about 0.04 wt % to about 30 wt %, relative to the total weight of the composition. The fragrance component includes at least one low volatile fragrance material present in an amount greater than 30 wt %, relative to the total weight of the fragrance component. This can be defined as a bottom-heavy fragrance. The fragrance component further includes at least one moderate volatile fragrance material present in an amount of from about 30 wt % to about 70 wt %, relative to the total weight of the fragrance component. The fragrance component further includes at least one high volatile fra- (Continued)

grance material present in an amount of from about 0.1 wt % to about 30 wt % relative to the total weight of the fragrance component.

6 Claims, 10 Drawing Sheets

(51) Int. Cl.
    *A61K 8/37*     (2006.01)
    *A61K 8/73*     (2006.01)
    *A61K 8/86*     (2006.01)
    *A61Q 13/00*     (2006.01)

(56) References Cited

U.S. PATENT DOCUMENTS

| | | |
|---|---|---|
| 10,138,441 B2 | 11/2018 | Holland et al. |
| 10,336,966 B2 | 7/2019 | Holland et al. |
| 10,501,706 B2 | 12/2019 | Holland et al. |
| 2014/0287982 A1 | 9/2014 | Wong et al. |
| 2015/0164764 A1 | 6/2015 | Bonnet et al. |
| 2016/0362630 A1* | 12/2016 | Holland ................. A61Q 19/00 |
| 2021/0032561 A1 | 2/2021 | Holland et al. |

FOREIGN PATENT DOCUMENTS

| | | |
|---|---|---|
| CN | 111902123 | 11/2020 |
| CN | 111902191 | 11/2020 |
| WO | WO-2011154926 A1 | 12/2011 |
| WO | WO-2013060691 A2 | 5/2013 |
| WO | WO-2016075328 A1 | 5/2016 |
| WO | WO-2019156707 A1 | 8/2019 |
| WO | WO-2019156708 A1 | 8/2019 |

OTHER PUBLICATIONS

"International Application Serial No. PCT/US2018/043700, Written Opinion mailed Oct. 26, 2018", 10 pgs.
"International Application Serial No. PCT/US2018/043721, International Search Report mailed Sep. 26, 2018", 4 pgs.
"International Application Serial No. PCT/US2018/043721, Written Opinion mailed Sep. 26, 2018", 8 pgs.
"Perfume Fixative (Glucam p. 20 humectant)", Retrieved from the Internet: <URL: https://www.creatingperfume.com/GlucamP-20humectant.aspx>, (accessed Oct. 10, 2018), 2 pgs.
"International Application Serial No. PCT/US2018/043700, International Preliminary Report on Patentability mailed Aug. 20, 2020", 12 pgs.
"International Application Serial No. PCT/US2018/043721, International Preliminary Report on Patentability mailed Aug. 20, 2020", 10 pgs.
"Brazilian Application Serial No. BR1120200160750, Office Action mailed May 9, 2022", w/English Machine Translation, 10 pgs.
"Chinese Application Serial No. 201880091860.7, Office Action mailed Jul. 20, 2022", W/English Translation, 21 pgs.
"Brazilian Application Serial No. BR1120200160750, Opinion for non-patenteability (RPI 7.1) mailed Dec. 20, 2022", W/ English Translation, 11 pgs.
"Brazilian Application Serial No. BR1120200160946, Office Action mailed May 24, 2022", w/ English translation, 4 pgs.
"Brazilian Application Serial No. BR1120200160946, Opinion for non-patenteability (RPI 7.1) mailed Dec. 13, 2022", w/ English Translation, 11 pgs.
"Chinese Application Serial No. 201880091747.9, Decision of Rejection mailed Mar. 16, 2023", 8 pgs.
"Chinese Application Serial No. 201880091747.9, Office Action mailed Jan. 5, 2023", w/ English Translation, 25 pgs.
"Chinese Application Serial No. 201880091747.9, Office Action mailed Aug. 8, 2022", w/ English translation, 17 pgs.
"Chinese Application Serial No. 201880091860.7, Office Action mailed Jan. 13, 2023", w/ English Translation, 25 pgs.
"European Application Serial No. 18752406.1, Communication Pursuant to Article 94(3) EPC mailed Feb. 2, 2023", 7 pgs.
"U.S. Appl. No. 16/967,911, Response filed Sep. 13, 2023 to Restriction Requirement mailed Jul. 14, 2023", 17 pgs.
"U.S. Appl. No. 16/967,911, Restriction Requirement mailed Jul. 14, 2023", 10 pgs.
"Chinese Application Serial No. 201880091860.7, Decision of Rejection mailed Apr. 19, 2023", w/o English Translation, 7 pgs.
"U.S. Appl. No. 16/967,911, Non Final Office Action mailed Oct. 10, 2023", 16 pgs.
"U.S. Appl. No. 16/967,911, Response filed Apr. 9, 2024 to Non Final Office Action mailed Oct. 10, 2023", 17 pgs.
"European Application Serial No. 18752958.1, Communication Pursuant to Article 94(3) EPC mailed Feb. 8, 2024", 8 pgs.
"U.S. Appl. No. 16/967,911, Notice of Non-Compliant Amendment mailed Aug. 5, 2024", 4 pgs.
"European Application Serial No. 18752958.1, Communication Pursuant to Article 94(3) EPC mailed Jun. 25, 2024", 4 pgs.
"European Application Serial No. 18752958.1, Response filed Apr. 11, 2024 to Communication Pursuant to Article 94(3) EPC mailed Feb. 8, 2024", 20 pgs.

* cited by examiner

FRAGRANCE COMPOSITIONS AND USES THEREOF

CROSS-REFERENCE TO RELATED APPLICATION

This application is a U. S. National Stage Filing under 35 U.S.C. 371 from International Application No. PCT/US2018/043721, filed on Jul. 25, 2018, and published as WO 2019/156708 on Aug. 15, 2019, which application claims the benefit of priority to U.S. Provisional Patent Application Ser. No. 62/627,437 entitled "FRAGRANCE COMPOSITIONS AND USES THEREOF," filed Feb. 7, 2018, the disclosure of which is incorporated herein in its entirety by reference.

FIELD OF THE INVENTION

Inventive subject matter herein relates to the field of perfumery. In particular, it provides compositions comprising fragrance materials in a bottom-heavy construction and at least one substantially non-odorous fragrance modulator for creating a bottom-heavy driven fragrance profile that are over-dosed with respect to the base note character without a harsh perception by a panel of experts or professional evaluators or individual experts or professional evaluators. The invention also relates to methods of making and using said compositions.

BACKGROUND OF THE DISCLOSURE

Fragrances can include fragrance components that can be classified, in part, by their volatility. Accordingly, these fragrance components may be referred to as a high-, moderate-, or low-volatility fragrance components. Different fragrances may be dominated by any one or more of these component such that the fragrance may be associated with different perceptions by a user. Furthermore, although the low-volatility fragrance may be present for a comparatively longer period of time, compositions including a relatively high amount of specific low and moderate-volatility fragrance materials (e.g., an over-dose) may be perceived as having a harsh and unpleasant perception by a panel of experts or professional evaluators or individual experts or professional evaluators. This may be especially true in cases where the low and moderate-volatility fragrance materials are, or include, natural materials.

SUMMARY OF THE DISCLOSURE

According to various embodiments, a composition includes a fragrance component present in an amount of from about 0.04 wt % to about 30 wt %, relative to the total weight of the composition. The fragrance component includes at least one low volatile fragrance material having a vapor pressure less than 0.001 Torr (0.000133 kPa) at 25° C. present in an amount greater than 30 wt %, relative to the total weight of the fragrance component. This can be defined as a bottom-heavy fragrance. The fragrance component further includes at least one moderate volatile fragrance material having a vapor pressure in the range of 0.1 Torr to 0.001 Torr (0.0133 kPa to 0.000133 kPa) at 25° C. present in an amount of from about 30 wt % to about 70 wt %, relative to the total weight of the fragrance component. The fragrance component further includes at least one high volatile fragrance material having a vapor pressure greater than 0.1 Torr (0.0133 kPa) at 25° C. present in an amount of from about 0.1 wt % to about 30 wt % relative to the total weight of the fragrance component. The composition further includes at least one substantially non-odorous fragrance modulator present in the amount of from about 0.1 wt % to about 20 wt %, relative to the total weight of the composition.

According to various further embodiments, a composition includes a fragrance component present in an amount of from about 0.04 wt % to about 30 wt %, relative to the total weight of the composition. The fragrance component includes at least one low volatile fragrance material having a vapor pressure less than 0.001 Torr (0.000133 kPa) at 25° C. present in an amount greater than 30 wt %, relative to the total weight of the fragrance component. This can be defined as a bottom-heavy fragrance. The fragrance component further includes at least one moderate volatile fragrance material having a vapor pressure in the range of 0.1 Torr to 0.001 Torr (0.0133 kPa to 0.000133 kPa) at 25° C. present in an amount of from about 30 wt % to about 70 wt %, relative to the total weight of the fragrance component. The fragrance component further includes at least one high volatile fragrance material having a vapor pressure greater than 0.1 Torr (0.0133 kPa) at 25° C. present in an amount of from about 0.1 wt % to about 30 wt % relative to the total weight of the fragrance component. The composition further includes at least one substantially non-odorous fragrance modulator is chosen from polypropylene glycol-10 methyl glucose ether, ethoxylated methyl glucose ether, and polypropylene glycol-20 methyl glucose ether, present in the amount of from about 0.1 wt % c to about 20 wt %, relative to the total weight of the composition.

According to various further embodiments, a composition includes a fragrance component present in an amount of from about 0.04 wt % to about 30 wt %, relative to the total weight of the composition. The fragrance component includes at least one low volatile fragrance material having a vapor pressure less than 0.001 Torr (0.000133 kPa) at 25° C. present in an amount greater than 30 wt %, relative to the total weight of the fragrance component. This can be defined as a bottom-heavy fragrance. The fragrance component further includes at least one moderate volatile fragrance material having a vapor pressure in the range of 0.1 Torr to 0.001 Torr (0.0133 kPa to 0.000133 kPa) at 25° C. present in an amount of from about 30 wt % to about 70 wt %, relative to the total weight of the fragrance component. The fragrance component further includes at least one high volatile fragrance material having a vapor pressure greater than 0.1 Torr (0.0133 kPa) at 25° C. present in an amount of from about 0.1 wt % to about 30 wt % relative to the total weight of the fragrance component. The fragrance component further includes at least one substantially non-odorous fragrance modulator present in the amount of from about 0.1 wt % to about 20 wt %, relative to the total weight of the composition. According to some embodiments, the perception of the low-volatile fragrance can dominate with respect to the other fragrance materials yet the composition as a whole may not be perceived as harsh to a panel of experts or professional evaluators or individual experts or professional evaluators.

According to some embodiments, at least one of the low volatile fragrance material, the moderate volatile fragrance material, and the high volatile fragrance material is present in the fragrance component for a period of time that is longer than a corresponding fragrance component that is free of the substantially non-odorous fragrance modulator.

There, are many non-limiting reasons for using the compositions of the instant disclosure. For example, according to various embodiments, the characteristics of the composition can provide rules for objectively classifying fragrance materials according to their volatility using their vapor pressures defined at suitable temperature, instead of their characters. The objective rules operate irrespective of perfumers performing the classification. In particular, the rules classify the fragrance materials into low, moderate or high volatile fragrance materials for formulating into fragrance mixtures. Furthermore, according to some embodiments, the presence of the modulator can allow for compositions where the perception of the panel of experts or professional evaluators or individual experts or professional evaluators is driven by the moderate and low-volatility fragrance materials. According to some embodiments, the modulator allows for over-dosing of at least one of the low and moderate volatility fragrance materials. By "overdosing" it is meant that either or both of the moderate volatile or low volatile materials can account for greater than 30 wt % of the fragrance component. Alternatively, the fragrance component can include multiple high or moderate volatile materials. In those instances, an individual high or low volatile material may be present in an amount greater than a corresponding material in a traditional fragrance-thus constituting an overdose. Notably, according to some embodiments, the typical harshness, as perceived by a panel of experts or professional evaluators or individual experts or professional evaluators panel of experts or professional evaluators or individual experts or professional evaluators, of large levels of low-volatility fragrance materials can be minimized at least in part by the presence of the modulator. This can be especially true, in some embodiments, in which the low-volatility fragrance material is a natural material and is over-dosed, which absent the modulator, produces a harshness that is not acceptable to a panel of experts or professional evaluators or individual experts or professional evaluators.

BRIEF DESCRIPTION OF THE FIGURES

The drawings illustrate generally, by way of example, but not by way of limitation, various embodiments discussed in the present document.

DETAILED DESCRIPTION OF THE INVENTION

Definitions

Figure 1:
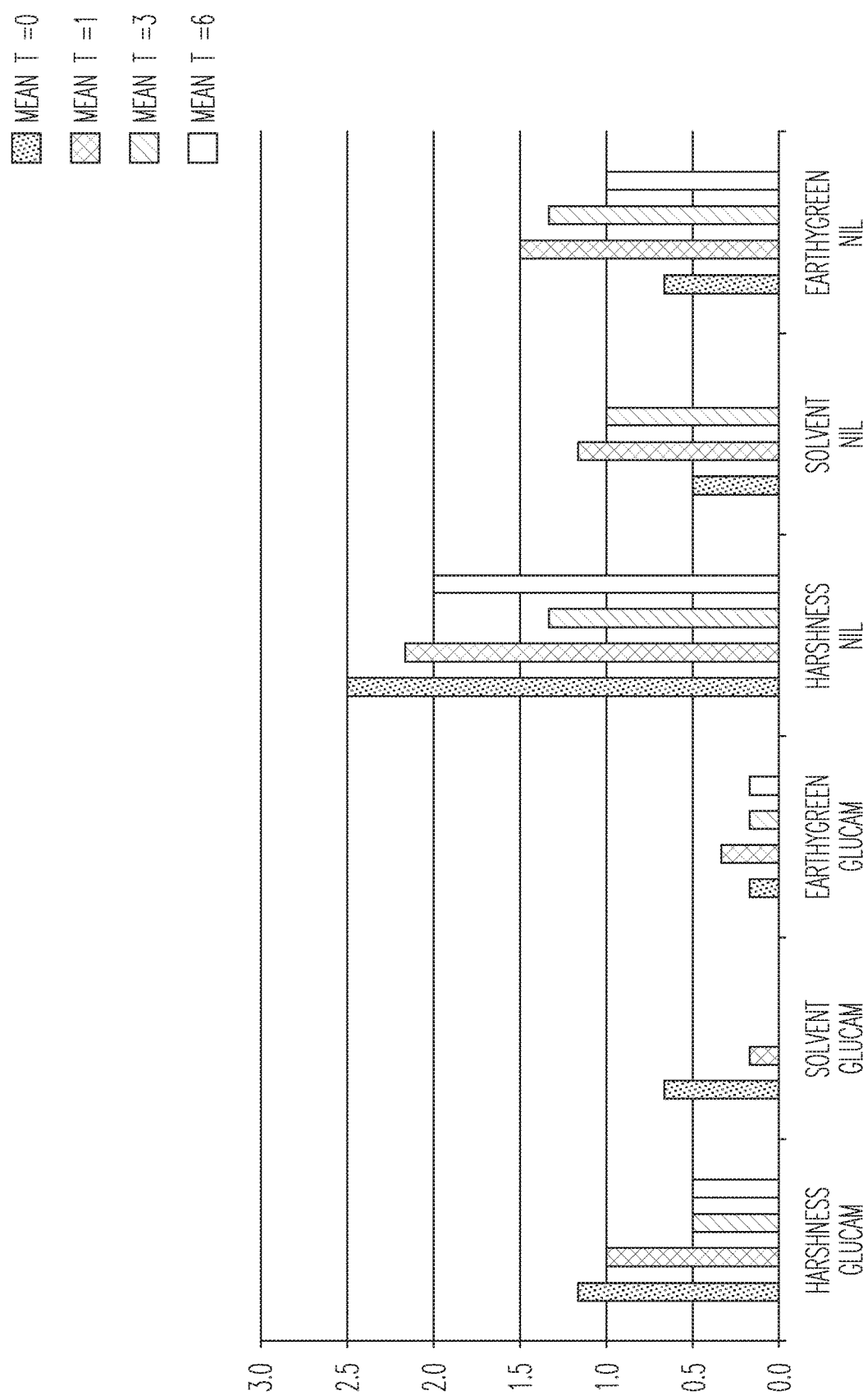
FIG. 1 shows a profile of fragrance materials in a fragrance construction according to the instant disclosure.

As used herein, articles such as "a" and "an" when used in a claim, are understood to mean one or more of what is claimed or described.

As used herein, the terms "include", "includes" and "including" are meant to be non-limiting.

As used herein, the term "body splash" means a body care formulation that is applied to the body. Typically, the body splash is applied to the body after bathing and provides a subtle hint of scent to the body. Body splashes are commonly used by consumers who prefer less strong fragrance compositions. A body splash may comprise an ethanol-free composition according to the present invention which comprises from 0.2-8 wt %, relative to the total weight of the composition, of a fragrance component. The body splash may further comprise alkyl polyglucosides as non-ionic surfactants.

As used herein, the term "body spray" means a formulation comprising fragrance materials intended to be applied to the body to prevent or mask body odor caused by the bacterial breakdown of perspiration on the body (e.g., armpits, feet, and other areas of the body). The body spray may also provide a fragrance expression to the consumers. Typically, body spray compositions are applied as an aerosol spray in an effective amount on the skin of a consumer.

As used herein, the term "composition" includes a fine fragrance composition intended for application to a body surface, such as for example, skin or hair, e.g., to impart a pleasant odor thereto, or cover a malodour thereof. They are generally in the form of perfume concentrates, perfumes, eau de parfums, eau de toilettes, aftershaves, or colognes. The fine fragrance compositions may be an ethanol-based composition. The term "composition" may also include a cosmetic composition, which comprises a fragrance material for the purposes of delivering a pleasant smell to drive consumer acceptance of the cosmetic composition. The term "composition" may also include body splashes or body sprays. The term "composition" may also include cleaning compositions, such as fabric care composition or home care compositions, including air care compositions (e.g., air fresheners), for use on clothing or other substrates such as hard surfaces (e.g., dishes, floors, countertops). Additional non-limiting examples of "composition" may also include facial or body powder, deodorant, foundation, body/facial oil, mousse, creams (e.g., cold creams), waxes, sunscreens and blocks, bath and shower gels, lip balms, self-tanning compositions, masks and patches.

As used herein, the term "consumer" means both the user of the composition and the observer nearby or around the user.

As used herein, the term "fragrance material" and "fragrance materials" relates to a perfume raw material ("PRM"), or a mixture of perfume raw materials ("PRMs"), that are used to impart an overall pleasant odor or fragrance profile to a composition. "Fragrance materials" can encompass any suitable perfume raw materials for fragrance uses, including materials such as, for example, alcohols, aldehydes, ketones, esters, ethers, acetates, nitriles, terpene hydrocarbons, nitrogenous or sulfurous heterocyclic compounds and essential oils. However, naturally occurring plant and animal oils and exudates comprising complex mixtures of various chemical components are also known for use as "fragrance materials". The individual perfume raw materials which comprise a known natural oil can be found by reference to Journals commonly used by those skilled in the art such as "Perfume and Flavourist" or "Journal of Essential Oil Research", or listed in reference texts such as the book by S. Arctander, *Perfume and Flavor Chemicals,* 1969, Montclair, New Jersey, USA and more recently republished by Allured Publishing Corporation Illinois (1994). Additionally, some perfume raw materials are supplied by the fragrance houses (Firmenich, International Flavors & Fragrances, Givaudan, Symrise) as mixtures in the form of proprietary specialty accords. Non-limiting examples of the fragrance materials useful herein include pro-fragrances such as acetal pro-fragrances, ketal pro-fragrances, ester pro-fragrances, hydrolyzable inorganic-organic pro-fragrances, and mixtures thereof. The fragrance materials may be released from the pro-fragrances in a number of ways. For example, 0 the fragrance may be released as a result of simple hydrolysis, or by a shift in an equilibrium reaction, or by a pH-change, or by enzymatic release.

As used herein, the term "fragrance profile" means the description of how the fragrance is perceived by the human nose at any moment in time. The fragrance profile may change over time. It is a result of the combination of the low, moderate and high volatile fragrance materials, if present, of a fragrance. A fragrance profile is composed of 2 characteristics: 'intensity' and 'character'. The 'intensity' relates to the perceived strength whilst 'character' refers to the odor impression or quality of the perfume, e.g., fruity, floral, woody, etc.

As used herein, the terms "modulator", and "fragrance modulator" are used interchangeably to designate an agent having the capacity to affect the fragrance profile, such as for example, by impacting the fragrance materials' evaporation rate. The modulator may mediate its effect by lowering the vapor pressure of the fragrance materials and increasing their adherence to the substrate (skin and/or hair) thus ensuring a less harsh impression of the overdosed fragrance. By incorporating the modulator, it is desired that the fragrance profile, preferably the fragrance components composition attributable to the moderate and low volatile fragrance materials, alone or individually, of the composition can be perceived by a panel of experts or professional evaluators or individual experts or professional evaluators, without the perceived harshness of overdosing (e.g., greater than about 30 wt % of the composition) of the low and moderate fragrance materials is mitigated or absent, as compared to the same perception in the absence of the modulator. Suitable examples of the modulator are provided herein below. However, as discovered by the inventors, simply adding modulators to a traditionally constructed fragrance composition (e.g., classical fragrance pyramid construction without overdose) will only decrease the overall intensity of the fragrance which is undesireable. It is necessary to overdose the key-character-giving moderate and low volatility materials, above what they would be used at in a traditional fragrance construction, in order to achieve the desired panel of experts or professional evaluators or individual experts or professional evaluators experience.

As used herein, the term "substantially non-odorous" means an agent that does not impart an odor of its own when added into a composition of the present invention. For example, a "substantially non-odorous fragrance modulator" does not impart a new odor that alters the character of the fragrance profile of the composition to which it is added. The term "substantially non-odorous" also encompasses an agent that may impart a minimal or slight odor of its own when added into a composition of the present invention. However, the odor imparted by the "substantially non-odorous fragrance modulator" is generally undetectable or tends to not substantively alter the character of the fragrance profile of the composition to which it is added initially or preferably over time. Furthermore, the term "substantially non-odorous" also includes materials that are perceivable only by a minority of people or those materials deemed "anosmic" to the majority of people. Furthermore, the term "substantially non-odorous" also includes materials that may, from particular suppliers, contain an odor due to impurities, such as when the materials contain the impurities at not more than about 5 wt %, preferably not more than 1 wt %, often even not more than 1 part per million (ppm). These impurities maybe removed by purification techniques known in the art as required to make them suitable for use in fragrance compositions of the present invention.

As used herein, the term "vapor pressure" means the partial pressure in air at a defined temperature (e.g., 25° C.) and standard atmospheric pressure (760 mmHg) for a given chemical species. It defines a chemical species' desire to be in the gas phase rather than the liquid or solid state. The higher the vapor pressure the greater the proportion of the material that will, at equilibrium, be found in a closed headspace. It is also related to the rate of evaporation of a fragrance material which is defined in an open environment where material is leaving the system. The vapor pressure is determined according to the reference program Advanced Chemistry Development (ACD/Labs) Software Version 14.02, or preferably the latest version update).

It is understood that the test methods that are disclosed in the Test Methods Section of the present application must be used to determine the respective values of the parameters of Applicants' inventions as described and claimed herein.

In all embodiments of the present invention, all percentages are by weight of the total composition, as evident by the context, unless specifically stated otherwise. All ratios are weight ratios, unless specifically stated otherwise, and all measurements are made at 25° C., unless otherwise designated.

Compositions

The inventive subject matter herein is directed towards fragrance compositions or mixtures having a bottom-heavy construction and displaying little to no perceived harshness that would be unacceptable to a panel of experts or professional evaluators or individual experts or professional evaluators. Disclosed fragrance compositions can include at least a fragrance component and modulator. The fragrance component can include a wide variety of fragrance materials. The fragrance materials can be grouped in terms of their volatility. Generally, the materials can be grouped as low volatile fragrance materials, moderate volatile fragrance materials, and high volatile fragrance materials. Each group of materials can be associated with various perceptions by a panel of experts or professional evaluators or individual experts or professional evaluators. While not so limited, a high volatile fragrance may be associated with a citrus character; a moderate voile fragrance may be associated with a spicy character; and a low volatile fragrance may be associated with a woody character. Each group of fragrance materials can include synthetic materials or natural materials. The volatility of the fragrance materials can be in reference to an individual fragrance material. Alternatively, in cases where a combination of materials produce a fragrance the volatility may be in reference to that aggregation.

With respect to the composition, the fragrance component can be present in an amount of from about 0.04 wt % to 30 wt %, 1 wt % to about 30 wt %, about 5 wt % to about 30 wt %, or less than, equal to, or greater than about 0.04 wt %, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, or about 30 wt % relative to the composition.

Additionally with respect to the composition, the modulator can be present in an amount of from about 0.1 wt % to about 20 wt %, about 0.5 wt % to about 20 wt %, or less than, equal to, or greater than about 0.1 wt %, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or about 20 wt % relative to the composition.

As described herein, the "fragrance materials" have been classified as low, moderate or high volatile fragrance materials according to their volatility by their vapor pressure. This method of classifying fragrance materials by their vapor pressure avoids the problem of different classifications for the same fragrance material according to the traditional approach that relies on their subjective characteristic character. In the case that the fragrance materials are a natural oil, extract or absolute, which comprises a mixture of several compounds, the vapor pressure of the complete oil should be treated a mixture of the individual perfume raw material components using the reference program cited above. The individual components and their level, in any given natural oil or extract, can be determined by direct injection of the oil into a GC-MS column for analysis as known by one skilled in the art. In the scenario that the fragrance materials are a proprietary specialty accord, so called 'bases', the vapor pressure, using the reference program cited above, should preferably be obtained from the supplier. However, it is understood by one skilled in the art that they can physically analyze the composition of a full fragrance oil available commercially to identity the fragrance raw materials and their levels using standard GC-MS techniques. This would be irrespective of whether they had been added to the fragrance oil as individual chemicals, as components of naturals or from proprietary bases. Although proprietary bases and naturals are included in our examples, when analyzing a commercially available fragrance via GC-MS one could simply identify the components of the base or natural oil as part of the overall fragrance mixture and their levels, without being able to identify which proprietary base or natural oil the fragrance had come from.

(i) Low Volatile Fragrance Materials

The fragrance component comprises at least one low volatile fragrance material. Individual low volatile fragrance materials or aggregate low volatile fragrance materials are those having a vapor pressure less than 0.001 Torr (0.000133 kPa) at 25° C. According to some examples, the composition can include at least 3 low volatile fragrance materials, or at least 4 low volatile fragrance materials, or at least 5 low volatile fragrance materials, or at least 7 low volatile fragrance materials. The amount of the low volatile fragrance material present in the fragrance component can vary depending on the specific application. For example, the low volatile fragrance material can be greater than about 30 wt % of the fragrance component, greater than about 40 wt %, greater than about 50 wt %, greater than about 60 wt %, about 31 wt % to about 60 wt %, about 40 wt % to about 50 wt %, or less than, equal to, or greater than about 30 wt %, 31, 35, 40, 45, 50, 55, 60, 65, 70, or 75 wt %.

If there are more than one low volatile fragrance materials, then the ranges provided hereinabove cover the total of all the low volatile fragrance materials. Examples of suitable low volatile fragrances materials are provided in Table 1A and 1B below.

Preferably, the low volatile fragrance material is selected from at least 1 material, or at least 2 materials, or at least 3 materials, or at least 5 materials, at least 7, at least 8, at least 10, or at least 12 low volatile fragrance materials as disclosed in Table 1A. Natural fragrance materials or oils having an aggregate vapour pressure less than 0.001 Torr (0.000133 kPa) at 25° C. are provided in Table 1B. Low Volatile Natural Oils.

TABLE 1A

Low Volatile Fragrance Materials

| No. | CAS Number | IUPAC Name | Common Name** | Vapor Pressure (Torr at 25° C.)* |
|---|---|---|---|---|
| 1. | 1211-29-6 | Cyclopentaneacetic acid, 3-oxo-2-(2Z)-2-penten-1-yl-, methyl ester, (1R, 2R)- | Methyl jasmonate | 0.00096500 |
| 2. | 28219-60-5 | 2-Buten-1-ol, 2-methyl-4-(2,2,3-trimethyl-3-cyclopenten-1 -yl)- | Hindinol | 0.00096100 |
| 3. | 93-08-3 | Ethanone, 142-naphthalenyl)- | Methyl beta-naphthyl ketone | 0.00095700 |
| 4. | 67633-95-8 | 3-Decanone, 1-hydroxy- | Methyl Lavender Ketone | 0.00095100 |
| 5. | 198404-98-7 | Cyclopropanemethanol, 1-methyl-2-[(1,2,2-trimethylbicyclo[3.1.0][hex-3-yl)methyl]- | Javanol ® | 0.00090200 |
| 6. | 121-32-4 | Benzaldehyde, 3-ethoxy-4-hydroxy- | Ethyl vanillin | 0.00088400 |
| 7. | 72403-67-9 | 3-Cyclohexene-1-methanol, 4-(4-methyl-3-penten-1-yl)-, 1-acetate | Myraldylacetate | 0.00087900 |
| 8. | 28940-11-6 | 2H-1,5-Benzodioxepin-3(4H)-one, 7-methyl- | Calone | 0.00083100 |
| 9. | 139504-68-0 | 2-Butanol, -1[[2-(1,1-dimethylethyl)cyclohexyl]oxy]- | Amber core | 0.00080300 |

TABLE 1A-continued

Low Volatile Fragrance Materials

| No. | CAS Number | IUPAC Name | Common Name** | Vapor Pressure (Torr at 25° C.)* |
|---|---|---|---|---|
| 10. | 502847-01-0 | Spiro[5.5]undec-8-en-1-one, 2,2,7,9-tetramethyl- | Spiro[5.5]undec-8-en-i-one, 2,2,7,9-tetramethyl- | 0.00073100 |
| 11. | 2570-03-8 | Cyclopentaneacetic acid, 3-oxo-2-pentyl-, methyl ester, (1R, 2R)-rel- | trans-Hedione | 0.00071000 |
| 12. | 24851-98-7 | Cyclopentaneacetic acid, 3-oxo-2-pentyl-, methyl ester | Methyl dihydrojasmonate or alternatives [1] | 0.00071000 |
| 13. | 101-86-0 | Octanal, 2-(phenylmethylene)- | Flexyl cinnamic aldehyde | 0.00069700 |
| 14. | 365411-50-3 | Indeno[4,5-d]-1,3-dioxin, 4,4a,5,6,7,8,9,9b-octahydro-7,7,8,9,9-pentamethyl- | Nebulone | 0.00069200 |
| 15. | 37172-53-5 | Cyclopentanecarboxylic acid, 2-hexyl-3-oxo-, methyl ester | Dihydro Iso Jasmonate | 0.00067500 |
| 16. | 65113-99-7 | 3-Cyclopentene-1-butanol, α,β,2,2,3-pentamethyl- | Sandalore ® | 0.00062500 |
| 17. | 68133-79-9 | Cyclopentanone, 2-(3,7-dimethyl-2,6-octadien-1-yl)- | Apritone | 0.00062000 |
| 18. | 7212-44-4 | 1,6,10-Dodecatrien-3-ol, 3,7,11-trimethyl- | Nerolidol | 0.00061600 |
| 19. | 53243-59-7 | 2-Pentenenitrile, 3-methyl-5-phenyl-, (2Z)- | Citronitril | 0.00061500 |
| 20. | 134123-93-6 | Benzenepropanenitrile, 4-ethyl-α,α-dimethyl- | Fleuranil | 0.00057600 |
| 21. | 77-53-2 | 1H-3a,7-Methanoazulen-6-ol, octahydro-3,6,8,8-tetramethyl-, (3R, 3aS, 6R, 7R, 8aS)- | Cedrol Crude | 0.00056900 |
| 22. | 68155-66-8 | Ethanone, 1-(1,2,3,5,6,7,8,8a-octahydro-2,3,8,8-tetramethyl-2-naphthalenyl)- | Iso Gamma Super | 0.00056500 |
| 23. | 54464-57-2 | Ethanone, 1-(1,2,3,4,5,6,7,8-octahydro-2,3,8,8-tetramethyl-2-naphthalenyl)- | Iso-E Super ® | 0.00053800 |
| 24. | 774-55-0 | Ethanone, 1-(5,6,7,8-tetrahydro-2-, naphthalenyl)- | Florantone | 0.00053000 |
| 25. | 141-92-4 | 2-Octanol, 8,8-dimethoxy-2,6-dimethyl- | Hydroxycitronellal Dimethyl Acetal | 0.00052000 |
| 26 | 20665-85-4 | Propanoic acid, 2-methyl-, 4-formyl-2-methoxyphenyl ester | Vanillin isobutyrate | 0.00051200 |
| 27. | 79-78-7 | 1,6-Heptadien-3-one, 1-(2,6,6-trimethyl-2-cyclohexen-l-yl)- | Hexalon | 0.00049800 |
| 28. | 6259-76-3 | Benzoic acid, 2-hydroxy-, hexyl ester | Hexyl Salicylate | 0.00049100 |
| 29. | 93-99-2 | Benzoic acid, phenyl ester | Phenyl Benzoate | 0.00047900 |
| 30. | 153859-23-5 | Cyclohexanepropanol, 2,2,6-trimethyl-α-propyl-, (1R, 6S)- | Norlimbanol | 0.00046900 |
| 31. | 70788-30-6 | Cyclohexanepropanol, 2,2,6-trimethyl-α-propyl- | Timberol/ Norlimbanol | 0.00046900 |

TABLE 1A-continued

Low Volatile Fragrance Materials

| No. | CAS Number | IUPAC Name | Common Name** | Vapor Pressure (Torr at 25° C.)* |
|---|---|---|---|---|
| 32. | 68555-58-8 | Benzoic acid, 2-hydroxy-, 3-methyl-2-buten-1-ylester | Prenyl Salicylate | 0.00045700 |
| 33. | 950919-28-5 | 2H-1,5-Benzodioxepin-3(4H)-one, 7-(1-methylethyl)- | Cascalone | 0.00045500 |
| 34. | 30168-23-1 | Butanal, 44octahydro-4,7-methano-5H-inden-5-ylidene)- | Dupical | 0.00044100 |
| 35. | 1222-05-5 | Cyclopenta[g]-2-benzopyran, 1,3,4,6,7,8-hexahydro-4,6,6,7,8,8-hexamethyl- | Galaxolide ® | 0.00041400 |
| 36. | 4602-84-0 | 2,6,10-Dodecatrien-1-ol, 3,7,11-trimethyl- | Farnesol | 0.00037000 |
| 37. | 95962-14-4 | Cyclopentanone, 2-[2-(4-methyl-3-cyclohexen-1-yl)propyl]- | Nectaryl | 0.00036700 |
| 38. | 4674-50-4 | 2(3H)-Naphthalenone, 4,4a,5,6,7,8-hexahydro-4,4a-dimethyl-6-(1-methylethenyl)-, (4R, 4aS, 6R)- | Nootkatone | 0.00035800 |
| 39. | 3487-99-8 | 2-Propenoic acid, 3-phenyl-, pentyl ester | Amyl Cinnamate | 0.00035200 |
| 40. | 10522-41-5 | 2-hydroxy-2-phenylethyl acetate | Styrolyl Acetate | 0.00033900 |
| 41. | 118-71-8 | 4H-Pyran-4-one, 3-hydroxy-2-methyl- | Maltol | 0.00033700 |
| 42. | 128119-70-0 | 1-Propanol, 2-methyl-3-[(1,7,7-trimethylbicyclo[2.2.1]hept-2-yl)oxy]- | Bornafix | 0.00033400 |
| 43. | 103614-86-4 | 1-Naphthalenol, 1,2,3,4,4a,5,8,8a-octahydro-2,2,6,8-tetramethyl- | Octalynol | 0.00033200 |
| 44. | 7785-33-3 | 2-Butenoic acid, 2-methyl-, (2E)-3,7-dimethyl-2,6-octadien-1-yl ester, (2E)- | Geranyl Tiglate | 0.00033200 |
| 45. | 117933-89-8 | 1,3-Dioxane, 2-(2,4-dimethyl-3-cyclohexen-1-yl)-5-methyl-5-(1-methylpropyl)- | Karanal | 0.00033100 |
| 46. | 629-92-5 | Nonadecane | Nonadecane | 0.00032500 |
| 47. | 67801-20-1 | 4-Penten-2-ol, 3-methyl-5-(2,2,3-trimethyl-3-cyclopenten-1-yl)- | Ebanol | 0.00028100 |
| 48. | 65416-14-0 | Propanoic acid, 2-methyl-, 2-methyl-4-oxo-4H-pyran-3-yl ester | Maltol Isobutyrate | 0.00028000 |
| 49. | 28219-61-6 | 2-Buten-1-ol, 2-ethyl-4-(2,2,3-tdmethyl-3-cyclopenten-1-yl)- | Laevo Trisandol | 0.00028000 |
| 50. | 5986-55-0 | 1,6-Methanonaphthalen-1(2H)-ol, octahydro-4,8a,9,9-tetramethyl-, (1R, 4S, 4aS, 6R, 8aS)- | Healingwood | 0.00027800 |
| 51. | 195251-91-3 | 2H-1,5-Benzodioxepin-3(4H)-one, 7-(1,1-dimethylethyl)- | Transluzone | 0.00026500 |
| 52. | 3100-36-5 | 8-Cyclohexadecen-1-one | Cyclohexadecenone | 0.00025300 |
| 53. | 65405-77-8 | Benzoic acid, 2-hydroxy-, (3Z)-3-hexen-1-yl ester | cis-3-Hexenyl salicylate | 0.00024600 |
| 54. | 4940-11-8 | 4H-Pyran-4-one, 2-ethyl-3-hydroxy- | Ethyl Maltol | 0.00022800 |
| 55. | 541-91-3 | Cyclopentadecanone, 3-methyl- | Muskone | 0.00017600 |
| 56. | 118-58-4 | Benzoic acid, 2-hydroxy-, phenylmethyl ester | Benzyl salicylate | 0.00017500 |

TABLE 1A-continued

Low Volatile Fragrance Materials

| No. | CAS Number | IUPAC Name | Common Name** | Vapor Pressure (Torr at 25° C.)* |
|---|---|---|---|---|
| 57. | 81783-01-9 | 6,8-Nonadien-3-one, 2,4,4,7-tetramethyl-, oxime | Labienoxime | 0.00017300 |
| 58. | 25485-88-5 | Benzoic acid, 2-hydroxy-, cyclohexyl ester | Cyclohexyl Salicylate | 0.00017300 |
| 59. | 91-87-2 | Benzene, [2-(dimethoxymethyl)-1-hepten-1-yl]- | Amyl Cinnamic Aldehyde Dimethyl Acetal | 0.00016300 |
| 60. | 104864-90-6 | 3-Cyclopentene-1-butanol, β,2,2,3-tetramethyl-δ-methylene- | Firsantol | 0.00016000 |
| 61 | 224031-70-3 | 4-Penten-1-one, 1-spiro[4.5]dec-7-en-7-yl- | Spirogalbanone | 0.00015300 |
| 62. | 134-28-1 | 5-Azulenemethanol 1,2,3,4,5,6,7,8-octahydro-α,α,3,8-tetramethyl-, 5-acetate, (3S, 5R, 8S)- | Guaiyl Acetate | 0.00013400 |
| 63. | 236391-76-7 | Acetic acid, 2-(1-oxopropoxy)-, 1-(3,3-dimethylcyclohexyl) ethyl ester | Romandolide ® | 0.00012400 |
| 64. | 115-71-9 | 2-Penten-l-ol, 5-[(1R, 3R, 6S)-2,3-dimethyltricyclo[2.2.102, 6]hept-3-yl]-2-methyl-, (2Z)- | cis-alpha-Santalol | 0.00011800 |
| 65. | 107898-54-4 | 4-Penten-2-ol, 3,3-dimethyl-5-(2,2,3-trimethyl-3-cyclopenten-1-yl)- | Polysantol ® | 0.00011700 |
| 66. | 69486-14-2 | 5,8-Methano-2H-1-benzopyran-2-one, 6-ethylideneoctahydro- | Florex ® | 0.00011000 |
| 67. | 84697-09-6 | Heptanal, 2-[(4-methylphenyl)methylene]- | Acalea | 0.00010100 |
| 68. | 14595-54-1 | 4-Cyclopentadecen-1-one, (4Z)- | Exaltenone | 0.00009640 |
| 69. | 32388-55-9 | Ethanone, 1-[(3R,3aR,7R,8aS)-2,3,4,7,8,8a-hexahydro-3,6,828-tetramethyl-1H-3a,7-methanoazulen-5-yl]- | Vertofix ® | 0.00008490 |
| 70. | 131812-67-4 | 1,3-Dioxolane, 2,4-dimethyl-2-(5,6,7,8-tetrahydro-5,5,8,8-tetramethyl-2-naphthalenyl)- | Okoumal ® | 0.00007600 |
| 71. | 106-02-5 | Oxacyclohexadecan-2-one | Exaltolide ® | 0.00006430 |
| 72. | 141773-73-1 | 1-Propanol, 2-[1-(3,3-dimethylcyclohexyl)ethoxy]-2-methyl-, 1-propanoate | Helvetolide ® | 0.00005790 |
| 73. | 63314-79-4 | 5-Cyclopentadecen-1-one, 3-methyl- | Delta Muscenone | 0.00005650 |
| 74. | 77-42-9 | 2-Penten-1-ol, 2-methyl-5-[(1S, 2R, 4R)-2-methyl-3-methylenebicyclo[2.2.1]hept-2-yl]-, (2Z)- | cis-beta-Santalol | 0.00004810 |
| 75. | 362467-67-2 | 2H-1,5-Benzodioxepin-3 (4H)-one, 7-(3-methylbutyl)- | Azurone | 0.00004770 |
| 76. | 28371-99-5 | Ethanone, 1-(2,6,10-trimethyl-2,5,9-cyclododecatrien-1-yl)- | Trimofix O | 0.00004580 |

TABLE 1A-continued

Low Volatile Fragrance Materials

| No. | CAS Number | IUPAC Name | Common Name** | Vapor Pressure (Torr at 25° C.)* |
|---|---|---|---|---|
| 77. | 16223-63-5 | 1H-3a,6-Methanoazulene-3-methanol, octahydro-7,7-dimethyl-8-methylene-, (3S, 3aR, 6R, 8aS)- | Khusimol | 0.00004400 |
| 78. | 10461-98-0 | Benzeneacetonitrile, α-cyclohexylidene- | Peonile | 0.00004290 |
| 79. | 90-17-5 | Benzenemethanol, α-(trichloromethyl)-, 1-acetate | Rosacetol | 0.00004240 |
| 80. | 50607-64-2 | Benzoic acid, 2-[(2-methylpentylidene)amino]-, methyl ester | Mevantraal | 0.00004070 |
| 81. | 29895-73-6 | 5-Hydroxy-2-benzyl-1,3-dioxane | Acetal CD | 0.00004050 |
| 82. | 94-47-3 | Benzoic acid, 2-phenylethyl ester | Phenyl Ethyl Benzoate | 0.00003480 |
| 83. | 3100-36-5 | Cyclohexadec-8-en-1-one | Globanone ® | 0.00003310 |
| 84. | 37609-25-9 | 5-Cyclohexadecen-1-One | Ambretone | 0.00003310 |
| 85. | 66072-32-0 | Cyclohexanol, 4-(1,7,7-trimethylbicyclo[2.2.1]hept-2-yl)- | Iso Bornyl Cyclohexanol | 0.00003010 |
| 86. | 31906-04-4 | 3-Cyclohexene-1-carboxaldehyde, 4-(4-hydroxy-4-methylpentyl)- | Lyral ® | 0.00002940 |
| 87. | 21145-77-7 | Ethanone, 1-(5,6,7,8-tetrahydro-3,5,5,6,8,8-hexamethyl-2-naphthalenyl)- | Musk Plus | 0.00002860 |
| 88. | 21145-77-7 | Ethanone, 1-(5,6,7,8-tetrahydro-3,5,5,6,8,8-hexamethyl-2-naphthalenyl)- | Fixolide | 0.00002860 |
| 89. | 22442-01-9 | 2-Cyclopentadecen-1-one, 3-methyl- | Muscenone | 0.00002770 |
| 90. | 109-29-5 | Oxacycloheptadecan-2-one | Silvanone Ci | 0.00002600 |
| 91. | 101-94-0 | Benzeneacetic acid, 4-methylphenyl ester | Para Cresyl Phenyl Acetate | 0.00002330 |
| 92. | 102-20-5 | Benzeneacetic acid, 2-phenylethyl ester | Phenyl Ethyl Phenyl Acetate | 0.00002300 |
| 93. | 118562-73-5 | Cyclododecaneethanol, β-methyl- | Hydroxyambran | 0.00001800 |
| 94. | 103-41-3 | 2-Propenoic acid, 3-phenyl-, phenylmethyl ester | Benzyl Cinnamate | 0.00001050 |
| 95. | 4707-47-5 | Benzoic acid, 2,4-dihydroxy-3,6-dimethyl-, methyl ester | Veramoss/ LRG201/ Evernyl | 0.00001050 |
| 96. | 183551-83-9 | Naphtho[2,1-b]furan-6(7H)-one, 8,9-dihydro-1,5,8-trimethyl-, (8R)- | Myrrhone | 0.00000977 |
| 97. | 102-17-0 | Benzeneacetic acid, (4-methoxyphenyl) methyl ester | Para Anisyl Phenyl Acetate | 0.00000813 |
| 98. | 120-11-6 | Benzene, 2-methoxy-1-(phenyltnethoxy)-4-(1-propen-l-yl)- | Benzyl Iso Eugenol | 0.00000676 |
| 99. | 102-22-7 | Benzeneacetic acid, (2E)-3,7-dimethyl-2,6-octadien-1-yl ester | Geranyl Phenyl acetate | 0.00000645 |
| 100. | 111879-80-2 | Oxacyclohexadec-12-en-2-one, (12E)- | Habanolide 100% | 0.00000431 |
| 101. | 87-22-9 | Benzoic acid, 2-hydroxy-, 2-phenylethyl ester | Phenyl Ethyl Salicylate | 0.00000299 |
| 102. | 78-37-5 | 2-Propenoic acid, 3-phenyl-, 1-ethenyl-1,5-dimethyl-4-hexen-1-yl ester | Linalyl Cinnamate | 0.00000174 |

TABLE 1A-continued

Low Volatile Fragrance Materials

| No. | CAS Number | IUPAC Name | Common Name** | Vapor Pressure (Torr at 25° C.)* |
|---|---|---|---|---|
| 103. | 28645-51-4 | Oxacycloheptadec-10-en-2-one | Ambrettolide | 0.00000139 |
| 104. | 123-69-3 | Oxacycloheptadec-8-en-2-one, (8Z)- | Ambrettollide | 0.00000136 |
| 105. | 3391-83-1 | 1,7-Dioxacycloheptadecan-8-one | Musk RI | 0.00000057 |
| 106. | 68527-79-7 | 7-Octen-2-ol, 8-(1H-indol-1-yl)-2,6-dimethyl- | Indolene | 0.000000445 |
| 107. | 89-43-0 | Methyl 2-[(7-hydroxy-3,7-dimethyloctylidene)amino] benzoate | Aurantinol | 0.0000000100 |
| 108. | 54982-83-1 | 1,4-Dioxacyclohexadecane-5,16-dione | Zenolide | 0.00000000834 |
| 109. | 105-95-3 | 1,4-Dioxacycloheptadecane-5,17-dione | Ethylene Brassylate | 0.00000000313 |
| 110. | 3681-73-0 | Hexadecanoic acid, (2E)-3,7-dimethyl-2,6-octadien-1-yl ester | Hexarose | 0.00000000300 |
| 111. | 4159-29-9 | Phenol, 4-[3-benzoyloxy)-1-propen-1-yl]-2-methoxy- | Coniferyl benzoate | 0.00000000170 |
| 112. | 144761-91-1 | Benzoic acid, 2-[(1-hydroxy-3-phenylbutyl)amino]-, methyl ester | Trifone DIPG | 0.00000000093 |

[1] Non-limiting examples of alternative qualities from various suppliers can be purchased under the following tradenames: Kharismal ® Super (IFF), Kharismal ® (IFF), Hedione ® (Firmenich), Hedione ® HC (Firmenich), Paradisone (Firmenich), Cepionate (Zenon), Super cepionate (Zenon), Claigeon ® (Zenon).
*Vapor Pressures are acquired as described in the Test Methods Section,
**Origin: The low volatile fragrance materials may be obtained from one or more of the following companies: Firmenich (Geneva, Switzerland); Symrise AG (Holzminden, Germany); Givaudan (Argenteuil, France), IFF (Hazlet, New Jersey), Bedoukian (Danbury, Connecticut), Sigma Aldrich (St. Louis, Missouri), Millennium Specialty Chemicals (Olympia Fields, Illinois), Polarone International (Jersey City, New Jersey), and Aroma & Flavor Specialties (Danbury; Connecticut).

TABLE 1B

Low Volatile Natural Oils.

| No. | Natural oil | Supplier |
|---|---|---|
| 1. | Beeswax Absolute | Robertet |
| 2. | Cedarwood Sawdust SFE | Firmenich |
| 3. | Cedarwood Oil Rect | Firmenich |
| 4. | Cedarwood Texas Light | H. Reynaud & Fils |
| 5. | Ciste Absolute | IFF |
| 6. | Cocoa Colorless Oil | Robertet |
| 7. | Cypriol Coeur Essence | Robertet |
| 8. | Guaiacwood Oil | Global Essence Inc |
| 9. | Incense Wood Natural | Robertet |
| 10. | Orris CO2 Extract | Mane |
| 11. | Patchouli Oil | IFF |
| 12. | Tolu Baume Res | Robertet |
| 13. | Vanilla Absolute | Robertet |
| 14. | Vanilla CO2 Absolute | Robertet |
| 15. | Vetivert Oil | IFF |
| 16. | Vetyvert Acetate | Robertet |

Suppliers:
Firmenich, Geneva, Switzerland
Global Essence Inc, New Jersey, USA
H. Reynaud & Fils, Montbrun-les-Bains, France
IFF, Hazlet, New Jersey, USA
Mane, Le Bar-sur-Loup, France
Robertet, Grasse, France Exemplary low volatile fragrance materials selected from the group of Tables 1A or 1B Low Volatile Fragrance Materials are preferred. However, it is understood by one skilled in the art that other low volatile fragrance materials, not recited in Tables 1A or 1B, would also fall within the scope of the present invention, so long as they have a vapor pressure less than 0.001 Torr (0.000133 kPa) at 25° C.

(ii) Moderate Volatile Fragrance Materials

The fragrance component includes at least one moderate volatile fragrance material or aggregate of volatile fragrance materials having a vapor pressure in the range of 0.1 Torr to 0.001 Torr (0.0133 kPa to 0.000133 kPa) at 25° C. In some examples, the composition according to the present disclosure can include at least 3 moderate volatile fragrance materials, or at least 5 moderate volatile fragrance materials, or at least 7 moderate volatile fragrance materials. Compositions of the present invention can include high levels of the moderate volatile fragrance materials present in an amount of from about 30 wt % to about 70 wt %, about 35 wt % to about 60 wt %, or less than equal to, or greater than about 30 wt %, 35, 40, 45, 50, 55, 60, 65, or 70 wt % of the fragrance component. If there are more than one moderate volatile fragrance materials, then the ranges provided hereinabove cover the total of all of the moderate volatile fragrance materials. Suitable examples of moderate volatile fragrances materials are provided in Table 2A and 2B below.

Preferable examples of moderate volatile fragrance materials having a vapor pressure in the range of 0.1 Torr to 0.001 Torr (0.0133 kPa to 0.000133 kPa) at 25° C. are provided in Table 2 Moderate Volatile Fragrance Materials. Preferably, the moderate volatile fragrance material is selected from at least 1 material, or at least 2 materials, or at least 3 materials, or at least 5 materials, or at least 7 moderate volatile fragrance materials as disclosed in Table 2A. Natural fragrance materials or oils having an aggregrate vapour pressure between 0.1 Torr to 0.001 Torr (0.0133 kPa to 0.000133 kPa) at 25° C. are provided in Table 2B. Moderate Volatile Natural Oils.

TABLE 2A

Moderate Volatile Fragrance Materials

| No. | CAS Number | IUPAC Name | Common Name** | Vapor Pressure (Torr at 25° C.)* |
|---|---|---|---|---|
| 1. | 24168-70-5 | Pyrazine, 2-methoxy-3-(1-methylpropyl)- | Methoxyiso butylpyrazine | 0.09950000 |
| 2. | 89-79-2 | Cyclohexanol, 5-methyl-2-(1-methylethenyl)-, (1R, 2S, 5R)- | Iso-Pulegol | 0.09930000 |
| 3. | 112-12-9 | 2-Undecanone | Methyl Nonyl Ketone | 0.09780000 |
| 4. | 103-05-9 | Benzenepropanol, α,α-dimethyl- | Phenyl Ethyl Dimethyl Carbinol | 0.09770000 |
| 5. | 125-12-2 | Bicyclo[2.2.1]heptan-2-ol, 1,7,7-trimethyl-, 2-acetate, (1R, 2R, 4R)-rel- | Iso Bornyl Acetate | 0.09590000 |
| 6. | 78-70-6 | 1,6-Octadien-3-ol, 3,7-dimethyl- | Linalool | 0.09050000 |
| 7. | 101-97-3 | Benzeneacetic acid, ethyl ester | Ethyl Phenyl Acetate | 0.08970000 |
| 8. | 100-86-7 | Benzeneethanoll, α,α-dimethyl- | Dimethyl Benzyl Carbinol | 0.08880000 |
| 9. | 188570-78-7 | Cyclopropanecarboxyllic acid, (3Z)-3-hexen-1-yl ester | Montaverdi | 0.08640000 |
| 10. | 67634-25-7 | 3-Cyclohexene-1-methanol, 3,5-dimethyl-, 1-acetate | Floralate | 0.08500000 |
| 11. | 112-44-7 | Undecanal | Undecyl Aldehyde | 0.08320000 |
| 12. | 32669-00-4 | Ethanone, 1-(3-cycloocten-l-yl)- | Tanaisone ® | 0.08150000 |
| 13. | 98-53-3 | Cyclohexanone, 4-(1,1-dimethylethyl)- | Patchi | 0.07780000 |
| 14. | 35854-86-5 | 6-Nonen-1-ol, (6Z)- | cis-6-None-1-ol | 0.07770000 |
| 15. | 5331-14-6 | Benzene, (2-butoxyethyl)- | Butyl phenethyl ether | 0.07760000 |
| 16. | 80-57-9 | Bicyclo[3.1.1]hept-3-en-2-one, 4,6,6-trimethyl- | Verbenone | 0.07730000 |
| 17. | 22471-55-2 | Cyclohexanecarboxylic acid, 2,2,6-trimethyl-, ethyl ester, (1R, 6S)-rel- | Thesaron | 0.07670000 |
| 18. | 60-12-8 | Benzeneethanol | Phenethyl alcohol | 0.07410000 |
| 19. | 106-26-3 | 2,6-Octadienal, 3,7-dimethyl-, (2Z)- | Neral | 0.07120000 |
| 20. | 5392-40-5 | 2,6-Octadienal 3,7-dimethyl- | Citral | 0.07120000 |
| 21. | 89-48-5 | Cyclohexanol, 5-methyl-2-(1-methylethyl)-, 1-acetate, (1R, 2S, 5R)-rel- | Menthyl Acetate | 0.07070000 |
| 22. | 119-36-8 | Benzoic acid, 2-hydroxy-, methyl ester | Methyl salicylate | 0.07000000 |
| 23. | 104-46-1 | Benzene, 1-methoxy-4-(1E)-1-propen-1-yl- | Anethol | 0.06870000 |
| 24. | 7549-37-3 | 2,6-Octadiene 1,1-dimethoxy-3,7-dimethyl- | Citral Dimethyl Acetal | 0.06780000 |
| 25. | 25225-08-5 | Cyclohexanemethanol, α,3,3-trimethyl-, 1-formate | Aphermate | 0.06780000 |

TABLE 2A-continued

Moderate Volatile Fragrance Materials

| No. | CAS Number | IUPAC Name | Common Name** | Vapor Pressure (Torr at 25° C.)* |
|---|---|---|---|---|
| 26. | 3913-81-3 | 2-Decenal (2E)- | 2-Decene-1-al | 0.06740000 |
| 27. | 15373-31-6 | 3-Cyclopentene-1-acetonitrile, 2,2,3-trimethyl- | Cantryl ® | 0.06700000 |
| 28. | 6485-40-1 | 2-Cyclohexen-l-one, 2-methyl-5-(1-methylethenyl)-, (5R)- | Laevo carvone | 0.06560000 |
| 29. | 16587-71-6 | Cyclohexa.none, 4-(1,1-dimethytpropyl)- | Orivone | 0.06490000 |
| 30. | 62406-73-9 | 6,10-Dioxaspiro[4.5]decane, 8,8-dimethyl-7-(1-methylethyl)- | Opalal CI | 0.06290000 |
| 31. | 3720-16-9 | 2-Cyclohexen-1-one, 3-methyl-5-propyl- | Livescone | 0.06270000 |
| 32. | 13816-33-6 | Benzonitrile, 4-(1-methylethyl)- | Cumin Nitrile | 0.06230000 |
| 33. | 67019-89-0 | 2,6-Nonadienenitrile | Violet -Nitrile | 0.06200000 |
| 34. | 53398-85-9 | Butanoic acid, 2-methyl-, (3Z)-3-hexen-l-yl ester | cis-3-Hexenyl Alpha Methyl Butyrate | 0.06130000 |
| 35. | 208041-98-9 | n/a | Jasmonitrile | 0.05920000 |
| 36. | 16510-27-3 | Benzene, 1-(cyclopropylmethyl)-4-methoxy- | Toscanol | 0.05870000 |
| 37. | 111-80-8 | 2-Nonynoic acid, methyl ester | Methyl Octine Carbonate | 0.05680000 |
| 38. | 103-45-7 | Acetic acid, 2-phenyl ethyl ester | Phenyl Ethyl Acetate | 0.05640000 |
| 39. | 2550-26-7 | 2-Butanone, 4-phenyl- | Benzyl Acetone | 0.05570000 |
| 40. | 13491-79-7 | Cyclohexanol, 2-(1,1-dimethylethyl)- | Verdol | 0.05430000 |
| 41. | 7786-44-9 | 2,6-Nonadien-1-ol | 2,6-Nonadien-1-ol | 0.05370000 |
| 42. | 103-28-6 | Propanoic acid, 2-methyl-, phenylmethyl ester | Benzyl Iso Butyrate | 0.05130000 |
| 43. | 104-62-1 | Formic acid, 2-phenylethyl ester | Phenyl Ethyl Formate | 0.05050000 |
| 44. | 28462-85-3 | Bicyclo[2.2.1]heptan-2-ol, 1,2,3,3-tetramethyl-, (1R, 2R, 4S)-rel- | Humus Ether | 0.04870000 |
| 45. | 122-03-2 | Benzaldehyde, 4-(1-methylethyl)- | Cuminic Aldehyde | 0.04820000 |
| 46. | 358331-95-0 | 2,5-Octadien-4-one, 5,6,7-trimethyl-, (2E)- | Pomarose | 0.04810000 |
| 47. | 562-74-3 | 3-Cyclohexen-l-ol, 4-methyl-1-(1-methyl ethyl)- | Terpinenol-4 | 0.04780000 |
| 48. | 68527-77-5 | 3-Cyclohexene-1-methanol, 2,4,6-trimethyl- | Isocyclogeraniol | 0.04640000 |
| 49. | 35852-46-1 | Pentanoic acid, (3Z)-3-hexen-1-yl ester | Cis-3-Hexenyl Valerate | 0.04580000 |
| 50. | 2756-56-1 | Bicyclo[2.2.1]heptan-2-ol, 1,7,7-trimethyl-, 2-propanoate, (1R, 2R, 4R)-rel- | Iso Bornyl Propionate | 0.04540000 |
| 51. | 14374-92-6 | Benzene, 1-methyl-4-(1-methylethyl)-2-(1-propen-1-yl)- | Verdoracine | 0.04460000 |
| 52. | 6784-13-0 | 3-Cyclohexene-1-propanal, β,4-dimethyl- | Umonenal | 0.04380000 |
| 53. | 8000-41-7 | 2-(4-methyl-1-cyclohex-3-enyl)propan-2-ol | Alpha Terpineol | 0.04320000 |

TABLE 2A-continued

Moderate Volatile Fragrance Materials

| No. | CAS Number | IUPAC Name | Common Name** | Vapor Pressure (Torr at 25° C.)* |
|---|---|---|---|---|
| 54. | 41884-28-0 | 1-Hexanol, 5-methyl-2-(1-methylethyl)-, (2R)- | Tetrahydro Lavandulol | 0.04230000 |
| 55. | 22457-23-4 | 3-Heptanone, 5-methyl-, oxime | Stemone ® | 0.04140000 |
| 56. | 104-50-7 | 2 (3H)-Furanone, 5-butyldihydro- | Gamma Octal actone | 0.04080000 |
| 57. | 143-08-8 | 1-Nonanol | Nonyl Alcohol | 0.04070000 |
| 58. | 3613-30-7 | Octanal, 7-methoxy-3,7-dimethyl- | Methoxycitronellal | 0.04020000 |
| 59. | 67634-00-8 | Acetic acid, -(3-methylbutoxy)-, 2-propen-1-yl ester | Allyl Amyl Glycolate | 0.04000000 |
| 60. | 464-45-9 | Bicyclo[2.2.1]heptan-2-ol, 1,7,7-trimethyl-, (1S, 2R, 4S)- | 1-Borneol | 0.03980000 |
| 61. | 124-76-5 | Bicyclo[2.2.1]heptan-2-ol, 1,7,7-trimethyl-, (1R, 2R, 4R)-rel- | 1.7.7-Trimethyl-Bicyclo-1.2.2-Heptanol-2 | 0.03980000 |
| 62. | 67874-72-0 | Cyclohexanol, 2-(1,1-dimethylpropyl)-, 1-acetate | Coniferan | 0.03980000 |
| 63. | 80-26-2. | 3-Cyclohexene-1-methanol, α,α,4-trimethyl-, 1-acetate | Terpinyl Acetate | 0.03920000 |
| 64. | 498-81-7 | Cyclohexanemethanol, α,α,4-trimethyl- | Dihydro Terpineol | 0.03920000 |
| 65. | 112-45-8 | 10-Undecenal | Undecylenic aldehyde | 0.03900000 |
| 66. | 35044-57-6 | 2,4-Cyclohexadiene-1-carboxylic acid, 2,6,6-trimethyl-, ethyl ester | Ethyl Safranate | 0.03880000 |
| 67. | 106-21-8 | 1-Octanol, 3,7-dimethyl- | Dimethyl Octanol | 0.03860000 |
| 68. | 84560-00-9 | Cyclopentanol, 2-pentyl- | Cyclopentol | 0.03790000 |
| 69. | 82461-14-1 | Furan, tetrahydro-2,4-dimethyl-4-phenyl- | Rhubafuran ® | 0.03780000 |
| 70. | 56011-02-0 | Benzene, [2-(3-methylbutoxy)ethyl]- | Phenyl Ethyl Isoamyl Ether | 0.03690000 |
| 71. | 103-37-7 | Butanoic acid, phenylmethyl ester | Benzyl Butyrate | 0.03660000 |
| 72. | 6378-65-0 | Hexyl hexanoate | Hexyl hexanoate | 0.03490000 |
| 73. | 118-61-6 | Benzoic acid, 2-hydroxy-, ethyl ester | Ethyl salicylate | 0.03480000 |
| 74. | 98-52-2 | Cyclohexanol, 4-(1,1-dimethylethyl)- | Patchon | 0.03480000 |
| 75. | 115-99-1 | 1,6-Octadien-3-ol, 3,7-dimethyl-, 3-formate | Linalyl Formate | 0.03440000 |
| 76. | 112-54-9 | Dodecanal | Lauric Aldehyde | 0.03440000 |
| 77. | 53046-97-2 | 3,6-Nonadien-1-ol, (3Z, 6Z)- | 3,6 Nonadien-1-ol | 0.03360000 |
| 78. | 76649-25-7 | 3,6-Nonadien-1-ol | 3,6-Nonadien-1-ol | 0.03360000 |
| 79. | 141-25-3 | 3,7-Dimethyloct-6-en-ol | Rhodinol | 0.03290000 |
| 80. | 1975-78-6 | Decanenitrile | Decanonitdle | 0.03250000 |
| 81. | 2216-51-5 | Cyclohexanol, 5-methyl-2-(1-methylethyl)-, (1R, 2S, 5R)- | L-Menthol | 0.03230000 |
| 82. | 3658-77-3 | 4-hydroxy-2,5-dimethylfuran-3-one | Pineapple Ketone | 0.03200000 |
| 83. | 103-93-5 | Propanoic acid, 2-methyl-, 4-methylphenyl ester | Para Cresyl iso-Butyrate | 0.03120000 |

TABLE 2A-continued

Moderate Volatile Fragrance Materials

| No. | CAS Number | IUPAC Name | Common Name** | Vapor Pressure (Torr at 25° C.)* |
|---|---|---|---|---|
| 84. | 24717-86-0 | Propanoic acid, 2-methyl-, (1R, 2S, 4R)-1,7,7-trimethylbicyclo[2.2.1]hept-2-yl ester, rel- | Abierate | 0.03110000 |
| 85. | 67845-46-9 | Acetaldehyde, 2-(4-methylphenoxy)- | Aldehyde XI | 0.03090000 |
| 86. | 67883-79-8 | 2-Butenoic acid, 2-methyl-, (3Z)-3-hexen-l-yl ester, (2E)- | Cis-3-Hexenyl Tiglate | 0.03060000 |
| 87. | 33885-51-7 | Bicyclo[3.1.1]hept-2-ene-2-propanal, 6,6-dimethyl- | Pino Acetaldehyde | 0.03040000 |
| 88. | 105-85-1 | 6-Octen-1-ol, 3,7-dimethyl-, 1-formate | Citronellyl Formate | 0.03000000 |
| 89. | 70214-77-6 | 2-Nonanol, 6,8-dimethyl- | Nonadyl | 0.03010000 |
| 90. | 215231-33-7 | Cyclohexanol, 1-methyl-3-(2-methylpropyl)- | Rossitol | 0.02990000 |
| 91. | 120-72-9 | 1H-Indole | Indole | 0.02980000 |
| 92. | 2463-77-6 | 2-Undecenal | 2-Undecene-l-al | 0.02970000 |
| 93. | 675-09-2 | 2H-Pyran-2-one, 4,6-dimethyl- | Levistamel | 0.02940000 |
| 94. | 98-55-5 | 3-Cyclohexene-1-methanol, α,α,4-trimethyl- | Alpha-Terpineol | 0.02830000 |
| 95. | 81786-73-4 | 3-Hepten-2-one, 3,4,5,6,6-pentamethyl-, (3Z)- | Koavone | 0.02750000 |
| 96. | 122-97-4 | Benzenepropanol | Phenyl Propyl Alcohol | 0.02710000 |
| 97. | 39212-23-2 | 2 (3H)-Furanone, 5-butyldihydro-4-methyl- | Methyl Octalactone | 0.02700000 |
| 98. | 53767-93-4 | 7-Octen-2-ol, 2,6-dimethyl-, 2-acetate | Dihydro Terpinyl Acetate | 0.02690000 |
| 99. | 35044-59-8 | 1,3-Cyclohexadiene-1-carboxylic acid, 2,6,6-trimethyl-, ethyl ester | Ethyl Safranate | 0.02660000 |
| 100. | 104-55-2 | 2-Propenal, 3-phenyl- | Cinnamic Aldehyde | 0.02650000 |
| 101. | 144-39-8 | 1,6-Octadien-3-ol, 3,7-dimethyl-, 3-propanoate | Linatyl Propionate | 0.02630000 |
| 102. | 61931-80-4 | 1,6-Nonadien-3-ol, 3,7-dimethyl-, 3-acetate | 3,7-Dimethyl-1,6-nonadien-3-yl acetate | 0.02630000 |
| 103. | 102-13-6 | Benzeneacetic acid, 2-methylpropyl ester | Iso Butyl Phenylacetae | 0.02630000 |
| 104. | 65443-14-3 | Cyclopentanone, 2,2,5-trimethyl-5-pentyl- | Veloutone | 0.02610000 |
| 105. | 141-12-8 | 2,6-Octadien-1-ol, 3,7-dimethyl-, 1-acetate, (2Z)- | Neryl Acetate | 0.02560000 |
| 106. | 105-87-3 | 2,6-Octadien-1-o1, 3,7-dimethyl-, 1-acetate, (2E)- | Geranyl acetate | 0.02560000 |
| 107. | 68141-17-3 | Undecane, 1,1-dimethoxy-2-methyl- | Methyl Nonyl Acetaldehyde Dimethyl Acetal | 0.02550000 |
| 108. | 2206-94-2 | Benzenemethanol, α-methylene-, 1-acetate | Indocolore | 0.02550000 |
| 109. | 10528-67-3 | Cyclohexanepropanol, α-methyl- | Cyclohexylmagnol | 0.02550000 |
| 110. | 123-11-5 | Benzaldehyde, 4-methoxy- | Anisic Aldehyde | 0.02490000 |
| 111. | 57576-09-7 | Cyclohexanol, 5-methyl-2-(1-methylethenyl)-, 1-acetate, (1R, 2S, 5R)- | Iso Pulegol Acetate | 0.02480000 |

TABLE 2A-continued

Moderate Volatile Fragrance Materials

| No. | CAS Number | IUPAC Name | Common Name** | Vapor Pressure (Torr at 25° C.)* |
|---|---|---|---|---|
| 112. | 51566-62-2 | 6-Octenenitrile, 3,7-dimethyl- | Citronellyl Nitrile | 0.02470000 |
| 113. | 60335-71-9 | 2H-Pyran, 3,6-dihydro-4-methyl-2-phenyl- | Rosyrane Super | 0.02470000 |
| 114. | 30385-25-2 | 6-Octen-2-ol, 2,6-dimethyl- | Dihydromyrcenol | 0.02440000 |
| 115. | 101-84-8 | Benzene, 1,1'-oxybis- | Diphenyl Oxide | 0.02230000 |
| 116. | 136-60-7 | Benzoic acid, butylester | Butyl Benzoate | 0.02170000 |
| 117. | 93939-86-7 | 5,8-Methano-2H-1-benzopyran, 6-ethylideneoctahydro- | Rhuboflor | 0.02120000 |
| 118. | 83926-73-2 | Cyclohexanepropanol, α,α-dimethyl- | Coranol | 0.02100000 |
| 119. | 125109-85-5 | Benzenepropanal, β-methyl-3-(1-methylethyl)- | Florhydral | 0.02070000 |
| 120. | 104-21-2 | Benzenemethanol, 4-methoxy-, 1-acetate | Anisyl Acetate | 0.02050000 |
| 121. | 1365-19-1 | 2-Furanmethanol, 5-ethenyltetrahydro-α,α,5-trimethyl- | Linalool Oxide | 0.02050000 |
| 122. | 137-03-1 | Cyclopentanone, 2-heptyl- | Frutal one | 0.02040000 |
| 123. | 2563-07-7 | Phenol, 2-ethoxy-4-methyl- | Ultravanil | 0.02030000 |
| 124. | 1128-08-1 | 2-Cyclopenten-1-one, 3-methyl-2-pentyl- | Dihydrojasmone | 0.02020000 |
| 125. | 7493-57-4 | Benzene, [2-(1-propoxyethoxy)ethyl]- | Acetaldehyde | 0.01990000 |
| 126. | 141-25-3 | 7-Octen-1-ol, 3,7-dimethyl- | Rhodinol | 0.01970000 |
| 127. | 216970-21-7 | Bicyclo[4.3.1]decane, 3-methoxy-7,7-dimethyl-10-methylene- | 3-Methoxy-7,7-dimethyl-10-methylenebicyclo[4.3.1]decane | 0.01960000 |
| 128. | 319002-92-1 | Propanoic acid, 2-(1,1-dimethylpropoxy)-, propyl ester, (2S)- | Sclareolate ® | 0.01960000 |
| 129. | 85-91-6 | Benzoic acid, (methylamino)-, methyl | 2-Dimethyl anthranilate | 0.01930000 |
| 130. | 13828-37-0 | Cyclohexanemethanol, 4-(1-methylethyl)-, cis- | Mayol | 0.01920000 |
| 131. | 26330-65-4 | (E)-6-ethyl-3-methyloct-6-en-1-ol | Super Muguet | 0.01850000 |
| 132. | 7540-51-4 | 6-Octen-1-ol, 3,7-dimethyl-, (3S)- | L-Citronellol | 0.01830000 |
| 133. | 106-22-9 | 6-Octen-1-ol, 3,7-dimethyl- | Citronellol | 0.01830000 |
| 134. | 543-39-5 | 7-Octen-2-ol, 2-methyl-6-methylene- | Myrcenol | 0.01820000 |
| 135. | 7775-00-0 | Benzenepropanal, 4-(1-methyl ethyl)- | Cyclemax | 0.01820000 |
| 136. | 18479-54-4 | 4,6-Octadien-3-ol, 3,7-dimethyl- | Muguol | 0.01800000 |
| 137. | 29214-60-6 | Octanoic acid, 2-acetyl-, ethyl ester | Gelsone | 0.01790000 |
| 138. | 1209-61-6 | 5-Oxatricyclo[8.2.0.04, 6]dodecane, 4,9,12,12-tetramethyl- | Tobacarol | 0.01730000 |
| 139. | 57934-97-1 | 2-Cyclohexene-1-carboxylic acid, 2-ethyl-6,6-dimethyl-, ethyl ester | Givescone | 0.01710000 |

TABLE 2A-continued

Moderate Volatile Fragrance Materials

| No. | CAS Number | IUPAC Name | Common Name** | Vapor Pressure (Torr at 25° C.)* |
|---|---|---|---|---|
| 140. | 14901-07-6 | 3-Buten-2-one, 4-(2,676-trimethyl-1-cyclohexen-l-yl)-, (3E)- | Beta-Inone | 0.01690000 |
| 141. | 64001-15-6 | 4,7-Methano-1H-inden-5-ol, octahydro-, 5-acetate | Dihydro Cyclacet | 0.01630000 |
| 142. | 95-41-0 | 2-Cyclopenten-1-one, 2-hexyl- | Iso Jasmone T | 0.01600000 |
| 143. | 134-20-3 | Benzoic acid, 2-amino-, methyl ester | Methyl Anthranilate | 0.01580000 |
| 144. | 100-06-1 | Ethanone, 1-(4-methoxyphenyl)- | Para Methoxy Acetophenone | 0.01550000 |
| 145. | 105-86-2 | 2,6-Octadien-1-ol, 3,7-dimethyl-, 1-formate, (2E)- | Geranyl Formate | 0.01540000 |
| 146. | 154171-77-4 | Spiro[1,3-dioxolane-2,8'(5'H)-[2H-2,4a]methanonaphthalene], hexahydro-1',1',5',5'-tetramethyl-, (2'S, 4'aS, 8'aS)- (9C1) | Ysamber K ® | 0.01470000 |
| 147. | 154171-76-3 | Spiro[1,3-dioxolane-2,8'(5'H)-[2H-2,4a]methanonaphthalene], | Ysamber | 0.01470000 |
| 148. | 127-41-3 | 3-Buten-2-one, 4-(2,6,6-trimethyl-2-cyclohexen-1-yl)-, (3E)- | Alpha-Ionone | 0.01440000 |
| 149. | 151-05-3 | Benzeneethanol, α,α-dimethyl-, 1-acetate | Dimethyl Benzyl Carbinyl Acetate | 0.01390000 |
| 150. | 2500-83-6 | 4,7-Methano-1H-inden-5-ol, 3a,4,5,6,7,7a-hexahydro-, 5-acetate | Flor Acetate | 0.01370000 |
| 151. | 150-84-5 | 6-Octen-1-ol, 3,7-dimethyl-, 1-acetate | Citronellyl acetate | 0.01370000 |
| 152. | 30310-41-9 | 2H-Pyran, tetrahydro-2-methyl-4-methylene-6-phenyl- | Pelargene | 0.01350000 |
| 153. | 68845-00-1 | Bicyclo[3.3.1]nonane, 2-ethoxy-2,6,6-trimethyl-9-methylene- | Boisiris | 0.01350000 |
| 154. | 106-24-1 | 2,6-Octadien-1-ol, 3,7-dimethyl-, (2E)- | Geraniol | 0.01330000 |
| 155. | 106-25-2 | 2,6-Octadien-1-ol, 3,7-dimethyl-, (2Z)- | Nerol | 0.01330000 |
| 156. | 75975-83-6 | Bicyclo[7.2.0]undec-4-ene, 4,11,11-trimethyl-8-methylene-, (1R, 4E, 9S)- | Vetyvenal | 0.01280000 |
| 157. | 19870-74-7 | 1H-3a,7-Methanoazulene, octahydro-6-methoxy-3,6,8,8-tetramethyl-, (3R, 3aS, 6S, 7R, 8aS)- | Cedryl methyl ether | 0.01280000 |
| 158. | 87-44-5 | Bicyclo[7.1.0]undec-4-ene, 4,11,11-trimethyl-8-methylene-, (1R, 4E, 9S)- | Caryophyllene Extra | 0.01280000 |
| 159. | 54440-17-4 | 1H-Inden-1-one, 2,3-dihydro-2,3,3-trimethyl- | Safraleine | 0.01260000 |

TABLE 2A-continued

Moderate Volatile Fragrance Materials

| No. | CAS Number | IUPAC Name | Common Name** | Vapor Pressure (Torr at 25° C.)* |
|---|---|---|---|---|
| 160. | 110-98-5 | 2-Propanol, 1,1'-oxybis- | Dipropylene Glycol | 0.01250000 |
| 161. | 41890-92-0 | 2-Octanol, 7-methoxy-3,7-dimethyl- | Osyrol ® | 0.01250000 |
| 162. | 71077-31-1 | 4,9-Decadienal, 4,8-dimethyl- | Floral Super | 0.01230000 |
| 163. | 65-85-0 | Benzoic Acid | Benzoic Acid | 0.01220000 |
| 164. | 61444-38-0 | 3-Hexenoic acid, (3Z)-3-hexen-1-yl ester, (3Z)- | cis-3-hexenyl-cis-3-hexenoate | 0.01220000 |
| 165. | 116044-44-1 | Bicyclo[2.2.1]hept-5-ene-2-carboxylic acid, 3-(1- | Herbanate | 0.01210000 |
| 166. | 104-54-1 | 2-Propen-1-ol, 3-phenyl- | Cinnamic Alcohol | 0.01170000 |
| 167. | 78-35-3 | Propanoic acid, 2-methyl-, 1-ethenyl-1,5-dimethyl-4-hexen-1-yl ester | Linalyl Isobutyrate | 0.01170000 |
| 168. | 23495-12-7 | Ethanol, 2-phenoxy-, 1-propanoate | Phenoxy Ethyl Propionate | 0.01130000 |
| 169. | 103-26-4 | 2-Propenoic acid, 3-phenyl-, methyl ester | Methyl Cinnamate | 0.01120000 |
| 170. | 67634-14-4 | Benzenepropanal, 2-ethyl-α,α-dimethyl- | Florazon (ortho-isomer) | 0.01110000 |
| 171. | 5454-19-3 | Propanoic acid, decyl ester | N-Decyl Propionate | 0.01100000 |
| 172. | 93-16-3 | Benzene, 1,2-dimethoxy-4-(1-propen-1-yl)- | Methyl Iso Eugenol | 0.01100000 |
| 173. | 81782-77-6 | 3-Decen-5-ol, 4-methyl- | 4-Methyl-3-decen-5-ol | 0.01070000 |
| 174. | 67845-30-1 | Bicyclo[2.2.2]oct-5-ene-2-carboxaldehyde, 6-methyl-8-(1-methylethyl)- | Maceal | 0.01060000 |
| 175. | 97-53-0 | Phenol, 2-methoxy-4-(2-propen-1-yl)- | Eugenol | 0.01040000 |
| 176. | 120-57-0 | 1,3-Benzodioxole-5-carboxaldehyde | Heliotropin | 0.01040000 |
| 177. | 93-04-9 | Naphthalene, 2-methoxy- | Beta Naphthyl Methyl Ether Extra 99 | 0.01040000 |
| 178. | 4826-62-4 | 2-Dodecenal | 2 Dodecene-l-al | 0.01020000 |
| 179. | 20407-84-5 | 2-Dodecenal, (2E)- | Aldehyde Mandarin | 0.01020000 |
| 180. | 5462-06-6 | Benzenepropanall, 4-methoxy-α-methyl- | Canthoxal | 0.01020000 |
| 181. | 94-60-0 | 1,4-Cyclohexanedicarboxylic acid, 1,4-dimethyl ester | Dimethyl 1,4-cyclohexanedicarboxylate | 0.01020000 |
| 182. | 57378-68-4 | 2-Buten-1-one, 1-(2,6,6-trimethyl-3-cyclohexen-1-yl)- | delta-Damascone | 0.01020000 |
| 183. | 17283-81-7 | 2-Butanone, 4-(2,6,6-trimethyl-1-cyclohexen-1-yl)- | Dihydro Beta Ionone | 0.01020000 |
| 184. | 1885-38-7 | 2-Propenenitrile, 3-phenyl-, (2E)- | Cinnamalva | 0.01010000 |
| 185. | 103-48-0 | Propanoic acid, 2-methyl-, 2-phenylethyl ester | Phenyl Ethyl Iso Butyrate | 0.00994000 |
| 186. | 488-10-8 | 2-Cyclopenten-1-one, 3-methyl-2-(2Z)-2-penten-1-yl- | Cis Jasmone | 0.00982000 |
| 187. | 7492-67-3 | Acetaldehyde, 2-[(3,7-dimethyl-6-octen-1-yl)oxy]- | Citronellyloxyacetaldehyde | 0.00967000 |

TABLE 2A-continued

Moderate Volatile Fragrance Materials

| No. | CAS Number | IUPAC Name | Common Name** | Vapor Pressure (Torr at 25° C.)* |
|---|---|---|---|---|
| 188. | 68683-20-5 | 1-Cyclohexene-1-ethanol, 4-(1-methylethyl)-, 1-formate | Iso Bergamate | 0.00965000 |
| 189. | 3025-30-7 | 2,4-Decadienoic acid, ethyl ester, (2E, 4Z)- | Ethyl 2,4-Decadienoate | 0.00954000 |
| 190. | 103-54-8 | 2-Propen-1-ol, 3-phenyl-, 1-acetate | Cinnamyl Acetate | 0.00940000 |
| 191. | 18127-01-0 | Benzenepropanal, 4-(1,1-dimethylethyl)- | Bourgeonal | 0.00934000 |
| 192. | 3738-00-9 | Naphtho[2,1-b]furan, dodecahydro-3a,6,6,9a-tetramethyl- | Ambrox ® or Cetalox ® or Synambran | 0.00934000 |
| 193. | 51519-65-4 | 1,4-Methanonaphthalen-5 (1H)-one, 4,4a,6,7,8,8a-hexahydro- | Tamisone | 0.00932000 |
| 194. | 148-05-1 | Dodecanoic acid, 12-hydroxy-, λ-lactone | Dodecalactone | 0.00931000 |
| 195. | 6790-58-5 | (6C1, 7CI); 1,12-(3aR, 5aS, 9aS, 9bR)-3a,6,6,9a-tetramethyl-2,4,5,5a,7,8,9,9b-octahydro-1H-benzo[e][1]benzofuran | Ambronat ® or Ambroxan ® | 0.00930000 |
| 196. | 86-26-0 | 1-1'-Biphenyl, 2-methoxy- | Methyl Diphenyl Ether | 0.00928000 |
| 197. | 68738-94-3 | 2-Naphthalenecarboxaldehyde, octahydro-8,8-dimethyl | Cyclomyral ® | 0.00920000 |
| 198. | 2705-87-5 | Cyclohexanepropanoic acid, 2-propen-1-yl ester | Allyl Cyclohexane Propionate | 0.00925000 |
| 199. | 7011-83-8 | 2 (3H)-Furanone, 5-hexyldihydro-5-methyl- | Lactojasmone ® | 0.00885000 |
| 200. | 61792-11-8 | 2,6-Nonadienenitrile, 3,7-dimethyl- | Lemonile ® | 0.00884000 |
| 201. | 692-86-4 | 10-Undecenoic acid, ethyl ester | Ethyl Undecylenate | 0.00882000 |
| 202. | 103-95-7 | Benzenepropanal, α-methyl-4-(1-methylethyl)- | Cymal | 0.00881000 |
| 203. | 13019-22-2 | 9-Decen-1-ol | Rosalva | 0.00879000 |
| 204. | 94201-19-1 | 1-Oxaspiro[4.5]decan-2-one, 8-methyl- | Methyl Laitone 10% TEC | 0.00872000 |
| 205. | 104-61-0 | 2 (3H)-Furanone, dihydro-5-pentyl- | γ-Nonalactone | 0.00858000 |
| 206. | 706-14-9 | 2 (3H)-Furanone, 5-hexyldihydro- | γ-Decalactone | 0.00852000 |
| 207. | 24720-09-0 | 2-Buten-1-one, 1-(2,6,6-trimethyl-2-cyclohexen-1-yl)-, (2E)- | α-Damascone | 0.00830000 |
| 208. | 39872-57-6 | 2-Buten-1-one, 1-(2,4,4-trimethyl-2-cyclohexen-1-yl)-, (2E)- | Isodamascone | 0.00830000 |
| 209. | 705-86-2 | 2H-Pyran-2-one, tetrahydro-6-pentyl- | Decalactone | 0.00825000 |
| 210. | 67634-15-5 | Benzenepropanall, 4-ethyl-α,α-dimethyl- | Floralozone | 0.00808000 |
| 211. | 40527-42-2 | 1,3-Benzodioxole, 5-(diethoxymeth3,4)- | Heliotropin Diethyl Acetal | 0.00796000 |
| 212. | 56973-85-4 | 4-Penten-l-one, 1-(5,5-dimethyl-1-cyclohexen-1-yl)- | Neobutenone α | 0.00763000 |

TABLE 2A-continued

Moderate Volatile Fragrance Materials

| No. | CAS Number | IUPAC Name | Common Name** | Vapor Pressure (Torr at 25° C.)* |
|---|---|---|---|---|
| 213. | 128-51-8 | Bicyclo[3.1.1]hept-2-ene-2-ethanol, 6,6-dimethyl-, 2-acetate | Nopyl Acetate | 0.00751000 |
| 214. | 103-36-6 | 2-Propenoic acid, 3-phenyl-, ethyl ester | Ethyl Cinnamate | 0.00729000 |
| 215. | 5182-36-5 | 1,3-Dioxane, 2,4,6-trimethyl-4-phenyl- | Floropal ® | 0.00709000 |
| 216. | 42604-12-6 | Cyclododecane, methoxymethoxy)- | Boisambrene | 0.00686000 |
| 217. | 33885-52-8 | Bicyclo[3.1.1]hept-2-ene-2-propanal, α,α,6,6-tetramethyl- | Pinyl Iso Butyrate Alpha | 0.00685000 |
| 218. | 92015-65-1 | 2 (3H)-Benzofuranone, hexahydro-3,6-dimethyl- | Natactone | 0.00680000 |
| 219. | 63767-86-2 | Cyclohexanemethanol, α,-methyl-4-(1-methylethyl)- | Mugetanol | 0.00678000 |
| 220. | 3288-99-1 | Benzeneacetonitrile, 4-(1,1-dimethylethyl)- | Marenil CI | 0.00665000 |
| 221. | 35044-68-9 | 2-Buten-1-one, 1-(2,6,6-trimethyl-1-cyclohexen-1-yl)- | beta-Damascone | 0.00655000 |
| 222. | 41724-19-0 | 1,4-Methanonaphthalen-6 (2H)-one, octahydro-7-methyl | Plicatone | 0.00652000 |
| 223. | 75147-23-8 | Bicyclo[3.2.1]octan-8-one, 1,5-dimethyl-, omime | Buccoxime ® | 0.00647000 |
| 224. | 25634-93-9 | 2-Methyl 4-5-phenylpentan-1-ol | Rosaphen ® 600064 | 0.00637000 |
| 225. | 55066-48-3 | 3-Methyl-5-phenylpentanol | Phenyl Hexanol | 0.00637000 |
| 226. | 495-62-5 | Cyclohexene, 4-(1,5-dimethyl-4-hexen-1-ylidene)-1-methyl- | Bisabolene | 0.00630000 |
| 227. | 2785-87-7 | Phenol, 2-methoxy-4-propyl- | Dihydro Eugenol | 0.00624000 |
| 228. | 7-19-4 | Benzoic acid, 2-hydroxy-, 2-methylpropyl ester | Iso Butyl Salicylate | 0.00613000 |
| 229. | 4430-31-3 | 2H-1-Benzopyran-2-one, octahydro- | Octahydro Coumarin | 0.00586000 |
| 230. | 38462-22-5 | Cyclohexanone, 2-(1-mercapto-l-methylethyl)-5-methyl- | Ringonol 50 TEC | 0.00585000 |
| 231. | 77-83-8 | 2-Oxiranecarboxylic acid, 3-methyl-3-phenyl-, ethyl ester | Ethyl Methyl Phenyl Glycidate | 0.00571000 |
| 232. | 37677-14-8 | 3-Cyclohexene-1-carboxaldehyde, 4-(4-methyl-3-penten-1-yl)- | Iso Hexenyl Cyclohexenyl Carboxaldehyde | 0.00565000 |
| 233. | 103-60-6 | Propanoic acid, 2-methyl-, 2-phenoxyethyl ester | Phenoxy Ethyl iso-Butyrate | 0.00562000 |
| 234. | 18096-62-3 | Indeno[1,2-d]-1,3-dioxin, 4,4a,5,9b-tetrahydro- | Indoflor ® | 0.00557000 |
| 235. | 63500-71-0 | 2H-Pyran-4-ol, tetrahydro-4-methyl-2-(2-methylpropyl)- | Florosa Q/Florol | 0.00557000 |
| 236. | 65405-84-7 | Cyclohexanebutanal, α,2,6,6-tetramethyl- | Cetonal ® | 0.00533000 |
| 237. | 171102-41-3 | 4,7-Methano-1H-inden-6-ol, 3a,4,5,6,7,7a-hexahydro-8,8-dimethyl-, 6-acetate | Flor Acetate | 0.00530000 |

TABLE 2A-continued

Moderate Volatile Fragrance Materials

| No. | CAS Number | IUPAC Name | Common Name** | Vapor Pressure (Torr at 25° C.)* |
|---|---|---|---|---|
| 238. | 10339-55-6 | 1,6-Nonadien-3-61, 3,7-dimethyl- | Ethyl linalool | 0.00520000 |
| 239. | 23267-57-4 | 3-Buten-2-one, 4-(2,2,6-trimethyl-7-oxabicyclo[4.1.0]hept-1-yl)- | Ionone Epoxide Beta | 0.00520000 |
| 240. | 97-54-1 | Phenol, 2-methoxy-4-(1-propen-l-yl)- | Isoeugenol | 0.00519000 |
| 241. | 67663-01-8 | 2 (3H)-Furanone, 5-hexyldihydro-4-methyl- | Peacholide | 0.00512000 |
| 242. | 33885-52-8 | Bicyclo[3.1.1]hept-2-ene-2-propanal, α,α,6,6-tetramethyl- | Pinyl Iso Butyrate Alpha | 0.00512000 |
| 243. | 23696-85-7 | 2-Buten-1-one, 1-(2,6,6-trimethyl-1,3-cyclohexadien-1-yl)- | Damascenone | 0.00503000 |
| 244. | 80-71-7 | 2-Cyclopenten-1-one, 2-hydroxy-3-methyl- | Maple Lactone | 0.00484000 |
| 245. | 67662-96-8 | Propanoic acid, 2,2-dimethyl-, 2-phenylethyl ester | Pivarose Q | 0.00484000 |
| 246. | 2437-25-4 | Dodecanenitrile | Clonal | 0.00480000 |
| 247. | 141-14-0 | 6-Octen-1-ol, 3,7-dimethyl-, 1-propanoate | Citronelllyl Propionate | 0.00469000 |
| 248. | 54992-90-4 | 3-Buten-2-one, 4-(2,2,3,6-tetramethylcyclohexyl)- | Myrrhone | 0.00460000 |
| 249. | 55066-49-4 | Benzenepentanal, β-methyl- | Mefranal | 0.00455000 |
| 250. | 7493-74-5 | Acetic acid, 2-phenoxy-, 2-propen-1-yl ester | Allyl Phenoxy Acetate | 0.00454000 |
| 251. | 80-54-6 | Benzenepropanal, 4-(1,1-ditnethylethyl)-α-methyl- | Lilial ® | 0.00444000 |
| 252. | 86803-90-9 | 4,7-Methano-1H-indene-2-carboxaldehyde, octahydro-5-methoxy- | Scentenal ® | 0.00439000 |
| 253. | 68991-97-9 | 2-Naphthalenecarboxaldehyde, 1,2,3,4,5,6,7,8-octahydro-8,8-dimethyl- | Melafleur | 0.00436000 |
| 254. | 1887′1-14-2 | Pentitol, 1,5-anhydro-2,4-dideoxy-2-pentyl-, 3-acetate | Jasmal | 0.00434000 |
| 255. | 58567-11-6 | Cyclododecane, (ethoxymethoxy)- | Boisambren Forte | 0.00433000 |
| 256. | 94400-98-3 | Naphth[2,3-b]oxirene, 1a,2,3,4,5,6,6,7,7a-octahydro-1a,3,3,4,6,6-hexamethyl-, (1aR, 4S, 7aS)-rel- | Molaxone | 0.00425000 |
| 257. | 79-69-6 | 3-Buten-2-one, 4-(2,5,6,6-tetramethyl-2-cyclohexen-l-yl)- | alpha-Irone | 0.00419000 |
| 258. | 65442-31-1 | Quinoline, 6-(1-methylpropyl)- | Iso Butyl Quinoline | 0.00408000 |
| 259. | 87731-18-8 | Carbonic acid, 4-cycloocten-l-yl methyl ester | Violiff | 0.00401000 |
| 260. | 173445-65-3 | 1H-Indene-5-propanal, 2,3-dihydro-3,3-dimethyl- | Hivernal (A-isomer) | 0.00392000 |

TABLE 2A-continued

Moderate Volatile Fragrance Materials

| No. | CAS Number | IUPAC Name | Common Name** | Vapor Pressure (Torr at 25° C.)* |
|---|---|---|---|---|
| 261. | 23911-56-0 | Ethanone, 1-(3-methyl-2-benzofuranyl)- | Nerolione | 0.00383000 |
| 262. | 52474-60-9 | 3-Cyclohexene-1-carboxaldehyde, 1-methyl-3-(4-methyl-3-penten-1-yl)- | Precyclemone B | 0.00381000 |
| 263. | 139539-66-5 | 6-Oxabicyclo[3.2.1]octane, 5-methyl-1-(2,2,3-trimethyl-3-cyclopenten-1-yl)- | Cassifix | 0.00381000 |
| 264. | 80858-47-5 | Benzene, [2-(cyclohexyloxy)ethyl]- | Phenafleur | 0.00380000 |
| 265. | 32764-98-0 | 2H-Pyran-2-one, tetrahydro-6-(3-penten-1-yl)- | Jasmolactone | 0.00355000 |
| 266. | 78417-28-4 | 2,4,7-Decatrienoic acid, ethyl ester | Ethyl 2,4,7-decatrienoate | 0.00353000 |
| 267. | 140-26-1 | Butanoic acid, 3-methyl-, 2-phenylethyl ester | Beta Phenyl Ethyl Isovalerate | 0.00347000 |
| 268. | 105-90-8 | 2,6-Octadien-1-ol, 3,7-dimethyl-, 1-propanoate, (2E)- | Geranyl Propionate | 0.003360000 |
| 269. | 41816-03-9 | Spiro[1,4-methanonaphthalene-2(1H),2'-oxirane], 3,4,4a,5,8,8a-hexahydro-3',7-dimethyl- | Rhubofix ® | 0.00332000 |
| 270. | 7070-15-7 | Ethanol, 2-[[(1R, 2R, 4R)-1,7,7-trimethylbicyclo[2.2.1]hept-2-yl]oxy]-, rel- | Arbanol | 0.00326000 |
| 271. | 93-29-8 | Phenol, 2-methoxy-4-(1-propen-1-yl)-, 1-acetate | Iso Eugenol Acetate | 0.00324000 |
| 272. | 476332-65-7 | 2H-Indeno[4,5-b]furan, decahydro-2,2,6,6,7,8,8-heptamethyl- | Amber Xtreme Compound 1 | 0.00323000 |
| 273. | 68901-15-5 | Acetic acid, 2-(cyclohexyloxy)-, 2-propen-1-yl ester | Cyclogalbanate | 0.00323000 |
| 274. | 107-75-5 | Octanal, 7-hydroxy-3,7-dimethyl- | Hydroxycitronellal | 0.00318000 |
| 275. | 68611-23-4 | Naphtho[2,1-b]furan, 9b-ethyldodecahydro-3a,7,7-trimethyl- | Grisalva | 0.00305000 |
| 276. | 313973-37-4 | 1,6-Heptadien-3-one, 2-cyclohexyl- | Pharaone | 0.00298000 |
| 277. | 137-00-8 | 5-Thiazoleethanol, 4-methyl- | Sulfurol | 0.00297000 |
| 278. | 7779-30-8 | 1-Penten-3-one, 1-(2,6,6-trimethyl-2-cyclohexen-1-yl)- | Methyl Ionone | 0.00286000 |
| 279. | 127-51-5 | 3-Buten-2-one, 3-methyl-4-(2,6,6-trimethyl-2-cyclohexen-1-yl)- | Isoraldeine Pure | 0.00282000 |
| 280. | 72903-27-6 | 1,4-Cyclohexanedicarboxylic acid, 1,4-diethyl ester | Fructalate ™ | 0.00274000 |
| 281. | 7388-22-9 | 3-Buten-2-one, 4-(2,2-dimethyl-6-methylenecyclohexyl)-3-methyl- | Ionone Gamma Methyl | 0.00272000 |

TABLE 2A-continued

Moderate Volatile Fragrance Materials

| No. | CAS Number | IUPAC Name | Common Name** | Vapor Pressure (Torr at 25° C.)* |
|---|---|---|---|---|
| 282. | 104-67-6 | 2(3H)-Furanone, 5-heptyldihydro- | gamma-Undecalactone (racemic) | 0.00271000 |
| 283. | 1205-17-0 | 1,3-Benzodioxole-5-propanal, α-methyl- | Helional | 0.00270000 |
| 284. | 33704-61-9 | 4H-Inden-4-one, 1,2,3,5,6,7-hexahydro-1,1,2,3,3-pentatnethyl- | Cashmeran | 0.00269000 |
| 285. | 36306-87-3 | Cyclohexanone, 4-(1-ethoxyethenyl)-3,3,5,5-tetramethyl- | Kephalis | 0.00269000 |
| 286. | 97384-48-0 | Benzenepropanenitrile, α-ethenyl-α-methyl- | Citrowane ® B | 0.00265000 |
| 287. | 141-13-9 | 9-Undecenal, 2,6,10-trimethyl- | Adoxal | 0.00257000 |
| 288. | 2110-18-1 | Pyridine, 2-(3-phenylpropyl)- | Corps Racine VS | 0.00257000 |
| 289. | 27606-09-3 | Indeno[1,2-d]-1,3-dioxin, 4,4a,5,9b-tetrahydro-2,4-dimethyl- | Magnolan | 0.00251000 |
| 290. | 67634-20-2 | Propanoic acid, 2-methyl-, 3a,4,5,6,7,7a-hexahydro-4,7-methano-1H-inden-5-yl ester | Cyclabute | 0.00244000 |
| 291. | 65405-72-3 | 1-Naphthalenol, 1,2,3,4,4a,7,8,8a-octahydro-2,4a,5,8a-tetramethyl-, 1-formate | Oxyoctaline Formate | 0.00236000 |
| 292. | 122-40-7 | Heptanal, 2-(phenylmethylene)- | Amyl Cinnamic Aldehyde | 0.00233000 |
| 293. | 103694-68-4 | Benzenepropanol, β,β,3-trimethyl- | Majantol ® | 0.00224000 |
| 294. | 13215-88-8 | 2-Cyclohexen-1-one, 4-(2-buten-1-ylidene)-3,5,5-trimethyl- | Tabanone Coeur | 0.00223000 |
| 295. | 25152-85-6 | 3-Bexen-l-ol, 1-benzoate, (3Z)- | Cis-3-Bexenyl Benzoate | 0.00203000 |
| 296. | 406488-30-0 | 2-Ethyl-N-methyl-N-(m-tolyl) butanamide | Paradisamide | 0.00200000 |
| 297. | 121-33-5 | Benzaldehyde, 4-hydroxy-3-methoxy- | Vanillin | 0.00194000 |
| 298. | 77-54-3 | 1H-3a,7-Methanoazulen-6-ol, octahydro-3,6,8,8-tetramethyl-, 6-acetate, (3R, 3aS, 6R, 7R, 8aS)- | Cedac | 0.00192000 |
| 299. | 76842-49-4 | 4,7-Methano-1H-inden-6-ol, 3a,4,5,6,7,7a-hexahydro-8,8-dimethyl-, 6-propanoate | Frutene | 0.00184000 |
| 300. | 121-39-1 | 2-Oxiranecarboxylic acid, 3-phenyl-, ethyl ester | Ethyl Phenyl Citycidate | 0.00184000 |
| 301. | 11299-54-6 | 4H-4a,9-Methanoazuleno[5,6-d]-1,3-dioxole octahydro-2,2,5,8,8,9a-hexatnethyl-, (4aR, 5R, 7aS, 9R)- | Ambrocenide ® | 0.00182000 |
| 302. | 285977-85-7 | (2,5-Dimethyl-1,3-dihydroinden-2-yl)methanol | Lilyflore | 0.00180000 |

TABLE 2A-continued

Moderate Volatile Fragrance Materials

| No. | CAS Number | IUPAC Name | Common Name** | Vapor Pressure (Torr at 25° C.)* |
|---|---|---|---|---|
| 303. | 10094-34-5 | Butanoic acid, 1,1-dimethyl-2-phenylethyl ester | Diniethyl Benzyl Carbinyl Butyrate | 0.00168000 |
| 304. | 40785-62-4 | Cyclododeca[c]furan, 1,3,3a,4,5,6,7 8,9,10,11,13a-dodecahydro- | Muscogene | 0.00163000 |
| 305. | 75490-39-0 | Benzenebutanenitrile, α,α,γ-trimethyl- | Khusinil | 0.00162000 |
| 306. | 55418-52-5 | 2-Butanone, 4-(1,3-benzodioxo1-5-yl)- | Dulcinyl | 0.00161000 |
| 307. | 3943-74-6 | Benzoic acid, 4-hydroxy-3-methoxy-, methyl ester | Carnaline | 0.00157000 |
| 308. | 72089-08-8 | 3-Cyclopentene-1-butanol, β,2,2,3-tetramethyl- 2-Methyl-4-(2,2,3-trimethyl-3-cyclopenten-1-yl)butanol | Brahmanol ® | 0.00154000 |
| 309. | 3155-71-3 | 2-Butenal, 2-methyl-4-(2,6,6-trimethyl-1-cyclohexen-1-yl)- | Boronal | 0.00147000 |
| 310. | 2050-08-0 | Benzoic acid, 2-hydroxy-, pentyl ester | Amyl Salicylate | 0.00144000 |
| 311. | 41199-20-6 | 2-Naphthalenol, decahydro-2,5,5-trimethyl- | Ambrinol | 0.00140000 |
| 312. | 12262-03-2 | ndecanoic acid, 3-methylbutyl ester | Iso Amyl Undecylenate | 0.00140000 |
| 313. | 107-74-4 | 1,7-Octanediol, 3,7-dimethyl- | Hydroxyol | 0.00139000 |
| 314. | 91-64-5 | 2H-1-Benzopyran-2-one | Coumarin | 0.00130000 |
| 315. | 68901-32-6 | 1,3-Dioxolane, 2-[6-methyl-8-(1-methylethyl)bicyclo[2.2.2]oct-5-en-2-yl]- | Glycolierral | 0.00121000 |
| 316. | 68039-44-1 | Propanoic acid, 2,2-dimethyl-, 3a,4,5,6,7,7a-hexahydro-4,7-methano-1H-inden-6-yl ester | Piyacyclene | 0.00119000 |
| 317. | 106-29-6 | Butanoic acid, (2E)-3,7-dimethyl-2,6-octadien-1-yl ester | Geranyl Butyrate | 0.00116000 |
| 318. | 5471-51-2 | 2-Butanone, 4-(4-hydroxyphenyl)- | Raspberry ketone | 0.00106000 |
| 319. | 109-42-2 | 10-Undecenoic acid, butyl ester | Butyl Undecylenate | 0.00104000 |
| 320. | 2785-89-9 | 4-Ethyl-2-methoxyphenol | 4-Ethylguaiacol | 0.02000000 |
| 321. | 27538-10-9 | 2-ethyl-4-hydroxy-5-methylfuran-3-one | Homofuronol | 0.01210000 |

*Vapor Pressures are acquired as described in the Test Methods Section.
**Origin: Same as for Table 1 hereinabove.

TABLE 2B

Moderate Volatile Natural Oils.

| No. | Natural oil | Supplier |
|---|---|---|
| 1. | Bay Oil Terpeneless | IFF |
| 2. | Cade Oil | H. Reynaud & Fils |
| 3. | Cedar Atlas Oil | Robertet |
| 4. | Cinnamon Bark Oil | Robertet |
| 5. | Cinnamon Oleoresin | Citrus & Allied Essences |
| 6. | Clove Bud Oil | Robertet |
| 7. | Clove Leaf Oil Rectified | H. Reynaud & Fils |
| 8. | Clove Stem Oil | H. Reynaud & Fils |
| 9. | Davana Oil | Robertet |
| 10. | Geranium Bourbon | Robertet |
| 11. | Ginger Oil Fresh Madagascar | IFF |
| 12. | Hay Absolute MD 50 PCT | IFF |

TABLE 2B-continued

Moderate Volatile Natural Oils.

| No. | Natural oil | Supplier |
|---|---|---|
| 13. | Juniperberry Oil T'less | Robertet |
| 14. | Papyrus Oil | Robertet |
| 15. | Rose Absolute Oil | Robertet |
| 16. | Tonka Bean Absolute | Robertet |
| 17. | Wormwood Oil | Robertet |

Suppliers:
Citrus & Allied Essences, New York, USAH. Reynaud & Fils, Montbrun-les-Bains, France IFF, Hazlet, New Jersey, USA
Robertet, Grasse, France Moderate volatile fragrance materials can be selected from the group of Tables 2A or 2B. However, it is understood by one skilled in the art that other moderate volatile fragrance materials, not recited in Tables 2A or 2B, would also fall within the scope of the present invention, so long as they have a vapor pressure of 0.1 to 0.001 Torr at 25° C.

(iii) High Volatile Fragrance Materials

The fragrance component includes at least one high volatile fragrance material having a vapor pressure greater than 0.1 Torr (0.0133 kPa) at 25° C. In some examples, the high volatile fragrance material can include at least 2 high volatile fragrance materials, 3 high volatile fragrance materials, or at least 5 high volatile fragrance materials, or at least 7 high volatile fragrance materials. In some examples, the high volatile fragrance material can be present in an amount ranging from about 0.1 wt % to about 30 wt % of the fragrance component, about 1 wt % to about 30 wt %, about 5 wt % to about 30 wt %, or less than, equal to, or greater than about 0.1 wt %, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.25, 27, 27.5, 28, 28.5, 29, 29.5, or about 30 wt %. If there are more than one high volatile fragrance materials, then the ranges provided hereinabove cover the total of all of the high volatile fragrance materials. Suitable examples of high volatile fragrances materials are provided in Tables 3A and 3B below.

Preferably, the high volatile fragrance material is selected from at least 1 material, or at least 2 materials, or at least 3 materials, or at least 5 materials, at least 7 materials, or at least 9 high volatile fragrance materials as disclosed in Table 3A. Natural fragrance materials or oils having an aggregate vapour pressure greater than 0.1 Torr (0.0133 kPa) at 25° C. are provided in Table 3B. Moderate Volatile Natural Oils.

TABLE 3A

High Volatile Fragrance Materials

| No. | CAS Number | IUPAC Name | Common Name** | Vapor Pressure (Torr at 25° C.)* |
|---|---|---|---|---|
| 1. | 107-31-3 | Formic acid, methyl ester | Methyl Formate | 732.00000000 |
| 2. | 75-18-3 | Methane, 1,1'-thiobis- | Dimethyl Sulfide 1.0% In DEP | 647.00000000 |
| 3. | 141-7-6 | Acetic acid ethyl ester | Ethyl Acetate | 112.00000000 |
| 4. | 105-37-3 | Propanoic acid, ethyl ester | Ethyl Propionate | 44.50000000 |
| 5. | 110-19-0 | Acetic acid, 2-methylpropyl ester | Isobutyl Acetate | 18.00000000 |
| 6. | 105-54-4 | Butanoic acid, ethyl ester | Ethyl Butyrate | 13.90000000 |
| 7. | 14765-30-1 | 1-Butanol | Butyl Alcohol | 8.52000000 |
| 8. | 7452-79-1 | Butanoic acid, 2-methyl-, ethyl ester | Ethyl-2-Methyl Butyrate | 7.85000000 |
| 9. | 123-97-2 | 1-Butanol, 3-methyl-, 1-acetate | Iso Amyl Acetate | 5.68000000 |
| 10. | 66576-71-4 | Butanoic acid, 2-methyl-, 1-methylethyl ester | Iso Propyl 2-Methylbutyrate | 5.10000000 |
| 11. | 110-43-0 | 2-Heptanone | Methyl Amyl Ketone | 4.73000000 |
| 12. | 6728-26-3 | 2-Hexenal, (2E)- | Trans-2 Hexenal | 4.62000000 |
| 13. | 123-51-3 | 1-Butanol, 3-methyl- | Isoamyl Alcohol | 4.16000000 |
| 14. | 1191-16-8 | 2-Buten-1-ol, 3-methyl-, 1-acetate | Prenyl acetate | 3.99000000 |
| 15. | 57366-77-5 | 1,3-Dioxolane-2-methanamine, N-methyl- | Methyl Dioxolan | 3.88000000 |
| 16. | 7785-70-8 | Bicyclo[3.1.1]hept-2-ene, 2,6,6-trimethyl-, (1R, 5R)- | Alpha Pinene | 3.49000000 |

TABLE 3A-continued

High Volatile Fragrance Materials

| No. | CAS Number | IUPAC Name | Common Name** | Vapor Pressure (Torr at 25° C.)* |
|---|---|---|---|---|
| 17. | 79-92-5 | Bicyclo[2.2.1]heptane, 2,2-dimethyl-3-methylene- | Camphene | 3.38000000 |
| 18. | 94087-83-9 | 2-Butanethiol, 4-methoxy-2-methyl- | 4-Methoxy-2-Methyl-2-Butanenthiol | 3.31000000 |
| 19. | 39255-32-8 | Pentanoic acid, 2-methyl-, ethyl ester | Manzanate | 2.91000000 |
| 20. | 3387-41-5 | Bicyclo[3.1.0]hexane, 4-methylene-1-(1-methylethyl)- | Sabinene | 2.63000000 |
| 21. | 127-91-3 | Bicyclo[3.1.1]heptane, 6,6-dimethyl-2-methylene- | Beta Pinene | 2.40000000 |
| 22. | 105-68-0 | 1-Butanol, 3-methyl-, 1-propanoate | Amyl Propionate | 2.36000000 |
| 23. | 123-35-3 | 1,6-Octadiene, 7-methyl-3-methylene- | Myrcene | 2.29000000 |
| 24. | 124-13-0 | Octa,nal | Octyl Aldehyde | 2.07000000 |
| 25. | 7392-19-0 | 2H-Pyran, 2-ethenyltetrahydro-2,6,6-trimethyl- | Limetol | 1.90000000 |
| 26. | 111-13-7 | 2-Octanone | Methyl Hexyl Ketone | 1.72000000 |
| 27. | 123-66-0 | Hexanoic acid, ethyl ester | Ethyl Caproate | 1.66000000 |
| 28. | 470-82-6 | 2-Oxabicyclo[2.2.2]octane, 1,3,3-trimethyl- | Eucalyptol | 1.65000000 |
| 29. | 99-87-6 | Benzene, 1-methyl-4-(1-methylethyl)- | Para Cymene | 1.65000000 |
| 30. | 104-93-8 | Benzene, 1-methoxy-4-methyl- | Para Cresyl Methyl Ether | 1.65000000 |
| 31. | 13877-91-3 | 1,3,6-Octatriene, 3,7-dimethyl- | Ocimene | 1.56000000 |
| 32. | 138-86-3 | Cyclohexene, 1-methyl-4-(1-methylethenyl)- | dl-Limonene | 1.54000000 |
| 33. | 5989-27-5 | Cyclohexene, 1-methyl-4-(1-methylethenyl)-, (4R)- | d-limonene | 1.54000000 |
| 34. | 106-68-3 | 3-Octanone | Ethyl Amyl Ketone | 1.50000000 |
| 35. | 110-41-8 | Undecanall, 2-methyl- | Methyl Nonyl Acetaldehyde | 1.43000000 |
| 36. | 142-92-7 | Acetic acid, hexyl ester | Hexyl acetate | 1.39000000 |
| 37. | 110-93-0 | 5-Hepten-2-one, 6-methyl- | Methyl Heptenone | 1.28000000 |
| 38. | 81925-81-7 | 2-Hepten-4-one, 5-methyl- | Filbertone 1% in TEC | 1.25000000 |
| 39. | 3681-71-8 | 3-Hexen-1-ol, 1-acetate, (3Z)- | cis-3-Hexenyl acetate | 1.22000000 |
| 40. | 97-64-3 | .Propanoic acid, 2-hydroxy-, ethyl ester | Ethyl Lactate | 1.16000000 |
| 41. | 586-62-9 | Cyclohexene, 1-methyl-4-(1-methylethylidene)- | Terpineolene | 1.13000000 |
| 42. | 5115-64-1 | Butanoic acid, 2-methylbutyl ester | Amyl butyrate | 1.09000000 |

TABLE 3A-continued

High Volatile Fragrance Materials

| No. | CAS Number | IUPAC Name | Common Name** | Vapor Pressure (Torr at 25° C.)* |
|---|---|---|---|---|
| 43. | 106-27-4 | Butanoic acid, 3-methylbutyl ester | Amyl Butyrate | 1.09000000 |
| 44. | 99-85-4 | 1,4-Cyclohexadiene, 1-methyl-4-(1-methylethyl)- | Gamma Terpinene | 1.08000000 |
| 45. | 18640-74-9 | Thiazole, 2-(2-methylpropyl)- | 2-Isobutylthiazole | 1.07000000 |
| 46. | 928-96-1 | 3-Hexen-1-ol, (3Z)- | cis-3-Hexenol | 1.04000000 |
| 47. | 100-52-7 | Benzaldehyde | Benzaldehyde | 0.97400000 |
| 48. | 141-97-9 | Butanoic acid, 3-oxo-, ethyl ester | Ethyl Acetoacetate | 0.89000000 |
| 49. | 928-95-0 | 2-Hexen-1-ol, (2E)- | Trans-2-Hexenol | 0.87300000 |
| 50. | 928-94-9 | 2-Hexen-1-ol, (2Z)- | Beta Gamma Hexenol | 0.87300000 |
| 51. | 24691-15-4 | Cyclohexane, 3-ethoxy-1,1,5-trimethyl-, cis- (9CI) | Herbavert | 0.85200000 |
| 52. | 19872-52-7 | 2-Pentanone, 4-mercapto-4-methyl- | 4-Methyl-4-Mercaptopentan-2-one 1 ppm TEC | 0.84300000 |
| 53. | 3016-19-1 | 2,4,6-Octatriene, 2,6-dimethyl-, (4E, 6E)- | Allo-Ocimene | 0.81600000 |
| 54. | 69103-20-4 | Oxirane, 2,2-dimethyl-343-methyl-2,4-pentadien-1-yl)- | Myroxide | 0.80600000 |
| 55. | 189440-77-5 | 4,7-Octadienoic acid, methyl ester, (4E)- | Anapear | 0.77700000 |
| 56. | 67633-96-9 | Carbonic acid, (3Z)-3-hexen-1-yl methyl ester | Liffarom ™ | 0.72100000 |
| 57. | 123-68-2. | Hexanoic acid, 2-propen-1-yl ester | Allyl Caproate | 0.67800000 |
| 58. | 106-72-9 | 5-Heptenal, 2,6-dimethyl- | Melonal | 0.62200000 |
| 59. | 106-30-9 | Heptanoic acid, ethyl ester | Ethyl Oenanthate | 0.60200000 |
| 60. | 68039-49-6 | 3-Cyclohexene-1-carboxaldehyde, 4-dimethyl- | Ligustral or Triplal | 0.57800000 |
| 61. | 101-48-4 | Benzene, (2,2-dimethoxyethyl)- | Phenyl Acetaldehyde Dimethyl Acetal | 0.55600000 |
| 62. | 16409-43-1 | 2H-Pyran, tetrahydro-4-methyl-2-(2-methyl-1-propen-1-yl)- | Rose Oxide | 0.55100000 |
| 63. | 925-78-0 | 3-Nonanone | Ethyl Hexyl Ketone | 0.55100000 |
| 64. | 100-47-0 | Benzonitrile | Benzyl Nitrile | 0.52400000 |
| 65. | 589-98-0 | 3-Octanol | Octanol-3 | 0.51200000 |
| 66. | 58430-94-7 | 1-Hexanol, 3,5,5-trimethyl-, 1-acetate | Iso Nonyl Acetate | 0.47000000 |
| 67. | 10250-45-0 | 4-Heptanol, 2,6-dimethyl-, 4-acetate | Alicate | 0.45400000 |
| 68. | 105-79-3 | Hexanoic acid, 2-methylpropyl ester | Iso Butyl Caproate | 0.41300000 |
| 69. | 2349-07-7 | Propanoic acid, 2-methyl-, hexyl ester | Hexyl isobutyrate | 0.41300000 |

TABLE 3A-continued

High Volatile Fragrance Materials

| No. | CAS Number | IUPAC Name | Common Name** | Vapor Pressure (Torr at 25° C.)* |
|---|---|---|---|---|
| 70. | 23250-42-2 | Cyclohexanecarboxylic acid, 1,4-dimethyl-, methyl ester, trans- | Cyprissate | 0.40500000 |
| 71. | 122-78-1 | Benzeneacetaldehyde | Phenyl acetaldehyde | 0.36800000 |
| 72. | 5405-41-4 | Butanoic acid, 3-hydroxy-, ethyl ester | Ethyl-3-Hydroxy Butyrate | 0.36200000 |
| 73. | 105-51-3 | Propanedioic acid, 1,3-diethyl ester | Diethyl Malonate | 0.34400000 |
| 74. | 93-58-3 | Benzoic acid, methyl ester | Methyl Benzoate | 0.34000000 |
| 75. | 16356-11-9 | 1,3,5-Undecatriene | Undecatriene | 0.33600000 |
| 76. | 65405-70-1 | 4-Decenal, (4E)- | Decenal (Trans-4) | 0.33100000 |
| 77. | 54546-26-8 | 1,3-Dioxane, 2-butyl-4,4,6-trimethyl- | Herboxane | 0.33000000 |
| 78. | 13254-34-7 | 2-Heptanol,2,6-dimethyl- | Dimethyl-2 6-Heptan-2-ol | 0.33000000 |
| 79. | 98-86-2. | Ethanone, 1-phenyl- | Acetophenone | 0.29900000 |
| 80. | 93-53-8 | Benzeneacetaldehyde, α-methyl- | Hydratropic aldehyde | 0.29400000 |
| 81. | 80118-06-5 | Propanoic acid, 2-methyl-, 1,3-dimethyl-3-buten-1-yl ester | Iso Pentyrate | 0.28500000 |
| 82. | 557-48-2 | 2,6-Nonadienal, (2E, 6Z)- | E Z-2,6-Nonadien-1-al | 0.28000000 |
| 83. | 24683-00-9 | Pyrazine, 2-methoxy-3-(2-methylpropyl)- | 2-Methoxy-3-Isobutyl Pyrazine | 0.27300000 |
| 84. | 104-57-4 | Formic acid, phenylmethyl ester | Benzyl Formate | 0.27300000 |
| 85. | 104-45-0 | Benzene, 1-methoxy-4-propyl- | Dihydroanethole | 0.26600000 |
| 86. | 491-07-6 | Cyclohexanone, 5-methyl-2-(1-methylethyl)-, (2R,5R)-rel- | Iso Menthone | 0.25600000 |
| 87. | 89-80-5 | Cyclohexanone, 5-methyl-2-(1-methylethyl)-, (2R, 5S)-rel- | Menthone Racemic | 0.25600000 |
| 88. | 2463-53-8 | 2-Nonenal | 2 Nonen-1-al | 0.25600000 |
| 89. | 55739-89-4 | Cyclohexanone, 2-ethyl-4, 4-dimethyl- | Thuyacetone | 0.25000000 |
| 90. | 150-78-7 | Benzene, 1,4-dimethoxy- | Hydroquinone Dimethyl Ether | 0.25000000 |
| 91. | 64988-06-3 | Benzene, 1-(ethoxymethyl)-2-methoxy- | Rosacene | 0.24600000 |
| 92. | 76-27-7 | Bicyclo[2,2.1] heptan-2-one, 1,7,7-trimethyl- | Camphor gum | 0.22500000 |
| 93. | 67674-46-8 | 2-Hexene, 6, 6-dimethoxy-2.5, 5-trimethyl- | Methyl Pamplemousse | 0.21400000 |
| 94. | 112-31-2 | Decanal | Decyl Aldehyde | 0.20700000 |
| 95. | 16251-77-7 | Benzenepropanal, β-methyl- | Trifernal | 0.20600000 |
| 96 | 93-92-5 | Benzenemethanol, α-methyl-, 1-acetate | Methylphenylcarbinol Acetate | 0.20300000 |

TABLE 3A-continued

High Volatile Fragrance Materials

| No. | CAS Number | IUPAC Name | Common Name** | Vapor Pressure (Torr at 25° C.)* |
|---|---|---|---|---|
| 97. | 143-13-5 | Acetic acid, nonyl ester | Nonyl Acetate | 0.19700000 |
| 98. | 122-00-9 | Ethanone, 1-(4-methylphenyl)- | Para Methyl Acetophenone | 0.18700000 |
| 99. | 24237-00-1 | 2H-Pyran, 6-butyl-3, 6-dihydro-2, 4-dimethyl- | Gyrane | 0.18600000 |
| 100. | 41519-23-7 | Propanoic acid, 2-methyl-, (3Z)-3-hexen-1-yl ester | Hexenyl Isobutyrate | 0.18200000 |
| 101. | 93-89-0 | Benzoic acid, ethyl ester | Ethyl Benzoate | 0.18000000 |
| 102. | 20780-48-7 | 3-Octanol, 3,7-dimethyl-, 3-acetate | Tetrahydro Linalyl Acetate | 0.18000000 |
| 103. | 101-41-7 | Methyl 2-phenylacetate | Methylphenyl acetate | 0.17600000 |
| 104. | 40853-55-2 | 1-Hexanol, 5-methyl-2-(1-methylethyl)-, 1-acetate | Tetrahydro Lavandulyl Acetate | 0.17300000 |
| 105. | 933-48-2. | Cyclohexanol, 3,3,5-trimethyl-, (1R, 5R)-rel- | Trimethylcyclohexanol | 0.17300000 |
| 106. | 35158-25-9 | 2-Hexenal, 5-methyl-2-(1-methylethyl)- | Lactone of Cis Jasmone | 0.17200000 |
| 107. | 18479-58-8 | 7-Octen-2-ol, 2,6-dimethyl- | Dihydromyrcenol | 0.16600000 |
| 108. | 140-11-4 | Acetic acid, phenylmethyl ester | Benzyl acetate | 0.16400000 |
| 109. | 14765-30-1 | Cyclohexanone; 2-(1-methylpropyl)- | 2-sec-Butyl Cyclo Hexanone | 0.16300000 |
| 110. | 20125-84-2 | 3-Octen-1-ol, (3Z)- | Octenol | 0.16000000 |
| 111. | 142-19-8 | Heptanoic acid, 2-propen-1-yl ester | Allyl Heptoate | 0.16000000 |
| 112. | 100-51-6 | Benzenemethanol | Benzyl Alcohol | 0.15800000 |
| 113. | 10032-15-2 | Butanoic acid, 2-methyl-, hexyl ester | Hexyl-2-Methyl Butyrate | 0.15800000 |
| 114. | 695-06-7 | 2(3H)-Furanone, 5-ethyldihydro- | Gamma Hexalactone | 0.15200000 |
| 115. | 21722-83-8 | Cyclohexaneethanol, 1-acetate | Cyclohexyl Ethyl Acetate | 0.15200000 |
| 116. | 111-79-5 | 2-Nonenoic acid, methyl ester | Methyl-2-Nonenoate | 0.14600000 |
| 117. | 16491-36-4 | Butanoic acid, (3Z)-3-hexen-1-yl ester | Cis 3 Hexenyl Butyrate | 0.13500000 |
| 118. | 111-12-6 | 2-Octynoic acid, methyl ester | Methyl Heptine Carbonate | 0.12500000 |
| 119. | 59323-76-1 | 1,3-Oxathiane, 2-methyl-4-propyl-, (2R, 4S)-rel- | Oxane | 0.12300000 |
| 120. | 62439-41-2 | Heptanal, 6-methoxy-2,6-dimethyl- | Methoxy Melonal | 0.11900000 |
| 121. | 13851-11-1 | Bicyclo+2,2.1+heptan-2-ol, 1,3,3-trime hyl-, 2-acetate | Fenchyl Acetate | 0.11700000 |
| 122. | 115-95-7 | 1,6-Octadien-3-ol, 3,7-dimethyl-, 3-acetate | Linalyl acetate | 0.11600000 |
| 123. | 18479-57-7 | 2-Octanol, 2,6-dimethyl- | Tetra-Hydro Myrcenol | 0.11500000 |
| 124. | 78-69-3 | 3,7-dimethyloctan-3-ol | Tetra-Hydro Linalool | 0.11500000 |

TABLE 3A-continued

High Volatile Fragrance Materials

| No. | CAS Number | IUPAC Name | Common Name** | Vapor Pressure (Torr at 25° C.)* |
|---|---|---|---|---|
| 125. | 111-87-5 | 1-Octanol | Octyl Alcohol | 0.11400000 |
| 126. | 71159-90-5 | 3-Cyclohexene-1-methanethiol, α,α,4-trimethyl- | Grapefruit mercaptan | 0.10500000 |
| 127. | 80-25-1 | Cyclohexanernethanol, α,α,4-trimethyl-, 1-acetate | Menthanyl Acetate | 0.10300000 |
| 128. | 88-41-5 | Cyclohexanol, 2-(1,1-dimethylethyl)-, 1-acetate | Verdox ™ | 0.10300000 |
| 129. | 32210-23-4 | Cyclohexanol, 4-(1,1-dimethylethyl)-, 1-acetate | Vertenex | 0.10300000 |
| 130. | 112-44-7 | Undecanal | n-Undecanal | 0.10200000 |
| 131. | 124-19-6 | Nonanal | Nonanal Aldehyde C-9 | 0.53200000 |
| 132. | 929253-05-4 | 6-methoxy-2,6-dimethyloctanal | 6-methoxy-2,6-dimethyl octanal | 0.04020000 |
| 133. | 68039-47-4 | 2-propan-2-yloxyethylbenzene | Phenethyl Isopropyl Ether | 0.24900000 |
| 134. | 6413-10-1 | ethyl 2-(2-methyl-1,3-dioxolan-2-yl)acetate | Apple Ketal | 0.21900000 |
| 135. | 106-23-0 | 3,7-dimethyloct-6-enal | citronellal | 0.21500000 |
| 136. | 14667-55-1 | Trimethyl Pyrazine-2,3,5 | Trimethyl Pyrazine-2,3,5 | 1.72400000 |

*Vapor Pressures are acquired as described in the Test Methods Section.
**Origin: Same as for Table 1 hereinabove.

TABLE 3B

High Volatile Fragrance Materials

| No. | Natural oil | Supplier |
|---|---|---|
| 1. | Angelica Seeds Oil | Robertet |
| 2. | Basil Oil Grand Vert | IFF |
| 3. | Bergamot Oil Reggio Early New Crop | Capua |
| 4. | Black Pepper Oil | Robertet |
| 5. | Blackcurrant Buds Absolute | Robertet |
| 6. | Cardamom Guatamala Extract CO2 | IFF |
| 7. | Cardamom Oil Guatemala | IFF |
| 8. | Cedarleaf Oil | Kerry |
| 9. | citronella oil | H. Reynaud & Fils |
| 10. | Claiy Sage Oil French | IFF |
| 11. | Coffee Extract CO2 | Firmenich |
| 12. | Cucumber Extract | Firmenich |
| 13. | Cumin Oil | Robertet |
| 14. | Cypress Oil | IFF |
| 15. | Elemi Coeur Oil | Robertet |
| 16. | Ginger oil India | IFF |
| 17. | Grapefruit Zest | Citrus & Allied Essences |
| 18. | It. Bergamot Oil | Capua |
| 19. | Labdanum Cistus Absolute | Biolandes |
| 20. | Lavandin Grosso Oil | H. Reynaud & Fils |
| 21. | Lemon Oil Winter | Capua |
| 22. | Green Mandarin Oil | Simone Gatto |
| 23. | Nutmeg Oil | Robertet |
| 24. | Oil Orange Sinensal | Citrus & Allied Essences |
| 25. | Olibanum Oil Pyrogenous | Firmenich |
| 76. | Pepper Black CO2 Oil | Firmenich |
| 27. | Petitgrain Mandarinier Oil | Misitano & Stracuzzi |
| 28. | Pink Pepper CO2 OIL | Firmenich |
| 29. | Rum CO2 Oil | Firmenich |
| 30. | Sichuan Pepper CO2 oil | Firmenich |
| 31. | Styrax Resoid | IFF |
| 32. | Tangerine Oil | Robertet |
| 33. | Thym Oil | IFF |
| 34. | Violet Leaves Absolute | Robertet |

Suppliers
Biolandes, Le Sen, France
Capua, Campo Calabro, Italy
Citrus & Allied Essences, New York, USA
Firmenich, Geneva, Switzerland
Global Essence Inc, New Jersey, USA
H. Reynaud & Fils, Montbrun-les-Bains, France
IFF, Hazlet, New Jersey, USA
Kerry, Co. Kerry, Ireland
Mane, Le Bar-sur-Loup, France
Misitano & Stracuzzi, Messina, Italy
Robertet, Grasse, France
Simone Gatto, San Pierre Niceto, Italy Exemplary high volatile fragrance materials selected from the group of Tables 3A or 3B are preferred. However, it is understood by one skilled in the art that other high volatile fragrance materials, not recited in Tables 3A or 3B, would also fall within the scope of the present invention, so long as they have a vapor pressure of greater than 0.1 Torr (0.0133 kPa) at 25° C.

(iv) Fragrance Modulators

The composition further comprises at least one substantially non-odorous fragrance modulator as described herein below. Suitable examples of the substantially non-odorous fragrance modulators are provided in Table 4 below.

The substantially non-odorous fragrance modulator can be present in an amount of from about 0.1 wt % to about 20 wt % relative to the total weight of the composition of the composition, about 0.5 wt % to about 18 wt %, about 2.5 wt % to about 15 wt %, or less than, equal to, or greater than about 0.1 wt %, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20 wt %. If there are more than one substantially non-odorous fragrance modulators, then the ranges provided hereinabove cover the total of all of the substantially non-odorous fragrance modulators.

The substantially non-odorous fragrance modulator can be a liquid at temperatures lower than 100° C., such as at ambient temperature. The substantially non-odorous fragrance modulators may be fully miscible with the fragrance materials to form a single phase liquid. However, if the fragrance materials are not entirely miscible, or are immiscible, then co-solvents (e.g., dipropylene glycol (DPG), triethyl citrate, or others well known to those skilled in the art) can be added to aid in the solubility of the fragrance materials.

According to various examples, the effect of the substantially non-odorous fragrance modulator on the fragrance profile, particularly the characters of the fragrance profile which is attributable to the low and high volatile fragrance materials, can be improved. By "improved" it is meant that the fragrance profile of the composition, particular the components contributed by at least one of the low and high volatile fragrance materials, can be perceived by the panel of experts or professional evaluators or individual experts or professional evaluators at later time points such as, for example, 1 hour, 2 hours, 3 hours, 4 hours, 5 hours, 6 hours, 7 hours, 8 hours, 10 hours, and possibly all the way up to 24 hrs after application as compared to controls, e.g., lacking any of the disclosed non-odorous fragrance modulators such as Glucam.

By "improved" it can mean that the perception by the panel of experts or professional evaluators or individual experts or professional evaluators, of a harshness of the composition being loaded with greater than 30 wt % of the low-fragrance material is reduced or eliminated.

Suitable examples of non-odorous modulators can include methyl glucoside polyol, ethyl glucoside polyol, propyl glucoside polyol, or mixtures thereof. Further examples can include from polypropylene glycol-10 methyl glucose ether, ethoxylated methyl glucose ether, polypropylene glycol-20 methyl glucose ether, caprylyl/capryl glucoside, undecyl glucoside, and mixtures thereof. In some examples, the composition can be substantially free of isocetyl alcohol, diisobutyl adipate, diisoamyl adipate, polypropylene glycol-3 myristyl ether, and neopentyl glycol diethyl hexanoate, neopentyl glycol diisononanoate, cetearyl ethyl hexanoate, and their mixtures, or a mixture thereof, although the composition can optionally include these.

Further examples of non-odorous modulators include:
a compound of formula (I):

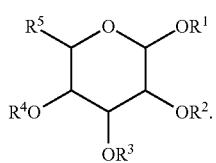

wherein:

$R^1$ is hydrogen, alkyl, alkenyl or alkynyl;

$R^2$ is selected from hydrogen, $(C_2-C_{20})$alkyl, $(C_2-C_{20})$alkenyl, $(C_2-C_{20})$alkynyl, $-[R^6R^7(R^8)0]_wR^9$, wherein w is from 1 to 10, preferably 2 to 9;

$R^3$ is selected from hydrogen, alkyl, alkenyl, alkynyl, $-[R^6R\backslash R^8)0]_yR^9$, wherein y is from 1 to 10 or 2 to 9;

$R^4$ is selected from hydrogen, alkyl, alkenyl, alkynyl, $-[R^6R\backslash R^8)0]xR^9$, wherein x is from 1 to 10, preferably 2 to 9;

$R^5$ is selected from hydrogen, alkyl, alkenyl, alkynyl, $-R^60\ R^9$, $-R^60\ [R^6R^7(R^8)0]zR^9$, wherein z is from 1 to 10, preferably 2 to 9;

each $R^6$ and $R^7$ are independently selected from $(C_2-C_{20})$alkylene, $(C_2-C_{20})$alkenylene, or $(C_2-C_{20})$alkynylene; and each $R^8$ and $R^9$ is independently selected from hydrogen or alkyl, a compound of formula (II):

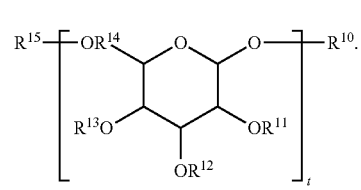

wherein:

$R^{10}$ is hydrogen, $(C_2-C_{20})$alkyl, $(C_2-C_{20})$alkenyl or $(C_2-C_{20})$alkynyl;

each $R^{11}$ is independently selected from hydrogen, $(C_2-C_{20})$alkyl, $(C_2-C_{20})$alkenyl, $(C_2-C_{20})$alkynyl;

each $R^{12}$ is independently selected from hydrogen, $(C_2-C_{20})$alkyl, $(C_2-C_{20})$alkenyl, or $(C_2-C_{20})$alkynyl;

each $R^{13}$ is independently selected from hydrogen, $(C_2-C_{20})$alkyl, $(C_2-C_{20})$alkenyl, or $(C_2-C_{20})$alkynyl;

each $R^{14}$ is selected from $(C_2-C_{20})$alkylene, $(C_2-C_{20})$alkenylene, or $(C_2-C_{20})$alkynylene; and $R^{15}$ is hydrogen, $(C_2-C_{20})$alkyl, $(C_2-C_{20})$alkenyl or $(C_2-C_{20})$ alkynyl; wherein t is 5 or less, preferably 1, 2 or 3;

Sucrose Laurate, Sucrose Dilaurate, Sucrose Myristate, Sucrose Palmitate, Sucrose Stearate, Sucrose Distearate, Sucrose Tristearate, and their mixtures;

Trimethylcyclohexane derivatives having the formula (III):

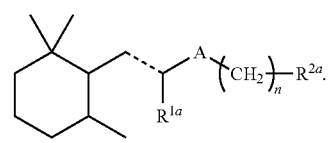

wherein:

n is 0, 1 or 2;

A is C=O or CH—OH;

$R^{1a}$ is hydrogen or methyl;
$R^{2a}$ is a $C_2$-$C_{10}$ hydrocarbon group; and
 is a saturated or unsaturated carbon-carbon bond:
L-menthoxy ether derivatives having the formula (IV):

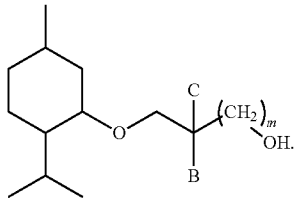
(IV)

wherein:
m is 0, 1 or 2;
B is hydrogen or OH;
and C is hydrogen or methyl;
Tetra-hydronaphthalene derivatives having the formula (V):

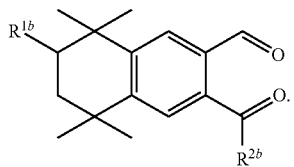
(V)

wherein:
$R^{1b}$ is hydrogen or methyl; and
$R^{2b}$ is alkyl;
140
Hyaluronic acid disaccharide sodium salt, sodium hyaluronate and their mixtures;
Ether derivatives having the formula (VI) or formula (VII):

$$C_5H_lO_m\text{—}(OR^{1c})_n \quad (VI).$$

wherein:
$C_5H_lO_m$ is a pentose residue, wherein l is an integer from 6 to 9, and m is
an integer from 1 to 4:
n is an integer from 1 to 4; and
$R^{1c}$ is $C_4$-$C_{20}$ hydrocarbon group; and $$C_5H_cO_d\text{—}(OCH_2CH_2O\text{—}CH_2CH_2\text{—}O\text{—}R^{1e})_e \quad (VII).$$

wherein:
$C_6H_xO_y$ is a hexose residue, wherein x is an integer from 7 to 11, and y is
an integer from 1 to 5;
z is an integer from 1 to 5; and
$R^{1d}$ is $C_4$-$C_{20}$ hydrocarbon group; and
Diethylene Glycol Ether derivatives having the formula (VIII) or formula (IX):

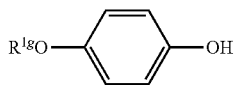
(VIII)

wherein:
$C_5H_cO_d$ is a pentose residue, wherein c is an integer from 6 to 8,
and d is an integer from 1 to 3;
e is an integer from 2 to 4;
and $R^{1e}$ is $C_1$-$C_6$ alkyl
group; and

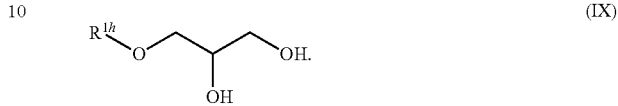
(IX)

wherein:
$C_6H_fO_g$ is a hexose residue, wherein f is an integer from 7 to 10, and g is an integer from 1 to 4;
h is an integer from 2 to 5;
and $R^{1f}$ is $C_1$-$C_6$ alkyl
group;
Hydroquinone Glycoside derivatives having the formula (X):

$$R^{1i}OCO^{R2i}NCOOR^{3i} \quad (X).$$

wherein:
$R^{1g}$ is selected from the group consisting of: (i) pentose residue, hexose residue, aminosaccharide residue, uronic acid residue and their mixtures; (ii) methylated versions of group (i); and (iii) mixtures of groups (i) and (ii); and Propylene Glycol Propyl Ether; Dicetyl Ether; Polyglycerin-4 Ethers; Isoceteth-5; Isoceteth-7, Isoceteth-10; Isoceteth-12; Isoceteth-15; Isoceteth-20; Isoceteth-25; Isoceteth-30; Disodium Lauroamphodipropionate; Hexaethylene glycol monododecyl ether; and their mixtures;
Glyceryl Ether derivatives having the formula (XI):

(XI)

wherein:
$R^{1h}$ is $C_4$-$C_{12}$ aliphatic hydrocarbon group;
Panthenol Ethyl Ether, DL-Panthenol and their mixtures;
Aliphatic Dibasic Acid Diester derivatives having the formula (XII):

$$R^{1i}OCOR^{2i}COOR^{3i} \quad (XII).$$

wherein:
$R^{1i}$ is $C_4$-$C_5$ alkyl;
$R^{2i}$ is $C_4$ alkylene;
and $R^{3i}$ is $C_4$-$C_5$
alkyl; and
Aliphatic Ether derivatives having the formula (XIII):

$$R^{4i}\text{—}O\text{—}(CH(CH_3)\text{—}CH_2O)_a\text{—}(CH_2\text{—}CH_2O)_b\text{—}H \quad (XIII).$$

wherein:
a and b are integers such that the sum of a and b is from 1 to 4;
and $R^{4i}$ is an aliphatic chain comprising from 8 to 18 carbons;
N-hexadecyl n-nonanoate, Noctadecyl n-nonanoate and their mixtures;

Tricyclodecane Amide derivatives selected from the group consisting of:
the compounds of formula (XIV):

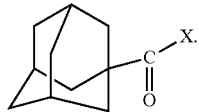
(XIV)

wherein:
X is selected from:

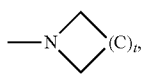
(Xa)

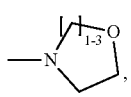
(Xb)

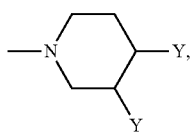
(Xc)

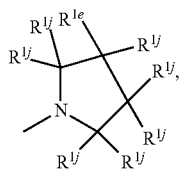
(Xd)

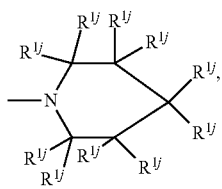
(Xe)

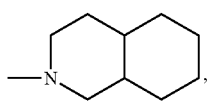
(Xf)

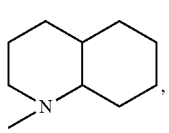
(Xg)

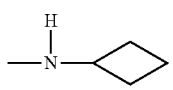
(Xh)

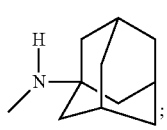 or (Xi)

$t$ is 1 to 8;
Y is hydrogen, or a halogen; and
each $R^{1j}$ is independently selected from a hydrogen, or $C_1$-$C_4$ alkyl; the compounds of formula (XV):

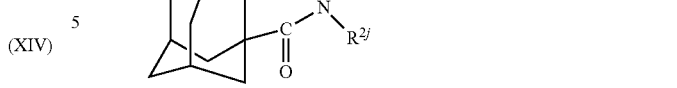
(XV)

wherein:
each $R^{2j}$ is independently selected from a hydrogen, methyl, ethyl or $C_3$-$C_{18}$
alkyl, cycloalkyl or cycloheteroalkyl, with the proviso that both $R^{2e}$ groups are not hydrogen; and
mixtures of the compounds of formulae (XII) and (XIII); and mixtures thereof.

Tables 4(a) and 4(b) provide lists of suitable non-odorous fragrance modulators.

TABLE 4(a)

Substantially Non-Odorous Fragrance Modulators

| No. | Group | Chemical Name | CAS Number | Supplier |
|---|---|---|---|---|
| 1. | (a) | PPG-10 Methyl Glucose Ether | 61849-72-7 | Lubrizol |
| 2. | | PPG-20 Methyl Glucose Ether [1] | 61849-72-7 | |
| 3. | | Ethoxylated Methyl Glucose Ether [2] | 68239-42-9 | |
| 4. | | Caprylyl/Capryl Glucoside [3] | 68515-73-1 | BASF |
| 5. | | Undecyl Glucoside [3a] | — | SEPPIC (France) |
| 6. | (b) | Isocetyl Alcohol [4] | 36653-82-4 | Ashland Speciality Ingredients |
| 7. | (c) | PPG-3 Myristyl Ether [5] | — | Evonik |
| 8. | | Neopentyl Glycol Diethylhexanoate [6] | 28510-23-8 | Lubrizol |
| 9. | (d) | Sucrose Laurate | 25339-99-5 | Alfa Chemicals Ltd. (UK) |
| 10. | | Sucrose dilaurate | 25915-57-5 | Alfa Chemicals Ltd. (UK) |
| 11. | | Sucrose Myristate | 27216-47-3 | Mitsubishi Chemicals |
| 12. | | Sucrose Palmitate | 26446-38-8 | Alfa |
| 13. | | Sucrose Stearate | 25168-73-4 | Chemicals Ltd. (UK) |
| 14. | | Sucrose Distearate | 27195-16-0 | Mitsubishi Chemicals (JP) |
| 15. | | Sucrose Tristearate | 27923063-3 | Mitsubishi Chemicals (JP) |
| 16. | (e) | (E)-1-(2,2,6-trimethylcyclohexyl)oct-1-en-3-one [8] | — | Takasago (Japan) |
| 17. | (f) | 2-(1-menthoxy)ethhane-1-ol [9] | — | Takasago |
| 18. | | 1-(1-menthoxy)propane-2-ol [9] | — | (Japan) |
| 19. | | 3-(1-menthoxy)propane-1-ol [9] | — | |
| 20. | | 3-(1-menthoxy)propane-1, 2-diol [9] | — | |
| 21. | | 2-methyl-3-(1-menthoxy)propane-1,2-diol [9] | — | |
| 22. | | 4-(1-menthoxy)butane-1-ol [9] | — | |

TABLE 4(a)-continued

Substantially Non-Odorous Fragrance Modulators

| No. | Group | Chemical Name | CAS Number | Supplier |
|---|---|---|---|---|
| 23. | (g) | 1,1,4,4-tetramethyl-6-acetyl-7-formyl-1,2,3,4-tetrahydronaphthalene [10] | — | Givaudan (Switzerland) |
| 24. | | 1,1,4,4-pentamethyl-6-acetyl-7-formyl-1,2,3,4-tetrahydronaphthalene [10] | — | |
| 25. | (h) | Hyaluronic acid disaccharide sodium salt [11] | 9004-61-9 | Sigma Aldrich (UK) |
| 26. | | Sodium Hyaluronate [11] | 9067-32-7 | Kanebo (Japan) |
| 27. | (i) | Mono-o-(linalyl)-glucopyranose [12] | — | |
| 28. | | Di-o-(lialyl)-glucopyranose [12] | — | |
| 29. | | Tri-o-(linalyl)-glucopyranose [12] | — | |
| 30. | | Tetra-o-(linalyl)-glucopyranose [12] | — | |
| 31. | | Penta-o-(linayl)-glucopyranose [12] | — | |
| 32. | | Mono-o-(cis-3-hexenyl)-glactopyranose [12] | — | |
| 33. | | Di-o-(cis-3-hexenyl)-glactopyranose [12] | — | |
| 34. | | Tri-o-(cis-3-hexenyl)-glactopyranose [12] | — | |
| 35. | | Tetra-o-(cis-3-hexenyl)-glactopyranose [12] | — | |
| 36. | | Penta-o-(cis-3-hexenyl)-glactopyranose [12] | — | |
| 37. | (j) | Bis-O-(3,6-dioxadecanyl)-glucopyranose [13] | — | |
| 38. | | Tris-O-(3,6-dioadecanyl)-glucopyranose [13] | — | |
| 39. | | Tetrakis-O-(3,6-dioxadecanyl)-glucopyranose [13] | — | |
| 40. | | Petrakis-O-(3,6-dioxadecanyl)-glucopyranose [13] | — | |
| 41. | | Bis-O-(3,6-dioxaoctanyl)-galactopyranose [13] | — | |
| 42. | | Tris-O-(3,6-dioxaoctanyl)-galactopyranose [13] | — | |
| 43. | | Tetrakis-O-(3,6-dioxaoctanyl)-galactopyranose [13] | — | |
| 44. | | Pentakis-O-(3,6-dioxaoctanyl)-glucopyranose [13] | — | |
| 45. | | Bis-O-(3,6-dioxaheptanyl)-xylopyranose [13] | — | |
| 46. | | Tris-O-(3,6-dioxaheptanyl)-xylopyranose [13] | — | |
| 47. | | Tetrakis-O-(3,6-dioxaheptanyl)-xylopyranose [13] | — | |
| 48. | | Bis-O-(3,6-dioxadodecanyl)-glucopyranose [13] | — | |
| 49. | | Tris-O-(3,6-dioxadodecanyl)-glucopyranose [13] | — | |
| 50. | | Tetrakis-O-(3,6-dioxadodecanyl)-glucopyranose [13] | — | |
| 51. | | Pentakis-O-(3,6-dioxadodecanyl)-glucopyranose [13] | — | |
| 52. | (k) | Hydroquinone beta-D-glycoside [14] | 497-76-7 | Shiseido |
| 53. | (l) | Propylene Glycol Propyl Ether | 1569-01-3 | Sigma Aldrich (UK) |
| 54. | | Dicetyl Ether | 4113-12-6 | |
| 55. | | Poly-glycerin-4 Ethers | 25618-55-7 | Solvay Chemicals |
| 56. | | Isoceteth-5 | 69364-63-2 | Nihon Emulsion Company Ltd. |
| 57. | | Isoceteth-7 | 69364-63-2 | |
| 58. | | Isoceteth-10 | 69364-63-2 | |
| 59. | | Isoceteth-12 | 69364-63-2 | |
| 60. | | Isoceteth-15 | 69364-63-2 | |
| 61. | | Isoceteth-20 | 69364-63-2 | |
| 62. | | Isoceteth-25 | 69364-63-2 | |
| 63. | | Isoceteth-30 | 69364-63-2 | |
| 64. | | Disodium Lauroamphodipropionate | 68929-04-4 | Rhodia |
| 65. | | Hexaethylene glycol monododecyl ether [14b] | 3055-96-7 | Sigma Aldrich (UK) |
| 66. | (m) | Neopentyl Glycol Diisononanoate [15] | 27841-07-2 | Symrise (Germany) |
| 67. | | Cetearyl Ethylhexnoate [16] | 90411-68-0 | |
| 68. | (n) | 2-ethylhexyloxypropanediol [17] | 70455-33-9 | Takasago (JP) |
| 69. | (o) | Panthenol Ethyl Ether [18] | 667-83-4 | DSM Nutritional Products, Inc. (USA) |
| 70. | | DL-Panthenol | 16485-10-2 | Roche Inc. (USA) |
| 71. | (p) | Diisobutyl Adipate [19] | 141-04-8 | Sigma Aldrich (UK) |
| 72. | | Diisoamyl Adipate [19] | 6624-70-0 | |
| 73. | | PPG-11 Stearyl Ether [19a] | 25231-21-4 | Kao (JP) |
| 74. | (r) | N-hexadecyl n-nonanoate [19b] (e.g., cetyl nonanoate) | 72934-15-7 | Symnse (Germany) |
| 75. | | Noctadecyl n-nonanoate [19b] (e.g., stearyl nonanoate) | 107647-13-2 | |
| 76. | (s) | methanone, (morphonyl) tricyclo[3.3.1.1[3,7]]dec-1-yl- [20] | — | Unilever (UK) |
| 77. | | methanone, (piperidinyl) tricyclo[3.3.1.1[3,7]]dec-1-yl- [20] | — | |
| 78. | | methanone, (pyrrolidinyl) tricyclo[3.3.1.1[3,7]]dec-1-yl- [20] | — | |
| 79. | | methanone, (azetidinyl) tricyclo[3.3.1.1[3,7]]dec-1-yl- [20] | — | |
| 80. | | methanone, (hexahydroazepinyl) tricyclo[3.3.1.1[3,7]]dec-1-yl- [20] | — | |
| 81. | | methanone, 4-cyano-piperidinyl) tricyclo[3.3.1.1[3,7]]dec-1-yl- [20] | — | |
| 82. | | methanone, (4-amido-piperidinyl) tricyclo[3.3.1.1[3,7]]dec-1-yl- [20] | — | |
| 83. | | methanone, (Tricyclo[3.3.1.1[3,7]]decanyl)-N-tricyclo[3.3.1.1[3,7]]dec-1-yl- [20] | — | |

TABLE 4(a)-continued

Substantially Non-Odorous Fragrance Modulators

| No. | Group | Chemical Name | CAS Number | Supplier |
|---|---|---|---|---|
| 84. | | methanone, (decahydroisoquinolinyl) tricyclo[3.3.1.1$^{3,7}$] dec-1-yl- [20] | — | |
| 85. | | methanone, (decahydroisoquinolinyl) tricyclo[3.3.1.1$^{3,7}$] dec-1-yl- [20] | — | |
| 86. | | methanone, (decahydroquinolinyl) tricyclo[3.3.1.1$^{3,7}$] dec-1-yl- [20] | — | |
| 87. | | methanone, (3,3-dimethyl-1-piperidinyl) tricyclo[3.3.1.1$^{3,7}$] dec-1-yl- [20] | — | |
| 88. | | methanone, (2-methyl-1-piperidinyl) tricyclo[3.3.1.1$^{3,7}$] dec-1-yl- [20] | — | |
| 89. | | methanone, (4-methyl-1-piperidinyl) tricyclo[3.3.1.1$^{3,7}$] dec-1-yl- [20] | — | |
| 90. | | methanone, (3-methyl-1 piperidinyl) tricyclo[3.3.1.1$^{3,7}$] dec-1-yl- [20] | — | |
| 91. | | methanone, (3,5-ditnethyl-l-piperidinyl) tricyclo[3.3.1.1$^{3,7}$] dec-1-yl- [20] | — | |
| 92. | | methanone, (4-methyl-4-ethy-piperidinyl) tricyclo[3.3.1.1$^{3,7}$] dec-1-yl- [20] | — | |
| 93. | | methanone, (3,3-diethyl-l-pyrrolidinyl) tricyclo[3.3.1.1$^{3,7}$] dec-1-yl- [20] | — | |
| 94. | | methanone, (N,N-diisopropyl) tricyclo[3.3.1.1$^{3,7}$] dec-1-yl- [20] | — | |
| 95. | | methanone, (3,3-dimethylbutylaminyl) tricyclo[3.3.1.1$^{3,7}$] dec-1-yl- [20] | — | |
| 96. | | methanone, (2,2-dimethylpropylaminyl) tricyclo[3.3.1.1$^{3,7}$] dec-1-yl- [20] | — | |
| 97. | | methanone, 1,1-dimethyl-3,3-dimethylbutylaminyl) tricyclo[3.3.1.1$^{3,7}$] dec-1-yl- [20] | — | |
| 98. | | methanone, (1,3-dimethyl-butylaminyl) tricycle[3.3.1.1$^{3,7}$] dec-1-yl- [20] | — | |
| 99. | (t) | Bis-methoxy PEG-13 PEG-438/PPG-110 SMD1 Copolymer [21] | 936645-35-1 | Polymer Expert S.A. (Pessac, France) |
| 100. | (u) | propyl {4-[2-(diethylamino)-2-oxoethoxy]-3-methoxyphenyl} acetate [22] | 61791-12-6 | Sigma Aldrich (US) |
| 101. | (v) | 3-((2-ethylhexy)oxy) propane-1,2-diol [23] | 70445-33-9 | — |
| 102. | | 3-((2-propylheptyl) oxy)propane-1,2-diol [23] | — | — |
| 103. | | 1-amino-3-((2-ethylhexyl)oxy) propan-2-ol [23] | 99509-00-9 | — |

[1] available as GLUCAM ™ P-20.
[2] available as Glucam ™ E-20.
[3] available as Plantacare ® 810 UP.
[3a] available as Simulsol ® SL 11W.
[4] available as CERAPHYL ® ICA.
[5] available as Tegosoft ®APM.
[6] available as Schercemol ™ NGDO.
[7] disclosed in U.S. Pat. No. 6,737,396B2 (Firmenich), column 1, lines 43-47.
[8] diclosed as compound 1'i in U.S. Pat. No. 6,440,400131 (Takasago Int. Corp.), col. 5.
[8a] diclosed in U.S. Pat. No. 4,313,855 (Dragoco Gerberding, & Co. GmbH), col. 1, lines 12-13.
[9] disclosed in U.S. Pat. No. 7,538,081B2 (Takasago Int. Corp.), column 7, lines 50-53.
[10] disclosed in U.S. Pat. No. 6,147,049 (Givaudan Roure), col. 5, line 24, to col. 6, line 17.
[11] disclosed in PCT Publication No. WO85/04803 (Diagnostic), pg. 2, line 1 to pg. 4, line 2.
[12] disclosed in JP Patent No. 61-083114 (Kanebo).
[13] disclosed in JP Patent No. 61-063612 (Kanebo).
[14] disclosed in JP Patent No. 6-2-084010 (Shiseido).
[14b] available as: Laureth-6.
[15] disclosed in U.S. Patent Publication No. 2011/0104089A1 (Symrise), para. [0001].
[16] available as PCL-Liquid ® 100.
[17] disclosed in U.S. Pat. No. 7,196,052 (Takasago Int, Corp.), col, 4, lines 34-35.
[18] disclosed in EP Patent Publication No. 616800A2 (Givaudan), pg. 2, lines 12-25.
[19] disclosed in U.S. Pat. No. 4,110,626 (Shiseido), column 3, lines 54-56.
[19a] disclosed in PCT Publication No. WO2014/155019 (LVMH).
[19b] disclosed in U.S. Pat. No. 9,050,261 (Symrise).
[20] disclosed as compounds C1-C22 in WO2014/139952 (Unilever).
[21] available as Expert Gel ® EG56.
[22] available as Kolliphor ® EL.
[23] disclosed in U.S. Pat. No. 9,050,261 (Symrise).

Further examples of non-odorous fragrance modulator is selected from the group of materials disclosed in Table 4(b).

TABLE 4(b)

Substantially Non-Odorous Fragrance Modulators

| No. | Chemical or INCI Name | Trade Name | CAS Number | Supplier |
|---|---|---|---|---|
| 1. | C12-14 Sec-Pareth-3 | Tergitol ® 15-S-7 | 68131-40-8 | Sigma Aldrich (UK) |
| 2. | Poly(ethylene glycol-ran-propylene glycol) monobutyl ether | PPG-7-Buteth-10 | 9038-95-3 | Sigma Aldrich (UK) |

TABLE 4(b)-continued

Substantially Non-Odorous Fragrance Modulators

| No. | Chemical or INCI Name | Trade Name | CAS Number | Supplier |
|---|---|---|---|---|
| 3. | PPG-4-Ceteth-1.0 | Nikkol PBC-33 | 37311-01-6 | Chemical Navi |
| 4. | Deceth-4 | Ethal DA-4 | 5703-94-6 | Ethox Chemicals, Inc. |
| 5. | PPG-5-Ceteth-20 | AEC PPG-5-Ceteth-20 | 9087-53-0 | A & E Connock (Perfumery & Cosmetics) Ltd. |
| 6. | C14-15 Pareth-7 | Neodol 45-7 alcohol ethoxylate | 68951-67-7 | Shell Chemical Company |
| 7. | Linear alcohol (C12-15) Pareth-3ethoxylate; POE-7 | Bio-soft N25-7 | 68131-39-5 | Stephan Company (USA) |
| 8. | Linear alcohol (C12-13) Pareth-3ethoxylated, POE-6.5) | Bio-soft N23-6.5 | 66455-14-9 | |
| 9. | Polyethylene glycol 1100 mon (hexadecyl/octadecyl) ether | Cremophor ® A 25 | 68439-49-6 | Sigma Aldrich (UK) |
| 10. | Linear alcohol (C9-11) ethoxylated POE -8 Pareth-3 | Bio-soft N91-8 | 68439-46-3 | Stephan Company (USA) |
| 11. | Coceth-10 or Polyoxyethylene (10) dodecyl ether | Genapol ® C-100 | 61791-13-7 | Sigma Aldrich (UK) |
| 12. | Alcohols, C12-14, ethoxylated | Rhodasurf ® LA 30 | 68439-50-9 | Solvay Solutions Italia S.p.A. |
| 13. | Poly(ethylene glycol) methyl ether | Poly(ethylene glycol) methyl ether | 9004-74-4 | Sigma Aldrich (UK) |
| 14. | C10-16 Pareth-1 | Neodol ® PC 110 | 68002-97-1 | Shell Chemical Company |
| 15. | PPG-11 Stearyl Ether | Arlamol ™ PS11E | 25231-21-4 | Croda (UK) |
| 16. | Steareth-100 | Brij ® S100 | 9005-00-9 | Sigma Aldrich (UK) |
| 17. | Polyethylene glycol hexadecyl ether | Brij ® C-58 | 9004-95-9 | Sigma Aldrich (UK) |
| 18. | Pluronic ® F-127 | Pluronic ® F-127 | 9003-11-6 | Sigma Aldrich (UK) |
| 19. | Linear Alcohol (C11) Ethoxylate, POE-5 | Bio-soft N1-5 | 34398-01-1 | Stepan Canada Inc. |
| 20. | Laureth-10 | Intrasol FA Dec. 18, 2010 | 6540-99-4 | Evonik Industries AG |
| 21. | Decaethylene glycol mono-dodecyl ether | Polyoxyethylene (10) lauryl ether | 9002-92-0 | Sigma Aldrich (UK) |
| 22. | Ethylene glycol monomethyl ether | 2-Methoxyethanol | 109-86-4 | Sigma Aldrich (UK) |
| 23. | Myreth-4 | Homulgator 920 G | 27306-79-2 | Grau Aromatics GmbH & Company KG |
| 24. | Oleth-16 Alkoxylated Alcohols | Pegnol O-16A | 25190-05-0 | Toho Chemical Industry Co., Ltd. |
| 25. | Isosteareth-5 | Emalex 1805 | 52292-17-8 | Nihon Emulsion Company, Ltd. |
| 26. | PPG-10 Cetyl Ether | Arlamol ™ PC10 | 9035-85-2 | Croda (UK) |
| 27. | Polyoxy(ethylene glycol) (18) tridecyl ether | Poly(ethylene glycol) (18) tridecyl ether | 24938-91-8 | Sigma-Aldrich (UK) |
| 28. | Poly(oxy-1,2-ethanediyl), a-decyl-w-hydroxy- | ALFONIC ® 10-8 Ethoxylate | 26183-52-8 | Sasol Chemicals (USA) LLC |
| 29. | Laurel-1 | Mackam ™ 2LSF | 4536-30-5 | Rhodia (DE) |
| 30. | PEG-5 Hydrogenated Tallow Amine | Ethox HTAM-5 | 61791-26-2 | Ethox Chemicals, Inc. |

TABLE 4(b)-continued

Substantially Non-Odorous Fragrance Modulators

| No. | Chemical or INCI Name | Trade Name | CAS Number | Supplier |
|---|---|---|---|---|
| 31. | PEG-15 Oleamine | Nikkol TAMNO-15 | 26635-93-8 | Nikko Chemicals Co., Ltd. |
| 32. | Polyoxyethylene (20) oleyl ether | Brij® O20-SS | 9004-98-2 | Sigma Aldrich (UK) |
| 33. | Cetoleth-10 | Brij® CO10 | 8065-81-4 | Croda, Inc. |
| 34. | Talloweth-7 | Emulmin 70 | 61791-28-4 | Sanyo Chemical Industries Ltd. |
| 35. | Isobutoxypropanol Alcohols | Isobutoxypropanol | 34150-35-1 | MolPort |
| 36. | Isobutoxypropanol Alcohols | Isobutoxypropanol | 23436-19-3 | AKos Consulting & Solutions |
| 37. | Diethylene Glycol | Twincide EDG | 111-46-6 | Roda |
| 38. | Methoxyethanol | Hisolve MC | 109-86-4 | Toho Chemical Industry Co., Ltd. |
| 39. | Ethoxyethanol Alcohols | 2-Ethoxyethanol | 110-80-5 | Sigma-Aldrich (UK) |
| 40. | Methoxyisopropanol Alcohols | Dowanol™ PM | 107-98-2 | The Dow Chemical Company |
| 41. | Methoxyethanol | Hisolve MC | 32718-54-0 | Toho Chemical Industry Co., Ltd. |
| 42. | Methylal Ethers | Dimethoxymethane | 109-87-5 | Sigma-Aldrich (UK) |
| 43. | 3-Methoxybutanol | Methoxybutanol | 2517-43-3 | Hans Schwarzkopf GmbH/ Co. KG |
| 44. | Butoxyethanol | Butyl OXITOL | 111-76-2 | Shell Chemical Company |
| 45. | Propylene Glycol n-Butyl Ether | Dowanol™ PnB | 5131-66-8/29387-86-8 | The Dow Chemical Company |
| 46. | Propylene Glycol Butyl Ether | Propylene Glycol Butyl Ether | 15821-83-7 | Sigma Aldrich (UK) |
| 47. | 2-(2-butoxyethoxy)ethanol | Diethylene glycol butyl ether | 112-34-5 | Sigma Aldrich (UK) |
| 48. | Deceth-4 Phosphate | Crodafos™ D4A | 52019-36-0 | Croda, Inc. |
| 49. | 2-(Hexadecyloxy)ethanol | Ethylene glycol monohexadecyl ether | 2136-71-2 | Sigma-Aldrich (UK) |
| 50. | Poly(propylene glycol) monobutyl ether | Poly(propylene glycol) monobutyl ether | 9003-13-8 | Sigma-Aldrich (UK) |
| 51. | Propylene Glycol Propyl Ether | Dowanol™ PnP | 30136-13-1 | The Dow Chemical Company |
| 52. | Propylene Glycol n-Butyl Ether | Dowanol™ PnB | 29387-86-8/5131-66-8 | The Dow Chemical Company |
| 53. | Dipropylene glycol monomethyl ether | Di(prorylene glycol) methyl ether, mixture of isomers | 34590-94-8 | Sigma Aldrich (UK) |
| 54. | Dipropylene Glycol Dimethyl Ether | Proglyde™ DMM | 111109-77-4 | The Dow Chemical Company |
| 55. | PPG-2 Methyl Ether | Dowanol™ DPM | 13429-07-7 | The Dow Chemical Company |
| 56. | Methoxydiglycol Ethers | OriStar DEGME | 111-77-3 | Orient Stars LLC |
| 57. | Diethylene glycol ethyl ether | Di(ethylene glycol) ethyl ether | 111-90-0 | Sigma Aldrich (UK) |
| 58. | Dimethoxydiglycol Ethers | Dimethyldiglycol | 111-96-6 | H & V Chemicals |
| 59. | PPG-3 Methyl Ether | Dowanol™ TPM | 37286-64-9 | The Dow Chemical Company |

TABLE 4(b)-continued

Substantially Non-Odorous Fragrance Modulators

| No. | Chemical or INCI Name | Trade Name | CAS Number | Supplier |
|---|---|---|---|---|
| 60. | Methyl Motpholine Oxide Amine Oxides | 224286 ALDRICH 4-Methylmorpholine N-oxide | 7529-22-8 | Sigma-Aldrich (UK) |
| 61. | Oleth-3 | Brij ® O3 | 5274-66-8 | Croda Europe, Ltd. |
| 62. | Tri(propylene glycol) n-butyl ether | Dowanol ™ TPnB | 55934-93-5 | Sigma-Aldrich (UK) |
| 63. | Tripropylene Glycol | Tripropylene Glycol | 24800-44-0 | Sigma-Aldrich (UK) |
| 64. | PPG-3 Methyl Ether Alkoxylated Alcohols | Dowanol ™ TPM | 25498-49-1 | The Dow Chemical Company |
| 65. | Triethylene glycol | Triglycol | 112-27-6 | Sigma Aldrich (UK) |
| 66. | PEG-3 Methyl Ether | Hymol ™ | 112-35-6 | Toho Chemical Industry Co., Ltd. |
| 67. | Laureth-3 | AEC Laureth-3 | 3055-94-5 | A & E Connock (Perfumery & Cosmetics) Ltd. |
| 68. | Ethylhex glycerin | AG-G-75008 | 70445-33-9 | Angene Chemical |
| 69. | Tetra(ethylene glycol) | Tetraethylene glycol | 112-60-7 | Sigma Aldrich (UK) |
| 70. | Steareth-3 | Isoxal 5 | 4439-32-1 | Vevy Europe SpA |
| 71. | Ceteth-3 | Emalex 103 | 4484-59-7 | Nihon Emulsion Company, Ltd. |
| 72. | Myreth-3 | Isoxal 5 | 26826-30-2 | Vevy Europe SpA |
| 73. | Trideceth-3 | Alfonic ® TDA-3 Ethoxylate | — | Sasol North America, Inc. |
| 74. | Ceteth-2 | Brij ® C2 | 5274-61-3 | Croda Europe, Ltd. |
| 75. | Oleth-2 | Brij ® O2 | 5274-65-7 | Croda, Inc. |
| 76. | Steareth-2 | Brij ® S2 | 16057-43-5 | Croda, Inc. |
| 77. | Cetoleth-10 | Brij ® CO10 | 8065-81-4 | Croda, Inc. |
| 78. | Trimethyl Pentanol Hydroxyethyl Ether Alcohols | Trimethyl Pentanol Hydroxyethyl Ether | 68959-25-1 | Angene Chemical |
| 79. | Steareth-10 Allyl Ether | Salcare ® SC80 | 109292-17-3 | BASF |
| 80. | TEA-Lauryl Ether | material ID-AG-J-99109 | 1733-93-3 | Angene Chemical |
| 81. | Polyglyceryl-2 Oleyl Ether | Chimexane NB | 71032-90-1 | Chimex |
| 82. | Batyl Alcohol | B402 ALDRICH | 544-62-7 | Sigma-Aldrich (UK) |
| 83. | Octaethylene Glycol | 15879 AIDRICH | 5117-19-1 | Sigma-Aldrich (UK) |
| 84. | Triglycerol diisostearate | Cithrol ™ | 66082-42-6 | Croda (UK) |
| 85. | Diglycerin | Diglycerin 801 | 59113-36-9 | Sakamoto Yakuhin Kogyo Co., Ltd. |
| 86. | Polyglycerin #310 | Polyglycetin #310 | 25618-55-7 | Sakamoto Yakuhin Kogyo Co., Ltd. |
| 87. | Distearyl Ether | Cosmacol ® SE | 6297-03-6 | Sasol Germany GmbH |
| 88. | Caprylyl Glyceryl Ether | Caprylyl Glyceryl Ether | 10438-94-5 | AKos Consulting & Solutions |
| 89. | Chimyl Alcohol | Chimyl Alcohol | 506-03-6 | Nikko Chemicals Co., Ltd. |
| 90. | Dipentaerythrityl Hexacaprylate/Hexacaprate | Liponate ® DPC-6 | 68130-24-5 | Lipo Chemicals, Inc. |
| 91. | Morpholine | 394467 ALDRICH | 110-91-8 | Sigma-Aldrich (UK) |
| 92. | Dimethyl Oxazolidine | OXABAN ™ -A | 51200-87-4 | The Dow Chemical Company |
| 93. | Ethyl Hydroxymethyl Oleyl Oxazoline | 4-Oxazolemethanol | 68140-98-7 | Angene Chemical |

TABLE 4(b)-continued

Substantially Non-Odorous Fragrance Modulators

| No. | Chemical or INCI Name | Trade Name | CAS Number | Supplier |
|---|---|---|---|---|
| 94. | Methyl Hydroxymethyl Oleyl Oxazoline | Adeka Nol GE-RF | 14408-42-5 | Adeka Corporation |
| 95. | Pramoxine HCl | OriStar PMHCL | 637-58-1 | Orient Stars LLC |
| 96. | Allantoin Ascorbate | Allantoin Ascorbate | 57448-83-6 | ABI Chem |
| 97. | Stearamidopropyl Morpholine Lactate | Mackalene ™ 326 | 55852-14-7 | Rhodia Inc. |
| 98. | Dioxolane | Elcotal DX | 646-06-0 | Lambiotte & CM, S.A. |
| 99. | Glycerol Formal | Glycerol Formal | 5464-28-8 | Sigma Aldrich (UK) |
| 100. | Stearamidopropyl Morpholine | Mackine 321 | 55852-13-6 | Rhodia Inc. |
| 101. | 2,4,6-Tris[bis(methoxymethyl)amino]-1,3,5-triazine | Poly(melamine-co-formaldehyde) methylated | 68002-20-0 | Sigma-Aldrich (UK) |
| 102. | Poloxamine 1307 | Pluracare ® 1307 | 11111-34-5 | BASF |
| 103. | Nonoxynol-8 | Igepal ® CO-610 | 27177-05-5 | Rhodia Inc. |
| 104. | Nonoxynol-10 | Igepal ® CO-710 | 27177-08-8 | Rhodia Inc, |
| 105. | Octoxynol-10 | Nikkol OP-10 | 2315-66-4 | Nikko Chemicals Co., Ltd. |
| 106. | Nonoxynol-9 | Igepal ® CO-630 | 68987-90-6 | Rhodia Inc, |
| 107. | Nonoxynol-9 Iodine | Nonoxynol-9 iodine | 94349-40-3 | Angene Chemical |
| 108. | Octylphenoxy poly(ethyleneoxy) ethanol, branched | Igepal ® CA-630 | 68987-90-6 | Rhodia Inc. |
| 109. | Sodium Octoxynol-2 Ethane Sulfonate | Triton ™ X-200 | 55837-16-6 | The Dow Chemical Company |
| 110. | Benzylhemiformal | Preventol D2 | 14548-60-8 | Lanxess Corporation |
| 111. | Nonoxynol-2 | Igepal ® CO-210 | 27176-93-8 | Rhodia Inc, |
| 112. | Octoxynol-3 | Igepal ® CA-420 | 2315-62-0 | The Dow Chemical Company |
| 113. | Nonoxynol-3 | Marlophen NP 3 | 27176-95-0 | Sasol Germany GmbH |
| 114. | Alkoxylated Alcohols | Alkasurf NP-4 | 7311-27-5 | Rhodia Inc. |
| 115. | Nonoxynol-3 | Triethylene Glycol Mono (p-nonylphenyl) Ether | 51437-95-7 | Santa Cruz Biotechnology |
| 116. | Nonoxynol-7 | Lowenol 2689 | 27177-03-3 | Jos. H. Lowenstein & Sons, Inc. |
| 117. | Nonoxynol-6 | Igepal ® CO-530 | 27177-01-1 | Rhodia Inc. |
| 118. | Nonoxynol-5 | Igepal ® CO-520 | 20636-48-0 | Rhodia Inc. |
| 119. | Nonoxynol-5 | Igepal ® CO-520 | 26264-02-8 | Rhodia Inc. |
| 120. | Nonoxynol-4 | Alkasurf NP-4 | 27176-97-2 | Rhodia Inc. |
| 121. | Polyglyceryl-10 Trioleate | Nikkol Decaglyn 3-OV | 102051-00-3 | Nikko Chemicals Co., Ltd. |
| 122. | Polyglyceryl-10 Dioleate | Nikkol Decaglyn 2-O | 33940-99-7 | Nikko Chemicals Co., Ltd. |
| 123. | Polyglyceryl-10 Tetraoleate | Caprol 10G40 | 34424-98-1 | Abitec Corporation |
| 124. | Polyglyceryl-10 Stearate | Nikkol Decaglyn 1-SV EX | 79777-30-3 | Nikko Chemicals Co., Ltd. |
| 125. | Polyglyceryl-10 Oleate | S-Face O-1001 P | 79665-93-3 | Sakamoto Yakuhin Kogyo Co., Ltd. |
| 126. | Polyglyceryl-10 Myristate | Nikkol Decaglyn 1-MV EX | 87390-32-7 | Nikko Chemicals Co., Ltd. |
| 127. | Dermofeel ® G 10 L | Dermofeel ® G 10 L | 34406-66-1 | Dr. Straetmans |
| 128. | Polyglyceryl-6 Laurate | NIKKOL Hexaglyn 1-L | 51033-38-6 | Chemical Navi |
| 129. | Polyglyceryl-6 Isostearate | S-Face IS-601 P | 126928-07-2 | Sakamoto Yakuhin Kogyo Co., Ltd. |

TABLE 4(b)-continued

Substantially Non-Odorous Fragrance Modulators

| No. | Chemical or INCI Name | Trade Name | CAS Number | Supplier |
|---|---|---|---|---|
| 130. | Choleth-10 | Emalex CS-10 | 27321-96-6 | Nihon Emulsion Company, Ltd. |
| 131. | Steareth-10 Allyl Ether/Acrylates Copolymer | Salcare ® SC80 | 109292-17-3 | BASF |
| 132. | Polyvinyl Stearyl Ether | Giovarez ® 1800 | 9003-96-7 | Phoenix Chemical, Inc. |
| 133. | Dicetyl Ether | Cosmacol Ether 16 | — | Sosol Germany GmbH |
| 134. | PPG-23-Steareth-34 | Unisafe 34S-23 | 9038-43-1 | Pola Chemical Industries, Inc. |
| 135. | Stearoxypropyl Dimethylamine | Farmin DM E-80 | 17517-01-0 | Kao Corp. |
| 136. | Distearyl Ether | Cosmacol SE | 6297-03-6 | Sasol Germany GmbH |
| 137. | Polyquaternium-10 | AEC Polyquaternium-10 | 55353-19-0 | A & E Connock (Perfumery Cosmetics) Ltd. |
| 138. | Octyl ether | Dioctyl ether | 629-82-3 | Sigma Adlrich (UK) |
| 139. | Ethyl Ether | Diethyl Ether | 60-29-7 | EMD Chemicals |
| 140. | Methyl Hexyl Ether Ethers | methyl hexyl ether | 4747-07-3 | TCI AMERICA |
| 141. | Ceteth-12 | Emalex 112 | 94159-75-8 | Nihon Emulsion Company, Ltd. |
| 142. | Ceteth-10 or cetyl alcohol POE-10 | Jeecol CA-10 | 14529-40-9 | Jeen International |
| 143. | Steareth-10 | Jeecol SA-10 | 13149-86-5 | Jeen International |
| 144. | Nonaethylene glycol monododecyl ether | Nonaethylene glycol monododecyl ether | 3055-99-0 | Sigma Aldrich (UK) |
| 145. | Oleth-10 | Brij ® O10 | 71976-00-6 | Croda, Inc. |
| 146. | Oleth-10 | Brij ® O10 | 24871-34-9 | Croda, Inc. |
| 147. | PEG-12 | Carbowax ™ PEG 600 | 6790-09-6 | The Dow Chemical Company |
| 148. | PEG-9 | Sabopeg 400 | 3386-18-3 | Sabo s.p.a. |
| 149. | PEG-10 | DECAETHYLENE GLYCOL | 5579-66-8 | MolPort |
| 150. | PEG-6 | Carbowax ™ PEG 300 | 2615-15-8 | The Dow Chemical Company |
| 151. | Glycerol propoxylate | Glycerol propoxylate | 25791-96-2 | Sigma Aldrich (UK) |
| 152. | Glycerol ethoxylate | Glycerol ethoxylate | 31694-55-0 | Sigma Aldrich (UK) |
| 153. | Laureth-8 | AFC Laureth-8 | 3055-98-9 | A & E Connock (Perfumery & Cosmetics) Ltd. |
| 154. | Oleth-8 | Emalex 508 | 27040-03-5 | Nihon Emulsion Company, Ltd. |
| 155. | Laureth-7 | Alfonic 1216CO-7 Ethoxylate | 3055-97-8 | Sasol North America, Inc. |
| 156. | Steareth-7 | Polyoxyethylene (7) stearyl ether | 66146-84-7 | Sigma Aldrich |
| 157. | Deceth-6 | Alfonic 1012-6.0 Ethoxylate | 5168-89-8 | Sasol North America, Inc. |
| 158. | Steareth-6 | Emalex 606 | 2420-29-3 | Nihon Emulsion Company, Ltd. |
| 159. | Hexaethylene glycol monododecyl ether | Hexaethylene glycol monododecyl ether | 3055-96-7 | Sigma-Aldrich (UK) |
| 160. | Hexaethylene glycol monohexadecyl ether | Hexaethylene glycol monohexadecyl ether | 5168-91-2 | Sigma-Aldrich (UK) |
| 161. | Beheneth-5 | Nikkol BB-5 | 136207-49-3 | Nikko Chemicals Co. Ltd, |
| 162. | Myreth-5 | Isoxal 12 | 92669-01-7 | Vevy Europe SpA |
| 163. | Steareth-5 | Jeecol SA-5 | 71093-13-5 | Jeen International Corporation |

TABLE 4(b)-continued

Substantially Non-Odorous Fragrance Modulators

| No. | Chemical or INCI Name | Trade Name | CAS Number | Supplier |
|---|---|---|---|---|
| 164. | Ceteth-5 | Emalex 105 | 4478-97-1 | Nihon Emulsion Company, Ltd. |
| 165. | Oleth-5 | Brij ® O5 | 53 53-27-5 | Croda, Inc. |
| 166. | Laureth-5 | Safol ® 23E5 Ethoxylate | 3055-95-6 | Sasol North America, Inc. |
| 167. | Steareth-4 | Jeecol SA-4 | 59970-10-4 | Jeen International Corporation |
| 168. | Laureth-4 | Brij ® L4 | 5274-68-0 | Croda, Inc. |
| 169. | Myreth-4 | Homulgator 920G | 39034-24-7 | Grau Aromatics GmbH & Company KG |
| 170. | Ceteth-4 | Procol CA-4 | 5274-63-5 | Protameen Chemicals |
| 171. | Oleth-4 | Chemal OA-4 | 5353-26-4 | Chemax, Inc. |
| 172. | Oleth-4 | Chemal OA-4 | 103622-85-1 | Chemax, Inc. |
| 173. | Polyimide-1 | Aquaflex ™ XL-30 | 497926-97-3 | Chemwill |
| 174. | Polymethoxy Bicyclic Oxazolidine | Caswell No. 494CA | 56709-13-8 | Angene Chemical |
| 175. | Hydroxymethyl Dioxoazabicyclooctane | Zoldine ™ ZT | 6542-37-6 | Angus Chemical Company |
| 176. | Dihydro-7a-ethyloxazolo[3,4-c]oxazole | 5-Ethyl-1-aza-3,7-dioxabicyclo[3.3.0]octane | 7747-35-5 | Sigma Aldrich (UK) |
| 177. | Dibenzylidene Sorbitol | Disorbene ® | 32647-67-9 | Roquette America, Inc. |
| 178. | Dimethyldibenzylidene Sorbitol | Millad ® 3988 | 135861-56-2 | Milliken Chemicals |
| 179. | Laureth-2 | Alfonic 1216CO-2 Ethoxylate | 3055-93-4 | Sasol North America, Inc. |
| 180. | 2-(2-Butoxyethoxy)ethyl (6-propylpiperonyl) ether | Piperonyl Butoxide | 51-03-6 | Sigma-Aldrich (UK) |
| 181. | Menthone Glycerin Acetal | Frescolat ® MGA | 63187-91-7 | Symrise |
| 182. | Propylene Glycol Caprylate | Mackaderm PGC | 68332-79-6 | Rhodia Inc. |
| 183. | Diethoxynonadiene | SBB016951 | 67674-36-6 | Ambinter |
| 184 | Menthoxypropanediol Alcohols | Coolact ® 10 | 87061-04-9 | Takasago International Corporation |
| 185. | 2-Diphenylmethoxy-N,N-dimethylethylamine hydrochloride | Diphenhydramine HCl | 147-24-0 | Sigma-Aldrich (UK) |
| 186. | 3-((2-ethylhexyl)oxy)propane-1,2-diol | — | 70445-33-9 | — |
| 187. | 3-((2-propylheptyl)oxy)propane-1,2-diol | — | — | — |
| 188. | 1-amino-3-((2-ethylhexyl)oxy)propan-7-ol | — | 99509-00-9 | — |
| 189. | 1-(1-Methyl-2-propoxyethoxy)-2-propanol | Di(propylene glycol) propyl ether | 29911-27-1 | Sigma Aldrich (UK) |

The compounds, as described above in Tables 4(a) and 4(b), act as a substantially non-odorous fragrance modulator of the overdosed perfume materials of the present invention. For example, the substantially non-odorous fragrance modulators, Without wishing to be bound by theory, it is believed that the substantially non-odorous fragrance modulators associate to the low-volatility fragrance materials to allow for high wt % (e.g., greater than 30 wt %) of the composition to allow the low-volatility fragrance materials to drive the perceived character of the fragrance, while mitigating or eliminating a perceived harshness of the composition by the user.

Volatile Solvents

The composition according to the present invention, can include a volatile solvent present in the amount of from about 20 wt % to about 99 wt % relative to the total weight of the composition, about 30 wt % to about 80 wt %, about 55 wt % to about 75 wt %, or less than, equal to, or greater than about 20 wt %, 25, 30, 35, 40, 45, 50, 55, 60, 65, 70, 75, 80, 85, 90, 95, or about 99 wt %, and wherein the solvent is a branch or unbranched $C_1$ to $C_{10}$ alkyl, akenyl or alkynyl group having at least one alcohol moiety, preferably ethanol, or isopropanol, or other alcohols (e.g., methanol, propanol, isopropanol, butanol, and mixtures thereof) commonly found in commercial fine fragrance products.

Accordingly, ethanol may be present in any of the compositions of the present invention, and more specifically, it will form from about 5 wt % to about 95 wt %, or even from about 10 wt % to about 80 wt %, 25 wt % to about 75 wt % of the composition, or combinations thereof, relative to the total weight of the composition. Alternatively, ethanol may be present in an amount of from about 10 wt % or 25 wt % to about 75 wt % or 80 wt %, relative to the total weight of the composition. The ethanol useful in the present invention may be any acceptable quality of ethanol, compatible and safe for the specific intended use of the composition such as, for example, topical applications of fine fragrance or cosmetic compositions.

Water

In some examples (e.g., those including a volatile solvent), water may be present in any of the compositions of the present invention, and more specifically, it may not exceed about 95 wt % relative to the total weight of the composition, about 90 wt % or less, about 85 wt % or less, about 80 wt %, or less, about 75 wt % or less, about 70 wt % or less, about 65 wt % or less, about 60 wt % or less, about 55 wt % or less, about 50 wt % or less, about 45 wt % or less, about 40 wt % or less, about 35 wt % or less, about 30 wt % or less, about 20 wt % or less, about 10 wt %, or less than, equal to, or greater than about 95 wt %, 90, 85, 80, 75, 70, 65, 60, 55, 50, 45, 40, 30, 35, 30, 25, 20, 15, 10, or 5 wt/o. Alternatively, water may be present in an amount of from about 5 wt % or about 95 wt % When the composition is a cosmetic composition the level of water should not be so high that the product becomes cloudy thus negatively impacting the product aesthetics. It is understood that the amount of water present in the composition may be from the water present in the volatile solvent (e.g., ethanol) used in the composition, as the case may be.

Non-Volatile Solvents

The composition may comprise a non-volatile solvent or a mixture of non-volatile solvents. Non-limiting examples of non-volatile solvents include benzyl benzoate, diethyl phthalate, isopropyl myristate, propylene glycol, dipropylene glycol, triethyl citrate, and mixtures thereof. These solvents often are introduced to the product via the perfume oil as many perfume raw materials may be purchased as a dilution in one of these solvents. Where non-volatile solvents are present, introduced either with the perfume materials or separately, then for the purposes of calculating the proportion of fragrance component having a vapor pressure of less than 0.001 Torr (0.000133 kPa) at 25° C. the total fragrance components does not include non-volatile solvents. Where non-volatile solvents are present, introduced either with the perfume materials or separately, then for the purposes of calculating the total level of fragrance component this does not include non-volatile solvents. In addition, if present with cyclic oligosacchrides, the non-volatile solvent may be included at a weight ratio of the non-volatile solvent to the cyclic oligosaccharide of less than 1:1, less than 1:2, less than 1:10, or less than 1:100.

Entrapment Materials

In other examples, compositions of the present invention can include an entrapment material at a level such that the weight ratio of the entrapment material to the fragrance materials is in the range of from about 1:20 to about 20:1. in some examples, the composition may comprise an entrapment material present in the amount of from about 0.001 wt % to about 40 wt %, from about 0.1 wt % to about 25 wt %, from about 0.3 wt % to about 20 wt %, from about 0.5 wt % to about 10 wt %, or from about 0.75 wt % to about 5 wt %, relative to the total weight of the composition. The compositions disclosed herein may include from 0.001 wt % to 40%, from 0.1 wt % to 25 wt %, from 0.3 wt % to 20 wt %, from 0.5 wt % to 10 wt % or from 0.75 wt % to 5 wt %, relative to the total weight of the composition, of a cyclic oligosaccharide.

Suitable entrapment materials for use herein are selected from polymers; capsules, microcapsules and nanocapsules; liposomes, absorbents; cyclic oligosaccharides and mixtures thereof. Preferred are absorbents and cyclic oligosaccharides and mixtures thereof. Highly preferred are cyclic oligosaccharides (see PCT Publication Nos. WO2000/67721 (Procter & Gamble); and WO2000/67720 (Procter & Gamble); and U.S. Pat. No. 6,893,647 (Procter & Gamble)).

As used herein, the term "cyclic oligosaccharide" means a cyclic structure comprising six or more saccharide units. Preferred for use herein are cyclic oligosaccharides having six, seven or eight saccharide units and mixtures thereof, more preferably six or seven saccharide units and even more preferably seven saccharide units. It is common in the art to abbreviate six, seven and eight membered cyclic oligosaccharides to a, p and y respectively.

The cyclic oligosaccharide of the compositions used for the present invention may comprise any suitable saccharide or mixtures of saccharides. Examples of suitable saccharides include, but are not limited to, glucose, fructose, mannose, galactose, maltose and mixtures thereof. However, preferred for use herein are cyclic oligosaccharides of glucose. The preferred cyclic oligosaccharides for use herein are α-cyclodextrins or β-cyclodextrins, or mixtures thereof, and the most preferred cyclic oligosaccharides for use herein are β-cyclodextrins.

The cyclic oligosaccharide, or mixture of cyclic oligosaccharides, for use herein may be substituted by any suitable substituent or mixture of substituents. Herein the use of the term "mixture of substituents" means that two or more different suitable substituents can be substituted onto one cyclic oligosaccharide. The derivatives of cyclodextrins consist mainly of molecules wherein some of the OH groups have been substituted. Suitable substituents include, but are not limited to, alkyl groups; hydroxyalkyl groups; dihydroxyalkyl groups; (hydroxyalkyl)alkylenyl bridging groups such as cyclodextrin glycerol ethers; aryl groups; maltosyl groups; allyl groups; benzyl groups; alkanoyl groups; cationic cyclodextrins such as those containing 2-hydroxy-3-(dimethylamino) propyl ether; quaternary ammonium groups; anionic cyclodextrins such as carboxyalkyl groups, sulphobutylether groups, sulphate groups, and succinylates; amphoteric cyclodextrins; and mixtures thereof.

The substituents may be saturated or unsaturated, straight or branched chain. Preferred substituents include saturated and straight chain alkyl groups, hydroxyalkyl groups and mixtures thereof. Preferred alkyl and hydroxyalkyl substituents are selected from $C_1$-$C_8$ alkyl or hydroxyalkyl groups or mixtures thereof, more preferred alkyl and hydroxyalkyl substituents are selected from $C_1$-$C_6$ alkyl or hydroxyalkyl groups or mixtures thereof, even more preferred alkyl and hydroxyalkyl substituents are selected from $C_1$-$C_4$ alkyl or hydroxyalkyl groups and mixtures thereof. Especially preferred alkyl and hydroxyalkyl substituents are propyl, ethyl and methyl, more especially hydroxypropyl and methyl and even more preferably methyl.

Suitable cyclic oligosaccharides for use in the present invention are unsubstituted, or are substituted by only saturated straight chain alkyl, or hydroxyalkyl substituents. Therefore, preferred examples of cyclic oligosaccharides for use herein are α-cyclodextrin, β-cyclodextrin, methyl-α-cyclodextrin, methyl-β-cyclodextrin, hydroxypropyl-α-cyclodextrin and hydroxypropyl-β-cyclodextrin. Most preferred examples of cyclic oligosaccharides for use herein are methyl-α-cyclodextrin and methyl-β-cyclodextrin. These are available from Wacker-Chemie GmbH Hanns-Seidel-Platz 4, Munchen, DE under the tradename Alpha W6 M and Beta W7 M respectively.

The cyclic oligosaccharides of the compositions used for the present invention can be soluble in water, ethanol, or both water and ethanol. As used herein "soluble" means at least about 0.1 g of solute dissolves in 100 mL of solvent, at 25° C. and 1 standard atmospheric pressure (760 mmHg). The cyclic oligosaccharides for use herein have a solubility of at least about 1 g/100 mL, at 25° C. and 1 atm of pressure. In some examples, cyclic oligosaccharides are only present at levels up to their solubility limits in a given composition at room temperature. A person skilled in the art will recognize that the levels of cyclic oligosaccharides used in the present invention will also be dependent on the components of the composition and their levels, for example the solvents used or the exact fragrance oils, or combination of fragrance oils, present in the composition. Therefore, although the limits stated for the entrapment material are preferred, they are not exhaustive.

Propellants

The compositions described herein may include a propellant. Some examples of propellants include compressed air, nitrogen, inert gases, carbon dioxide, and mixtures thereof. Propellants may also include gaseous hydrocarbons like propane, n-butane, isobutene, cyclopropane, and mixtures thereof. Halogenated hydrocarbons like 1,1-difluoroethane may also be used as propellants. Some non-limiting examples of propellants include 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), and 152A (1,1 diflouroethane). The propellant may have a concentration from about 15%, 25%, 30%, 32%, 34%, 35%, 36%, 38%, 40%, or 42% to about 70%, 65%, 60%, 54%, 52%, 50%, 48%, 46%, 44%, or 42% by weight of the total fill of materials stored within the container.

Antiperspirant Active

The compositions described herein may be free of, substantially free of, or may include an antiperspirant active (e.g., any substance, mixture, or other material having antiperspirant activity). Examples of antiperspirant actives include astringent metallic salts, like the inorganic and organic salts of aluminum, zirconium and zinc, as well as mixtures thereof. Such antiperspirant actives include, for example, the aluminum and zirconium salts, such as aluminum halides, aluminum hydroxyhalides, zirconyl oxyhalides, zirconyl hydroxyhalides, and mixtures thereof.

Other Ingredients

In yet another aspect, the composition consists essentially of the recited ingredients but may contain small amounts (not more than about 10 wt %, preferably no more than 5 wt %, or preferably no more than 2 wt % thereof, relative to the total weight of the composition) of other ingredients that do not impact on the fragrance profile, particularly the evaporation rate and release of the fragrance materials. For example, a fine fragrance composition may comprise stabilizing or anti-oxidant agents, UV filters or quenchers, or colouring agents, commonly used in perfumery. There are a number of other examples of additional ingredients that are suitable for inclusion in the present compositions, particularly in compositions for cosmetic use. These include, but are not limited to, alcohol denaturants such as denatonium benzoate; UV stabilizers such as benzophenone-2; antioxidants such as tocopheryl acetate; preservatives such as phenoxyethanol, benzyl alcohol, methyl paraben, and propyl paraben; dyes; pH adjusting agents such as lactic acid, citric acid, sodium citrate, succinic acid, phosphoric acid, sodium hydroxide, and sodium carbonate; deodorants and anti-microbials such as farnesol and zinc phenolsulphonate; humectants such as glycerine; oils; skin conditioning agents such as allantoin; cooling agents such as trimethyl isopropyl butanamide and menthol; silicones; solvents such as hexylene glycol; hair-hold polymers such as those described in PCT Publication No. WO94/08557 (Procter & Gamble); salts in general, such as potassium acetate and sodium chloride and mixtures thereof.

In yet another aspect, the composition of the present invention, depending on its intended use, is a mixture of fragrance materials possibly together with other ingredients such as, for example, perfume carriers. By the term "perfume carrier", it is meant to include materials which are practically neutral from a perfumery point of view, e.g., which does not significantly alter the organoleptic properties of perfuming components. The perfume carrier may be a compatible liquid or solid fillers, diluents, and the like. The term "compatible", as used herein, means that the components of the compositions of this invention are capable of being combined with the primary actives of the present invention, and with each other, in a manner such that there is no interaction which would substantially reduce the efficacy of the composition under ordinary use situations. The type of carrier utilized in the present invention depends on the type of product desired and may comprise, but are not limited to, solutions, aerosols, emulsions (including oil-in-water or water-in-oil), gels, and liposomes. Preferably, the carrier is a liquid and will be a solvent such as, for example, dipropyleneglycol, diethyl phthalate, isopropyl myristate, benzyl benzoate, 2-(2-ethoxyethoxy)-1-ethanol, or ethyl citrate (triethyl citrate).

In yet another aspect, the compositions for use in the present invention may take any form suitable for use, such as for perfumery or cosmetic use. These include, but are not limited to, vapor sprays, aerosols, emulsions, lotions, liquids, creams, gels, sticks, ointments, pastes, mousses, powders, granular products, substrates, cosmetics (e.g., semi-solid or liquid makeup, including foundations) and the like. In some examples, the compositions for use in the present invention take the form of a vapor spray. Compositions of the present invention can be further added as an ingredient to other compositions, preferably fine fragrance or cosmetic compositions, in which they are compatible. As such they can be used within solid composition or applied substrates etc. Examples of products including the composition can include a fabric care product, an air care product, a home care product, a beauty care product, or a mixture thereof. Specific examples of products can include a perfume, an eau de toilette, an eau de parfum, a cologne, a body splash, a lotion, a cream, a shampoo, a conditioner, a hair mist, a body oil, a deodorant, a solid fragrance, or a body spray. The composition can be contacted with skin, hair, or a fabric.

Article of Manufacture

The composition may be included in an article of manufacture comprising a spray dispenser. The spray dispenser may comprise a vessel for containing the composition to be dispensed. The spray dispenser may comprise an aerosolized composition (e.g., a composition comprising a propellant) within the vessel as well. Other non-limiting examples of spray dispensers include non-aerosol dispensers (e.g., vapor sprays), manually activated dispensers, pump-spray dispensers, or any other suitable spray dispenser available in the art.

Methods of Using the Compositions

The composition of the present invention according to any embodiments described herein is a useful perfuming composition, which can be advantageously used as consumer products intended to perfume any suitable substrate. As used herein, the term "substrate" means any surface to which the composition of the present invention may be applied to without causing any undue adverse effect. For example, this can include a wide range of surfaces including human or animal skin or hair, paper (fragranced paper), air in a room (air freshener or aromatherapy composition), fabric, furnishings, dishes, hard surfaces and related materials. Preferred substrates include body surfaces such as, for example, hair and skin, most preferably skin.

The composition of the present invention may be used in a conventional manner for fragrancing a substrate. An effective amount of the composition, such as from about 1 µL to about 100 mL, preferably from about 10 µL to about 1,000 µL, more preferably from about 25 µL to about 500 µL, from about 50 µL to about 100 µL, from about 100 µL to about 20 mL, or combinations thereof, is applied to the suitable substrate. Alternatively, an effective amount of the composition of the present invention is less than, equal to, or greater than about 1 µL, 10 µL, 25 µL or 50 µL to about 100 µL, 500 µL, 1,000 µL, 10,000 µL, 10 mL, 20 mL, 25 mL, 30 mL, 40 mL, 50 mL, 60 mL, 70 mL, 80 mL, 90 mL, or 100 mL. The composition may be applied by hand or applied utilizing a delivery apparatus such as, for example, vaporizer or atomizer. Preferably, the composition is allowed to dry after its application to the substrate. The scope of the present invention should be considered to cover one or more distinct applications of the composition or the continuous release of a composition via a vaporizer or other type of atomizer.

The present disclosure provides a method for imparting, intensifying, or modifying an odor on human skin or human hair, comprising applying to human skin and/or human hair the composition of the present invention. Examples of notes or characters that can be enhanced include those chosen from a citrus-type note, green-type note, spicy-type note, cinnamon-type notes, pepper-type notes, cumin-type notes, ginger-type notes, floral-type notes, woody-type notes, cedarwood-type notes, sandalwood type notes, vetyver-type notes, leather-type note, smoky-type note, musk-type notes, and mixtures thereof.

Preferably, the fragrance profile or character of the composition of the present invention is detectable by a panel of experts or professional evaluators or individual experts or professional evaluators at later time points such as, for example, 30 mins, 1 hour, 2 hours, 3 hours, 4 hours, 5 hours, 6 hours, 7 hours, 8 hours, 10 hours, and possibly all the way up to 24 hours after application of the composition to a substrate as compared to controls (e.g., those without modulators).

In another aspect, the present invention is also directed to a method of producing a consumer product comprising bringing into contact or mixing into the product an organoleptically active quantity of a composition of the present invention.

Test Methods

The following assays set forth must be used in order that the invention described and claimed herein may be more fully understood.

Test Method 1: Determining Vapor Pressure

In order to determine the vapor pressure for the fragrance materials, go to the website https://scifinder.cas.org/scifinder/view/scifinder/scifinderExplore.jsf and follow these steps to acquire the vapor pressure.
1. Input the CAS registry number for the particular fragrance material.
2. Select the vapor pressure from the search results.
3. Record the vapor pressure (given in Torr at 25° C.).

SciFinder uses Advanced Chemistry Development (ACD/Labs) Software Version 11.02. (©1994-2018). If the CAS number for the particular fragrance material is unknown or does not exist, you can utilize the ACD/Labs reference program to directly determine the vapor pressure. Vapor Pressure is expressed in 1 Torr, which is equal to 0.133 kilopascal (kPa).

Test Method 2a: Olfactory Tests a

In order to show the effect of the substantially non-odorous fragrance modulators and fragrance component of the present invention on the perception of fragrance profile in a composition of the present invention, test compositions are made, as described in the Example section, and given to expert panelists to evaluate.

At the testing facility, 50 µL samples of the compositions and the controls are applied to glass slides and placed on a hot plate at 32° C. to represent skin temperature for varying durations. It is important that glass slides of samples that are to be later compared are prepared at the same time. The panelists are asked to evaluate the perceived fragrance profile (intensity and/or character) of each glass slide sample at a given time point. Slides are presented coded so that their identity is not known by the panelists. Within a given time point panelists evaluate the slides in a random order and are able to revisit their assessment as they work through the slides at that time point. Their assessments are recorded. In the subsequent analysis, the data for strength and character comparisons are drawn from the independent assessments carried out at a given time point. Only when using the character difference scale below are any 2 products physically directly compared to each other. Panelists are selected from individuals who are either trained to evaluate fragrances according to the scales below or who have experience of fragrance evaluation in the industry. Typically, around 4-6 panelists are used to evaluate a given product and its control.

(a) Fragrance Intensity:

The panelists are asked to give a score on a scale of 0 to 5 for perceived fragrance intensity according to the odour intensity scale set out in Table 5 herein below.

TABLE 5

| Odour Intensity Scale | |
| --- | --- |
| Score | Fragrance Intensity |
| 0 | None |
| 1 | Very Weak |

TABLE 5-continued

Odour Intensity Scale

| Score | Fragrance Intensity |
|---|---|
| 2 | Weak |
| 3 | Moderate |
| 4 | Strong |
| 5 | Very Strong |

(b) Fragrance Character:

The panelists are asked to assess the fragrance character in one of 2 ways:
  i) a score on a scale of 0 to 3 for the dominance of particular characters that are relevant to that particular fragrance, e.g.: fresh, harsh, green, watery, floral, rose, muguet, fruity, apple, berry, citrus, creamy, woody, balsamic, amber, musk just to name a few, according to the odour grading scale set out in Table 6(i) herein below;
  ii) a score on a scale of 1 to 5 for changes in the perceived fragrance profile change for the test compositions versus the controls according to the odour grading scale set out in Table 6(ii) herein below.

TABLE 6(i)

Character Dominance Odour Grading Scale

| Score | Fragrance Character Dominance |
|---|---|
| 0 | Not noticeable |
| 1 | Slight presence of the character |
| 2 | Moderate presence of the character |
| 3 | Dominance of the character |

TABLE 6(ii)

Character Difference Odour Grading Scale

| Score | Fragrance Profile Change |
|---|---|
| 1 | Fragrance profile is unchanged, i.e., no difference between the sample vs. the control. |
| 2 | Slight fragrance profile change when compared directly with the control. |
| 3 | Moderate fragrance profile but similar character to the control. |
| 4 | Large difference in fragrance profile from the control. |
| 5 | Total difference in the fragrance profile from the control. |

The results of the panelists are averaged and if sufficient panelists are available, typically around 10, then the data can be analyzed using Analysis of Variance methods. The model treats the subject as a random effect and looks at the impact of product, time and the interaction between product and time. From the analysis the least square means for the product and time interaction are obtained. These means (as well as their confidence intervals) are then plotted to enable comparisons between products at each time point. It should be noted that the confidence levels plotted are intended as a guide, and not as a statistical comparison, as they do not take into account that multiple testing has been performed. As well as a graphical assessment, statistical comparisons between the two products at each of the time points are performed with a Sidak correction for multiple comparisons. The p-values for the product differences are obtained, with p-values <0.05 indicating a statistical difference between the two products at 5% significance (or 95% confidence). Typically for assessments by expert panelists of evaluators and perfumers there are 4-6 participants. In these cases a full statistical analysis is not possible and typically we observe that an average difference of 0.75 on the scales used considered to be meaningful, i.e.: 3 out of 4 experts gave the products a grade with a difference of 1.

Test Method 2b: Olfactory Tests b

In order to show the effect of the substantially non-odorous fragrance modulators and fragrance component on the perception of fragrance profile in a composition of the present invention, test compositions are made, as described in the Example section, and given to panelists to evaluate and describe.

At the testing facility, 20 µL samples of the compositions and the controls are applied to glass slides and placed on a hot plate at 32° C. to represent skin temperature for varying durations. Glass slides of samples that are to be later compared are prepared at the same time. The panelists are asked to evaluate the perceived fragrance profile (intensity and/or character) of each glass slide sample at a given time point. Slides are presented coded so that their identity is not known by the panelists. Within a given time point, panelists evaluate the slides in a random order and are able to revisit their assessment as they work through the slides at that time point. Their assessments are recorded. The experiments are run in duplicate on 2 different days and the data combined. In the subsequent analysis, the data for strength and character comparisons are drawn from the independent assessments carried out at a given time point.

Panelists are individuals who are specifically trained to evaluate fragrances according to the scale below using odour standards for calibration. Calibration standards are selected from perfume materials that represent specific families, for example, without being exhaustive, for the woody family panelists are calibrated with cedarwood, vetivert oil, patchouli oil, iso-E super, Norlimbanol and sandalwood or for harshness, for example, without being exhaustive, panelists are calibrated with pyrazines, Vertocitral, Aldehyde phenylacetic, Cedar Atlas and Cuminic aldehyde. Around 10-15 panelists are used to evaluate a given product and its control. Panelists assess the samples according to 2 scales:

(a) Fragrance Intensity:

The panelists give a score on a unlabeled continuous scale where 0 is no perceptible odour and 10 is very strong odour.

(b) Fragrance Character:

The panelists assess the fragrance character according to a number of pre-defined attributes e.g.: citrus, green, aromatic, floral, fruity, spicy, musk, woody, fresh, harsh just to name a few, scoring each one on unlabeled continuous scale where 0 is no perceptible odor and 10 is very strong odor.

The results of the panelists are analyzed using three-way analysis of variance (replicate/sample/panellist) with interaction followed by multiple comparisons with the best or control test (MCB) for example, the two-tailed Dunnett test. The p-values for the product differences are obtained, with p-values <0.05 indicating a statistical difference between products at 5% significance (or 95% confidence) and with p-values <0.10 indicating a statistical difference between products at 10% significance (or 90% confidence). The data is represented graphically in bar or line charts showing the average for each attribute at a given time point with 95% confidence intervals as error bars.

Data generated according to this method, particularly for the harshness attribute, is discussed below.

EXAMPLES

Example 1—Fragrance Oils

Fragrance examples 1, 2, 3 and 4 3 are provided below in Tables 7-11, respectively, as non-limiting examples of formulations of fragrance materials intended to form the fragrance component of the compositions of the present invention.

The following fragrance formulations are made by mixing the listed ingredients in the listed proportions (wt %) at room temperature, wherein the wt % is relative to the total weight of the fragrance component.

TABLE 7

Fragrance Example 1

| CAS Number | Perfume Material | Parts (Weight %) Example 1 | Vapour Pressure (Torr at 25° C.) | Volatility |
|---|---|---|---|---|
| Natural | Styrax Resoid | 0.500-0.520 | — | High |
| Natural | Labdanum Cistus Absolute | 0.4400-0.4700 | 3.48900 | High |
| 3681-71-8 | cis-3-Hexenyl acetate | 0.1000-0.1050 | 1.21900 | High |
| 928-96-1 | BETA GAMMA HEXENOL | 0.1000-0.1050 | 1.03900 | High |
| 68039-49-6 | LIGUSTRAL OR TRIPLAL | 0.2000-0.2080 | 0.57800 | High |
| Natural | Cumin Oil | 0.2000-0.2080 | — | High |
| 88-41-5 | Verdox | 0.5000-0.5300 | 0.10300 | High |
| Natural | Cade Oil | 1.5490-1.5600 | — | Moderate |
| 58567-11-6 | BOISAMBRENE FORTE | 5.1000-5.2000 | 0.00433 | Moderate |
| 65442-31-1 | ISO BUTYL QUINOLINE | 0.1500-0.1600 | 0.00408 | Moderate |
| 127-51-5 | IONONE GAMMA METHYL | 20.7000-20.7900 | 0.00282 | Moderate |
| 211299-54-6 | AMBROCENIDE (add as 10% in DPG) | 0.0400-0.0450 | 0.00182 | Moderate |
| 91-64-5 | Coumarin | 25.9000-26.0000 | 0.00130 | Moderate |
| Natural | Cedarwood Texas Light | 25.9000-26.0000 | — | Low |
| Natural | Cypriol Oil | 10.3907 10.3000-10.4000 | — | Low |
| Natural | Guaiacwood Oil | 5.1000-5.2000 | — | Low |
| 4707-47-5 | LRG 201/Evernyl | 2.5000-2.6000 | 0.00001 | Low |
| | Total | 100.00 | | |

Oil Structure:
2.1% high volatile perfume materials;
53.7% moderate volatile perfume materials;
44.2% low volatile perfume materials.

TABLE 8

Fragrance Example 2

| CAS Number | Perfume Material | Parts (Weight %) Example 2 | Vapour Pressure (Torr at 25° C.) | Volatility |
|---|---|---|---|---|
| Natural | Styrax Resoid | 1.000-1.100 | — | High |
| Natural | Labdanum Absolute | 0.900-0.950 | — | High |
| 3681-71-8 | cis-3-Hexenyl acetate | 0.200-0.230 | 1.21900 | High |
| 928-96-1 | BETA GAMMA HEXENOL | 0.200-0.230 | 1.03900 | High |
| 68039-49-6 | LIGUSTRAL OR TRIPLAL | 0.400-0.420 | 0.57800 | High |
| Natural | Cumin Oil | 0.400-0.420 | — | High |
| Natural | Cade Oil (supplied at 0.01% DPG) | 0.050-0.053 | — | High |
| 88-41-5 | Verdox | 0.000-1.040 | 0.10300 | High |
| 22471-55-2 | Thesaron | 0.700-0.730 | 0.07670 | Moderate |
| 144-39-8 | Linalyl Propionate | 1.030-1.040 | 0.02630 | Moderate |
| 105-87-3 | Geranyl Acetate | 1.200-1.300 | 0.02560 | Moderate |
| 2785-89-9 | 4-Ethylguaiacol | 0.200-0.230 | 0.02000 | Moderate |
| 54440-17-4 | Safraleine | 2.060-2.070 | 0.01260 | Moderate |
| 104-54-1 | Cinnamic Alcohol | 0.510-0.520 | 0.01170 | Moderate |
| 97-53-0 | Eugenol | 0.000-1.040 | 0.01040 | Moderate |
| 6790-58-5 | Ambronat | 6.100-6.300 | 0.00934 | Moderate |
| 104-61-0 | NONALACTONE | 0.700-0.800 | 0.00858 | Moderate |
| 18871-14-2 | Jasmal | 2.000-2.100 | 0.00434 | Moderate |
| 65442-31-1 | ISO BUTYL QUINOLINE | 0.500-0.530 | 0.00408 | Moderate |
| 107-75-5 | HYDROXYCITRONELLAL | 2.000-2.100 | 0.00318 | Moderate |
| 127-51-5 | IONONE GAMMA METHYL | 15.000-16.000 | 0.00282 | Moderate |
| 33704-61-9 | Cashmeran | 2.500-2.600 | 0.00269 | Moderate |

TABLE 8-continued

Fragrance Example 2

| CAS Number | Perfume Material | Parts (Weight %) Example 2 | Vapour Pressure (Torr at 25° C.) | Volatility |
|---|---|---|---|---|
| 36306-87-3 | Kephalis | 5.100-5.200 | 0.00269 | Moderate |
| 77-54-3 | Cedac/CEDRYL ACETATE S | 7.700-7.800 | 0.00192 | Moderate |
| 91-64-5 | Coumarin | 2.500-2.600 | 0.00130 | Moderate |
| 24851-98-7 | METHYL DIHYDRO JASMONATE | 4.130-4.140 | 0.00071 | Low |
| 65113-99-7 | Sandalore | 5.100-5.190 | 0.00063 | Low |
| Natural | Cedarwood Oil Rect | 1.000-1.400 | — | Low |
| Natural | Vetivert Oil | 2.000-2.100 | — | Low |
| 77-53-2 | Cedrol Crude | 4.100-4.200 | 0.00057 | Low |
| 54464-57-2 | Iso E Super | 12.200-12.500 | 0.00054 | Low |
| Natural | PATCHOULI OIL | 6.100-6.300 | — | Low |
| 65405-77-8 | cis-3-Hexenyl salicylate | 2.000-2.100 | 0.00025 | Low |
| 4940-11-8 | ETHYL MALTOL (supplied at 10% in DPG) | 0.150-0.160 | 0.00023 | Low |
| 4707-47-5 | LRG 201/Evernyl | 1.030-1.040 | 0.00001 | Low |
| 28645-51-4 | Ambrettolide | 5.100-5.120 | 0.000001 | Low |
| | Total | 100.00 | | |

Oil Structure:
4.3% high volatile perfume materials;
52.1% moderate volatile perfume materials;
43.6% low volatile perfume materials.

TABLE 9

Fragrance Example 3

| CAS Number | Perfume Material | Parts (Weight %) Example 3 | Vapour Pressure (Torr at 25° C.) | Volatility |
|---|---|---|---|---|
| Natural | Basil Oil | 0.440-0.470 | — | High |
| Natural | Cardamom Oil | 0.180-0.190 | — | High |
| Natural | Cypress Oil | 0.225-0.235 | — | High |
| Natural | Ginger Oil India | 0.180-0.190 | — | High |
| Natural | Bergamot Oil | 4.600-4.670 | — | High |
| Natural | Lemon Oil | 4.100-4.180 | — | High |
| Natural | Violet Leaves Absolute | 0.040-0.050 | — | High |
| 39255-32-8 | Manzanate | 0.040-0.050 | 2.90600 | High |
| 3681-71-8 | cis-3-Hexenyl acetate | 0.040-0.050 | 1.21900 | High |
| 928-96-1 | BETA GAMMA HEXENOL | 0.130-0.142 | 1.03900 | High |
| 67633-96-9 | Liffarome | 0.090-0.100 | 0.72100 | High |
| 68039-49-6 | LIGUSTRAL OR TRIPLAL | 0.040-0.050 | 0.57800 | High |
| 18479-58-8 | DIHYDRO MYRCENOL | 9.350-9.500 | 0.16600 | High |
| 88-41-5 | verdox | 0.900-8.100 | 0.10300 | High |
| Natural | Rose Oil | 0.040-0.050 | — | Moderate |
| Natural | Lavandin Oil | 0.690-0.700 | — | Moderate |
| Natural | Geranium Oil | 0.090-0.100 | — | Moderate |
| Natural | Cedar Atlas | 5.075-5.095 | — | Moderate |
| 78-70-6 | Linalool | 1.600-1.650 | 0.09050 | Moderate |
| 60-12-8 | Phenyl Ethyl Alcohol | 0.200-0.250 | 0.07410 | Moderate |
| 67634-00-8 | Allyl Amyl Glycolate | 0.400-0.430 | 0.04000 | Moderate |
| 125109-85-5 | Florhydral | 0.265-0.280 | 0.02000 | Moderate |
| 134-20-3 | methyl Anthranilate | 0.040-0.050 | 0.01580 | Moderate |
| 150-84-5 | Citronellyl acetate | 0.040-0.050 | 0.01370 | Moderate |
| 68845-00-1 | Boisiris | 3.690-3.710 | 0.01350 | Moderate |
| 106-24-1 | geraniol | 0.900-0.950 | 0.01330 | Moderate |
| 19870-74-7 | CEDRYL METHYL ETHER | 5.070-5.095 | 0.01280 | Moderate |
| 120-57-0 | heliotropin | 0.040-0.050 | 0.01040 | Moderate |
| 3025-30-7 | Ethyl, 2 4-Decadienoate | 0.130-0.141 | 0.00954 | Moderate |
| 6790-58-5 | Ambronat | 0.680-0.700 | 0.00930 | Moderate |
| 2705-87-5 | Allyl Cyclohexane Propionate | 0.210-0.240 | 0.00925 | Moderate |
| 56973-85-4 | Neobutenone, α | 0.130-0.140 | 0.00763 | Moderate |
| 63500-71-0 | florol | 2.200-2.350 | 0.00557 | Moderate |
| 10339-55-6 | Ethyl Linalool | 10.560-10.600 | 0.00520 | Moderate |
| 23696-85-7 | Damascenone | 0.077-0.081 | 0.00503 | Moderate |
| 58567-11-6 | BOISAMBRENE FORTE | 3.650-3.750 | 0.00433 | Moderate |
| 93-29-8 | Iso Eugenol Acetate | 0.085-0.095 | 0.00324 | Moderate |
| 476332-65-7 | AMBER XTREME (supplied at 10% in DPG) | 0.008-0.010 | 0.00323 | Moderate |

TABLE 9-continued

Fragrance Example 3

| CAS Number | Perfume Material | Parts (Weight %) Example 3 | Vapour Pressure (Torr at 25° C.) | Volatility |
|---|---|---|---|---|
| 68901-15-5 | Cyclo Galbanate | 0.220-0.240 | 0.00323 | Moderate |
| 127-51-5 | IONONE GAMMA METHYL | 0.900-0.990 | 0.00282 | Moderate |
| 1205-17-0 | helional | 1.800-1.900 | 0.00270 | Moderate |
| 33704-61-9 | Cashmeran | 0.900-0.950 | 0.00269 | Moderate |
| 141-13-9 | Adoxal | 0.200-0.250 | 0.00257 | Moderate |
| 121-33-5 | vanillin | 0.400-0.480 | 0.00194 | Moderate |
| 91-64-5 | Coumarin | 1.150-1.160 | 0.00130 | Moderate |
| Natural | Vetivert Oil | 1.800-1.900 | — | Low |
| 28940-11-6 | Calone | 0.040-0.050 | 0.00083 | Low |
| 70788-30-6 | Norlimbanol | 0.680-0.700 | 0.00047 | Low |
| 1222-05-5 | Galaxolide | 11.300-11.500 | 0.00041 | Low |
| 65405-77-8 | cis-3-Hexenyl salicylate | 2.300-2.350 | 0.00025 | Low |
| 107898-54-4 | Polysantol | 3.200-3.300 | 0.00012 | Low |
| 82356-51-2 | delta muscenone | 0.900-0.930 | 0.00005 | Low |
| 21145-77-7 | Tonalid | 0.900-0.930 | 0.00003 | Low |
| 4707-47-5 | LRG 201/Evernyl | 0.300-0.340 | 0.00001 | Low |
| | Total | 100.00 | | |

Oil Structure:
27.8% high volatile perfume materials;
42.1% moderate volatile perfume materials;
30.1% low volatile perfume materials.

TABLE 10

Fragrance Example 4

| CAS Number | Perfume Material | Parts (Weight %) | Vapour Pressure (Torr at 25° C.) | Volatility |
|---|---|---|---|---|
| Natural | Elemi Coeur Oil | 1.250-1.750 | | High |
| 928-96-1 | BETA GAMMA HEXENOL | 0.0500-0.1500 | 1.03900 | High |
| 68039-49-6 | LIGUSTRAL OR TRIPLAL | 0.0500-0.1500 | 0.57800 | High |
| Natural | Cinnamon Bark Oil | 3.500-4.500 | | Moderate |
| 6790-58-5 | Ambronat | 4.500-5.500 | 0.00934 | Moderate |
| 24720-09-0 | ALPHA DAMASCONE | 0.500-1.500 | 0.00830 | Moderate |
| Natural | Cedar Atlas Oil | 47.000-49.000 | | Moderate |
| Natural | Ginger Oil Fresh Madagascar | 2.500-3.500 | | Moderate |
| 77-53-2 | Cedrol Crude | 14.000-16.000 | 0.00057 | Low |
| 70788-30-6 | Norlimbanol | 2.800-3.200 | 0.00047 | Low |
| 95962-14-4 | Nectaryl | 7.000-7.500 | 0.00037 | Low |
| 82356-51-2 | Delta Muscenone | 11.000-13.000 | 0.00005 | Low |

Oil Structure:
1.7% high volatile perfume materials;
61.0% moderate volatile perfume materials;
37.3% low volatile perfume materials.

Example 2—Compositions Comprising Fragrance Oils and Substantially Non-Odorous Fragrance Modulators Compositions A1, $C_1$, E1, G1, I1 and A2, $C_2$, E2, G2 and I2 are examples of fragrance compositions according to the present invention, made with any one of fragrance oil examples 1-4 respectively. In parallel, control compositions B1, D1, F1, H1, J1 and B2, D2, F2, H2, J2 are prepared by replacing the different substantially non-odorous fragrance modulators by the same amount of deionized water. All of the compositions are prepared by admixture of the components described in Table 11 and 12 in the proportions indicated.

TABLE 11

Fragrance Compositions

Fragrance Composition (wt %)[1]

| Ingredients | A1 | B1 | C1 | D1 | E1 | F1 | G1 | H1 | I1 | J1 |
|---|---|---|---|---|---|---|---|---|---|---|
| Bottom heavy fragrance oil[2] | 5-10 | 5-10 | 0.01-2 | 0.01-2 | 3-10 | 3-10 | 5-10 | 5-10 | 0.1-5 | 0.1-5 |

TABLE 11-continued

Fragrance Compositions

| Ingredients | A1 | B1 | C1 | D1 | E1 | F1 | G1 | H1 | I1 | J1 |
|---|---|---|---|---|---|---|---|---|---|---|
| Ethanol | | | | | 60-99.9 | | | | | |
| Butylated Hydroxy Toluene | | | | | 0-0.07 | | | | | |
| Modulator A[3] | 2-20 | — | — | — | — | — | — | — | — | — |
| Modulator B[4] | — | — | 0.1 | — | — | — | — | — | — | — |
| Modulator C[5] | — | — | — | — | 0.1-5 | — | — | — | — | — |
| Modulator D[6] | — | — | — | — | — | — | 2-10 | — | — | — |
| Modulator E[7] | — | — | — | — | — | — | — | — | 0.1-3 | — |
| Deionized water | | | | | to 100.00 | | | | | |

[1] Wt % is relative to the total weight of the composition.
[2] Can be any one of fragrance examples 1-4
[3] Can be any one of the substantially non-odorous fragrance modulators examples: sucrose laurate; sucrose dilaurate, sucrose myristate, sucrose palmitate, sucrose sterate; sucrose 5 distearate; or sucrose tristearate.
[4] Substantially non-odorous fragrance modulator is (E)-1-2,6-trimethylcyclohexyl)oct-1-en-3-one.
[5] Can be any one of the substantially non-odorous fragrance modulators examples: 2-(1-menthoxy) ethane-1-ol; 1-(1-menthoxy) propane-2-ol; 3-(1-menthoxy) propane-1-ol; 3(1-10 menthoxy) propane-1,2-diol; 2-methyl-3-(1-menthoxy)propane-1,2-diol; or 4-(1-menthoxy) butane-1-ol.
[6] Substantially non-odorous fragrance modulator is Hydroquinone beta-D-glycoside.
[7] Substantially non-odorous fragrance modulator is Hyaluronic acid disaccharide sodium salt or Sodium Hyaluronate (20-50 kDa).

TABLE 12

Fragrance Compositions

| Ingredients | A2 | B2 | C2 | D2 | E2 | F2 | G2 | H2 | I2 | J2 |
|---|---|---|---|---|---|---|---|---|---|---|
| Bottom heavy fragrance oil[2] | 5-10 | 5-10 | 5-15 | 5-15 | 2.5-10 | 2.5-10 | 5-20 | 5-20 | 0.1-20 | 0.1-20 |
| Ethanol | | | | | 60-99.9 | | | | | |
| Butylated Hydroxy Toluene | | | | | 0-0.07 | | | | | |
| Modulator A[3] | 5-20 | — | — | — | — | — | — | — | — | — |
| Modulator B[4] | — | — | 0.5-5 | — | — | — | — | — | — | — |
| Modulator C[5] | — | — | — | — | 0.1-3.0 | — | — | — | — | — |
| Modulator D[6] | — | — | — | — | — | — | 2.5-15 | — | — | — |
| Modulator E[7] | — | — | — | — | — | — | — | — | 0.1-20 | — |
| Deionized water | | | | | to 100.00 | | | | | |

[1] Wt % is relative to the total weight of the composition.
[2] Can be any one of fragrance examples 1-4?
[3] Can be any one of the substantially non-odorous fragrance modulators examples: Propylene Glycol Propyl Ether, Hexaethylene glycol monododecyl ether, Panthenol Ethyl Ether, DL-Panthenol, Diisobutyl Adipate, or Diisoamyl Adipate.
[4] Neopentyl Glycol Diisononanoate.
[5] 2-ethylhexyloxypropanediol.
[6] PPG-11 Stealyl Ether.
[7] Can be any one of the substantially non-odorous fragrance modulators examples: Dicetyl Ether; Polyglycerin-4 Ethers; Isoceteth-5; Isoceteth-7, Isoceteth-10; Isoceteth-12; Isoceteth-15; Isoceteth-20; Isoceteth-25; Isoceteth-30; Disodium Lauroamphodipropionate; Hexaethylene glycol monododecyl ether; or Cetearyl Ethylhexnoate.

Composition A3 is an example of a fragrance composition according to the present invention, made with any of the fragrance examples 1-4, respectively. In parallel, a control composition B3 is prepared by replacing the different substantially non-odorous fragrance fixative by the same amount of deionized water. All of the compositions are prepared by admixture of the components described in Table 13 in the proportions indicated.

TABLE 13

Fragrance Composition

| Ingredients | A3 | B3 |
|---|---|---|
| Bottom heavy fragrance oil[2] | 2-15 | 2-15 |
| Ethanol | | 60-99.99 |

TABLE 13-continued

Fragrance Composition

| Ingredients | A3 | B3 |
|---|---|---|
| Butylated Hydroxy Toluene | | 0-0.07 |
| Modulator A[3] | 0.1-20 | — |
| Deionized water | | to 100.00 |

[1] Wt % is relative to the total weight of the composition.
[2] Can be any one of fragrance examples 1-4
[3] Can be any one of the substantially non-odorous fragrance modulator as disclosed in Table 4(a) and 4(b).

Compositions A4, C4, E4, and G4 are examples of fragrance compositions according to the present invention, made with any one of fragrance oil examples 1-4, respectively. In parallel, control compositions B4, D4, F4, and H4 are prepared by replacing the different substantially non-odorous fragrance modulators by the same amount of deionized water. All of the compositions are prepared by admixture of the components described in Table 14 in the proportions indicated.

TABLE 14

Fragrance Compositions

| Ingredients | Fragrance Composition (wt %)[1] | | | | | | | |
|---|---|---|---|---|---|---|---|---|
| | A4 | B4 | C4 | C4 | E4 | F4 | G4 | H4 |
| Bottom heavy fragrance oil[2] | 5-9 | 5-9 | 5-9 | 5-9 | 5-9 | 5-9 | 5-9 | 5-9 |
| Ethanol | | | | 75 | | | | |
| Butylated Hydroxy Toluene | | | | 0-0.07 | | | | |
| PPG-20 Methyl Glucose Ether[3] | 13-17 | 0 | — | — | — | — | — | — |
| Caprytyl/Capryl Glucoside[4] | — | — | 13-17 | 0 | — | — | — | — |
| Undecyl Glucoside[5] | 5 | — | — | — | — | 13-17 | 0 | — |
| Isocetyl Aclohol[6] | — | — | — | — | — | — | 13-17 | 0 |
| Deionized water | | | | to 100.00 | | | | |

[1]Wt % is relative to the total weight of the composition.
[2]Can be any one of fragrance examples 1-4.
[3]Available as GLUCAM™ P-20.
[3]Available as Plantacare ® 810 UP.
[3]Available as Simulsol ® SL 11W.
[6]Available as Ceraphy ® ICA.

Example 3—Exemplary Product Compositions

Compositions I, II, III and IV are examples of body spray compositions according to the present invention. They are prepared by admixture of the components described in Table 15, in the proportions indicated.

TABLE 15

Body Spray Compositions

| Ingredients | CAS Number | Compositions (wt % 1) | | | |
|---|---|---|---|---|---|
| | | I | II | III | IV |
| Denatured Ethanol | 64-17-5 | 38.00-40.00 | 58.00-60.00 | 38.00-40.00 | 38.00-40.00 |
| Water | 7732-18-5 | — | 0.50-0.80 | — | — |
| Dipropylene Glycol | 25265-71-8 | 13.00-17.00 | — | 13.00-17.00 | 13.00-17.00 |
| Isopropyl Myristate | 110-27-0 | 0.50-1.50 | — | 0.50-1.50 | 0.50-1.50 |
| Zinc Phenosulphonate | 127-82-2 | 0.25-0.75 | — | 0.25-0.75 | 0.25-0.75 |
| Cavasol ® W7 methylated Beta-cyclodextrin | 128446-36-6 | — | 0.50-1.50 | — | — |
| Fragrance [2] | — | 1.10-1.30 | 1.10-1.30 | 1.10-1.30 | 11.10-1.3020 |
| Fragrance Modulator [3] | — | 2.40-2.80 | 2.40-2.80 | 2.40-2.80 | 2.40-2.80 |
| Propane | 74-98-6 | 4.70-4.90 | — | 4.70-4.90 | 4.70-4.90 |
| Isobutane | 72-28-5 | 26.00-28.00 | — | 26.00-28.00 | 26.00-28.00 |
| 1,1-Difluoroethane (HFC-152a) | 75-37-6 | 7.00-9.00 | 33.00-37.00 | 7.00-9.00 | 7.00-9.00 |
| Total | | 100.00 | 100.00 | 100.00 | 100.00 |

[1] wt % relative to the total weight of the composition.
[2] Can be any one of Fragrances Examples 1-4.
[3] Can be any one of the substantially non-odorous fragrance modulators disclosed in Tables 4(a) and 4(b).

Composition V, VI and VII are examples of body lotion compositions according to the present invention. They are prepared by admixture of the components as described in Table 16, in the proportions indicated.

TABLE 16

Body Lotion Composition

| Ingredients | CAS Number | Compositions (wt % [1]) | | |
|---|---|---|---|---|
| | | V | VI | VII |
| Water | 7732-18-5 | qsp 100% | qsp 100% | qsp 100% |
| Trilon ® B | 64-02-8 | 0.02-0.07 | 0.02-0.07 | 0.02-0.07 |
| Carbopol ® ETD 2050 | 9003-01-4 | 0.1-0.3 | 0.1-0.3 | 0.1-0.3 |
| Pemulen ™ TR1 | 9063-87-0 | 0.1-0.3 | 0.1-0.3 | 0.1-0.3 |
| Nexbase ® 2008 | 68037-01-4 | 7-9 | 7-9 | 7-9 |
| Silicone V100 | 63148-62-9 | 5-7 | 5-7 | 5-7 |
| Fragrance Modulator [3] | — | 2-4 | 2-4 | 2-4 |
| Tris Amino ™ Ultra Pur | 102-71-6 | 0.2-0.6 | 0.2-0.6 | 0.2-0.6 |
| Fragrance [2] | — | 2-4 | 2-4 | 2-4 |
| Preservatives | — | qs | qs | qs |
| Total | | 100.00 | 100.00 | 100.00 |

[1] wt % relative to the total weight of the composition.
[2] Can be any one of the Fragrances Examples 1-4.
[3] Can be any one of the substantially non-odorous fragrance modulators disclosed in Tables 4(a) and 4(b).

Example 5: Results from Test Method 2a

Data obtained for fragrance constructions that include Glucam P-20 modulator as well corresponding fragrance constructions that are free of a modulator is presented in FIGS. 1-5.

As shown in FIG. 1, in Fragrance Composition A4 including Oil Example 1 (denoted by "Glucam") the inclusion of Glucam P-20 reduces the harshness, the unpleasant solvent and earthy green notes associated with the overdose of powerful perfume materials as compared to Fragrance Composition B4 including Oil Example 1 (denoted by "NIL").

Figure 2:
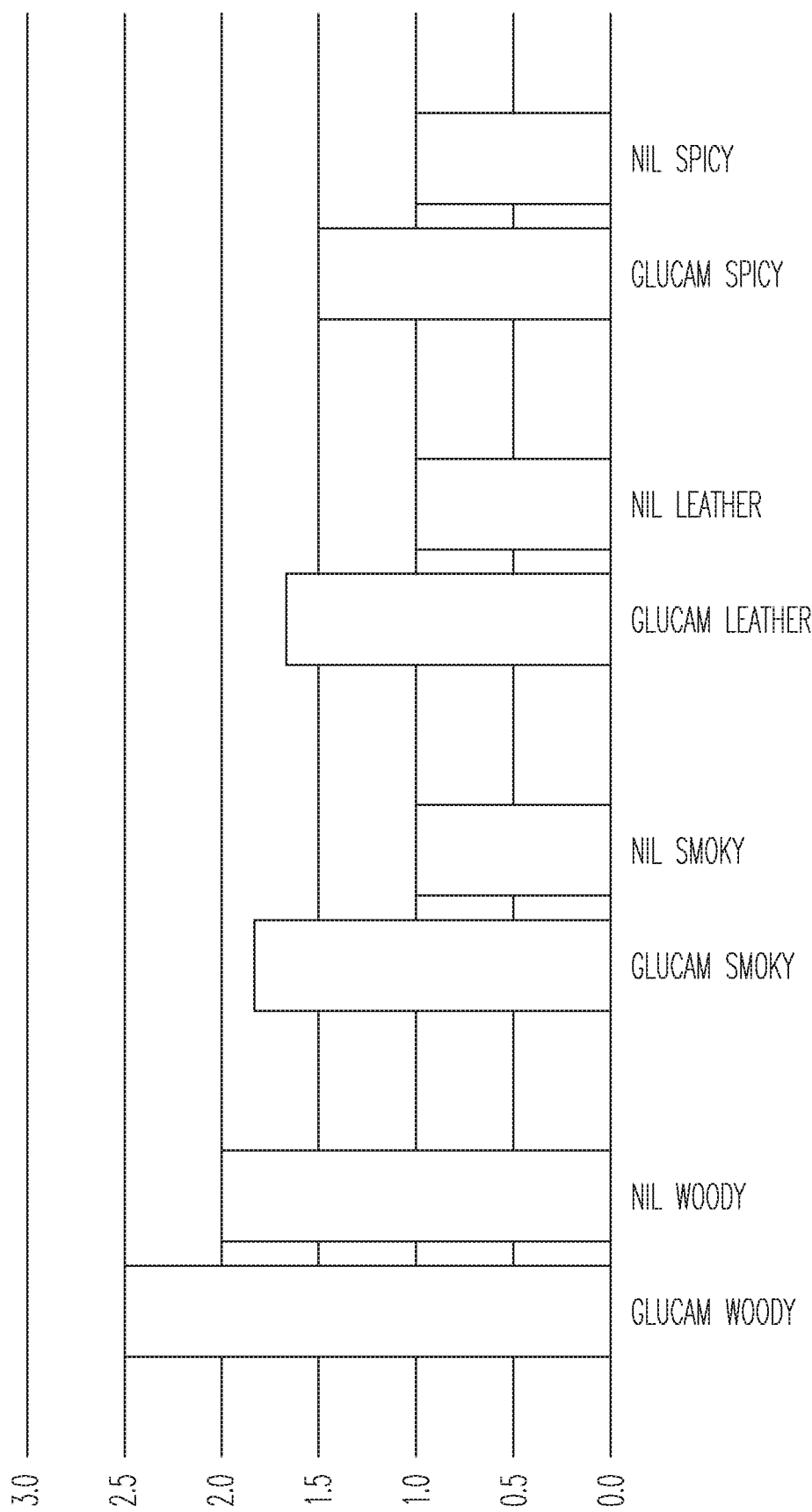
FIG. 2 shows a profile of fragrance materials in a fragrance construction according to the instant disclosure.

As shown in FIG. 2, in Fragrance Composition A4 including Oil Example 1 (denoted by "Glucam") the inclusion of Glucam P-20 increases the perception of base note characters of woody, smoky, leather and spicy notes as compared to Fragrance Composition B4 including Oil Example 1 (denoted by "NIL").

Figure 3:
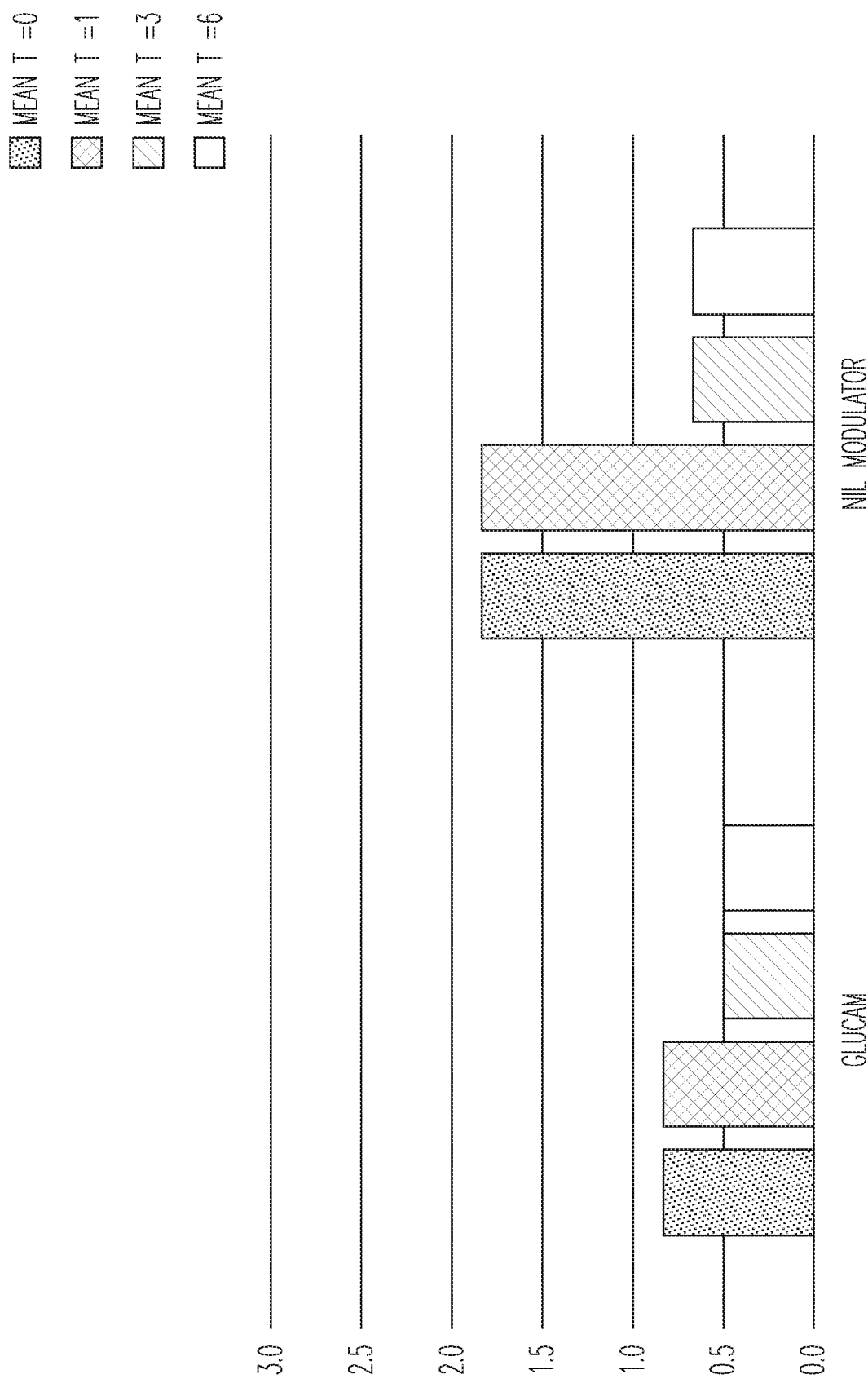
FIG. 3 shows a profile of fragrance materials in a fragrance construction according to the instant disclosure.
Figure 4:
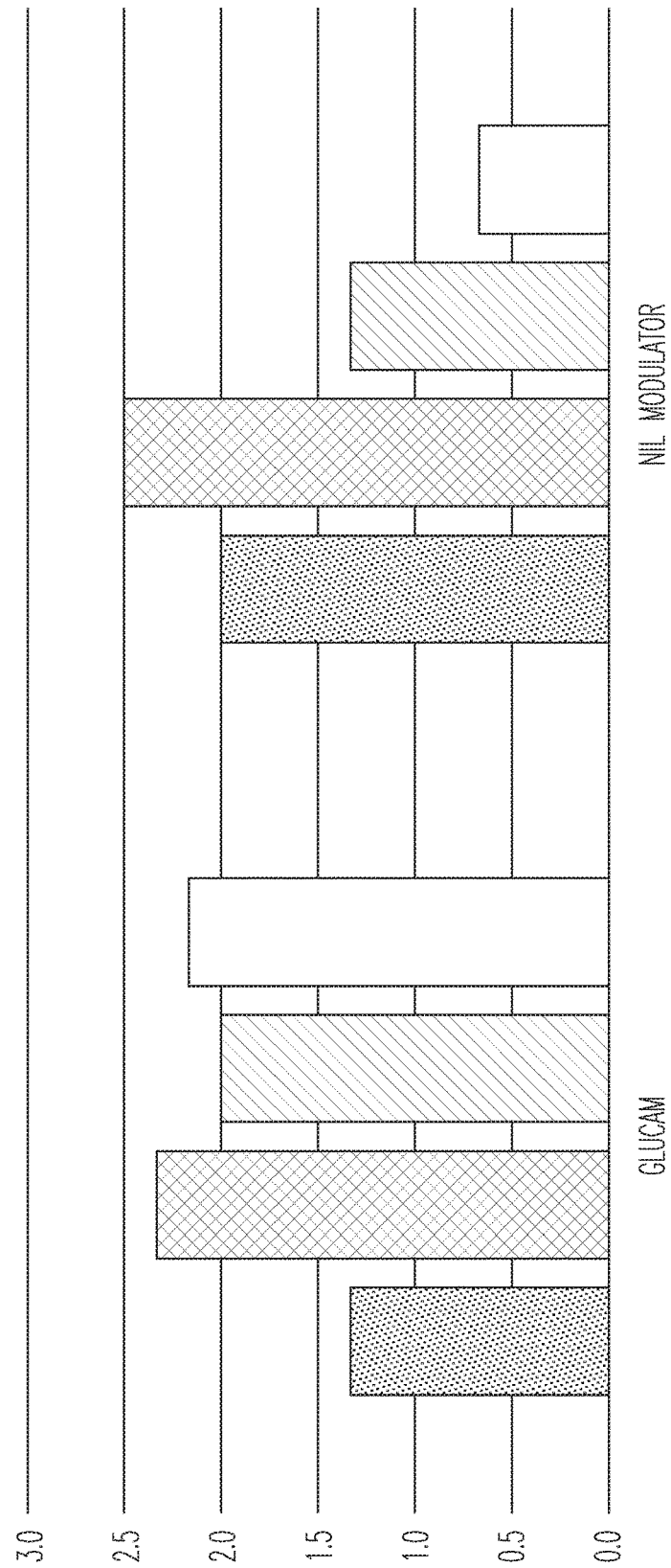
FIG. 4 shows a profile of fragrance materials in a fragrance construction according to the instant disclosure.
Figure 5:
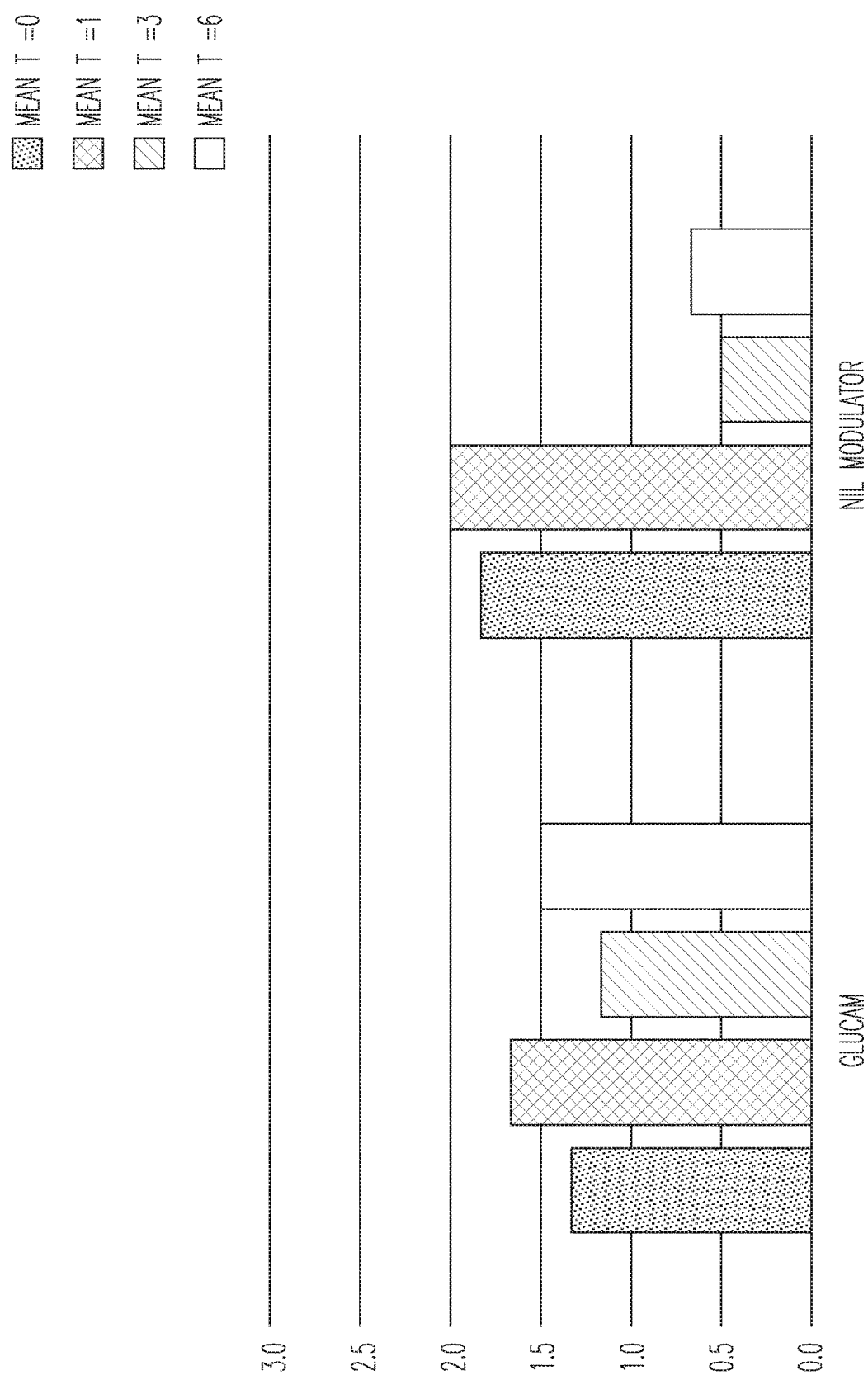
FIG. 5 shows a profile of fragrance materials in a fragrance construction according to the instant disclosure.

As shown in FIGS. 3-5, in Fragrance Composition A4 including Oil Example 2 (denoted by "Glucam") the inclusion of Glucam P-20 reduces the initial and 1 hour perceived harshness due to the overdose of powerful fragrance materials. Inclusion of Glucam P-20 also maintains the earth and green notes over time creating a more complex base note character as compared to corresponding Fragrance Composition B4 including Oil Example 2 (denoted by "Nil Modulator") that is free of Glucam P-20 or any modulator. FIG. 3 shows harshness, FIG. 4 shows earthy character, and FIG. 5 shows green character.

Figure 6:
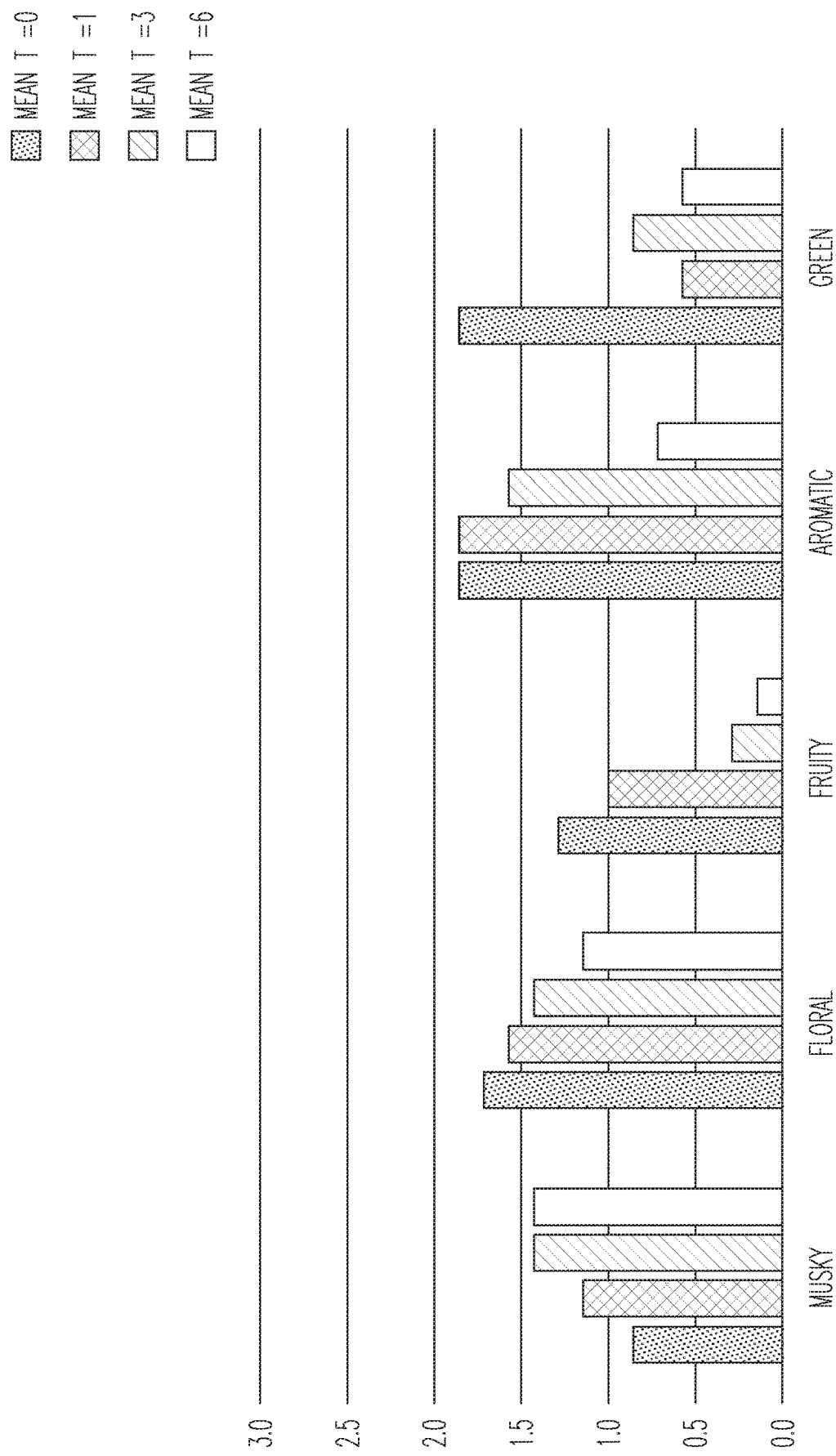
FIG. 6 shows a profile of fragrance materials in a fragrance construction according to the instant disclosure.
Figure 7:
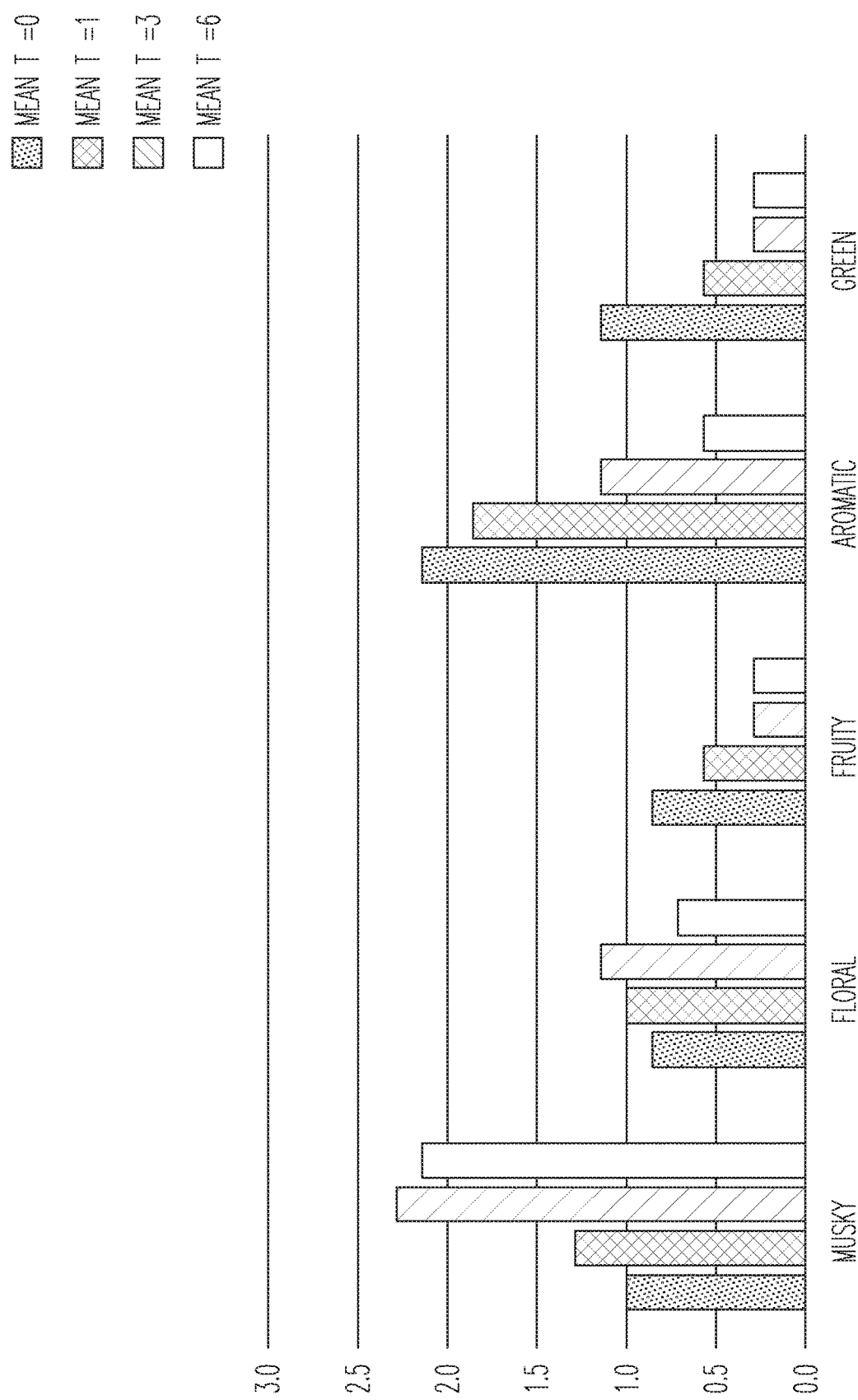
FIG. 7 shows a profile of fragrance materials in a fragrance construction according to the instant disclosure.

As shown in FIGS. 6-7, the inclusion of Glucam P-20 in Fragrance Composition A4 including Oil Example 3 (denoted by "Glucam") can help to present a strong initial perception of a complex blend of floral, aromatic, and green notes. This is shown in FIG. 6. FIG. 7 shows the character of the fragrance that is free of Glucam P-20 or any modulator which is initially dominated by mainly aromatic notes. Over time the floral and aromatic notes are maintained with the inclusion of Glucam P-20 but in the corresponding Fragrance Composition B4 including Oil Example 3 (denoted by "Nil Modulator") that is free of Glucam P-20 or any modulator the floral and aromatic notes are not maintained to the same extent and the character is dominated by musk notes.

Figure 8:
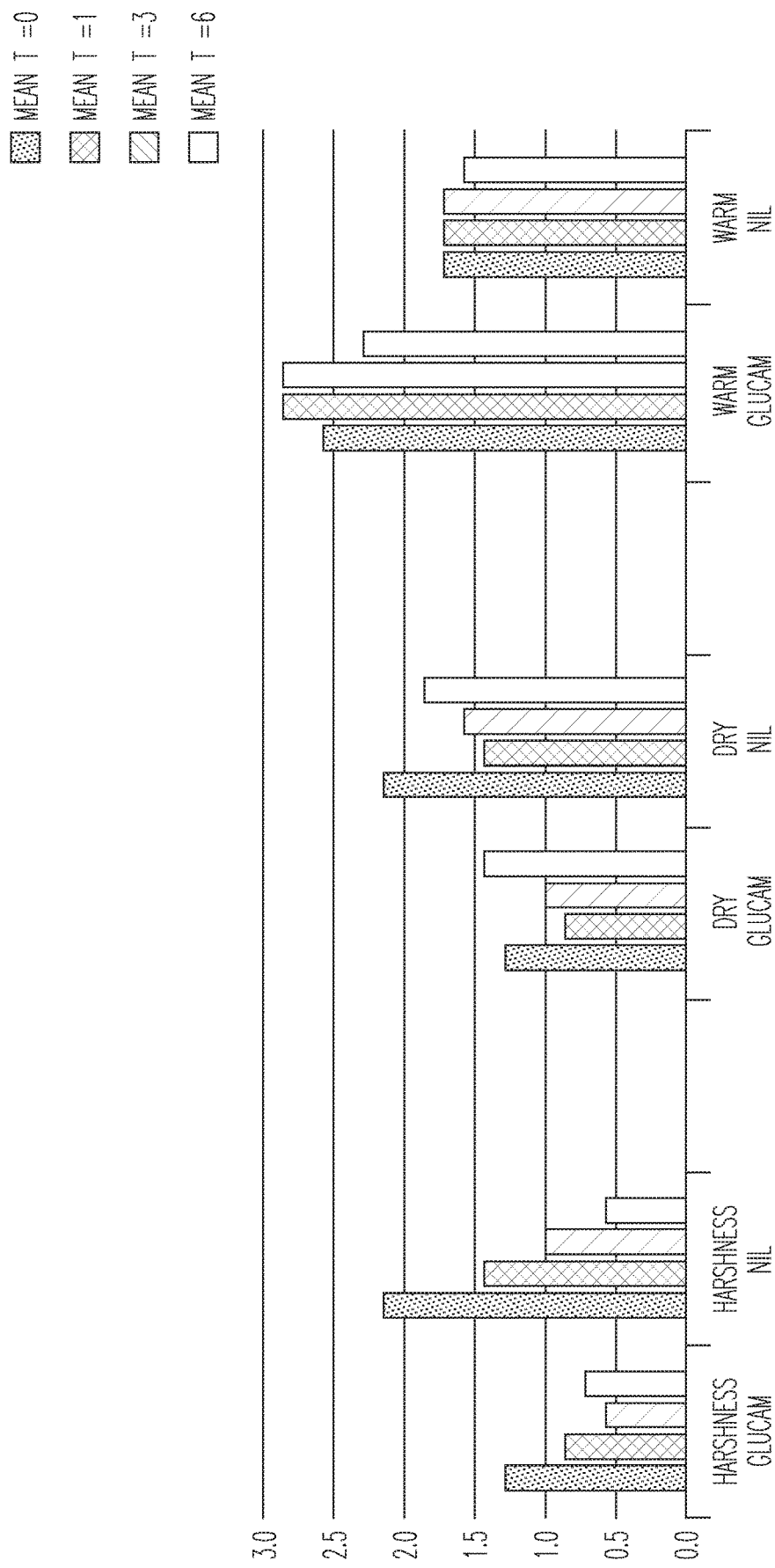
FIG. 8 shows a profile of fragrance materials in a fragrance construction according to the instant disclosure.

As shown in FIG. 8, the inclusion of Glucam P-20 in Fragrance Composition A4 including Oil Example 4 (denoted by "Glucam") reduces the perceived harshness of the fragrance initially and for up to 3 hours, as compared to the corresponding Fragrance Composition B4 including Oil Example 2 (denoted by "Nil Modulator") that is free of Glucam P-20 or any modulator. With the inclusion of Glucam P-20 the fragrance has a more pleasant warm scent whilst in the absence of the modulator is it a more unpleasant dry scent.

Example 6: Results from Test Method 2b

Figure 9:
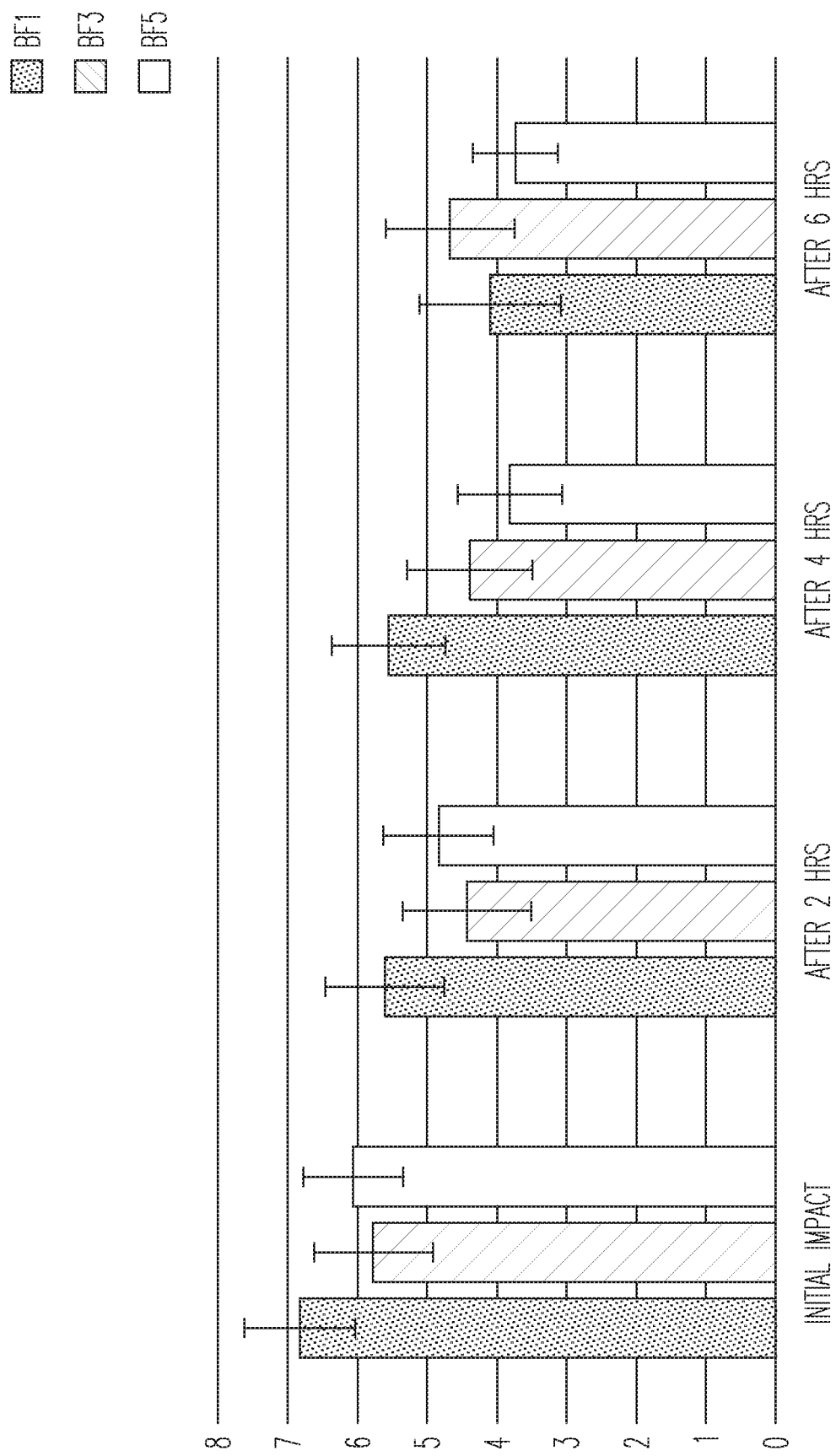
FIG. 9 shows a profile of a perceived harshness in a fragrance construction according to the instant disclosure.

FIG. 9 shows that harshness in Example A3, is significantly decreased over time using modulators other than Glucam compared to Example B3 without modulators. BF1 includes Oil Example 1 and no modulator; BF3 includes Oil Example 1 and ICA (isocetyl alcohol) as the modulator. BF5 includes Oil Example 1 and Kolliphor EL (propyl[{4-[2-(diethyl amino)-2-oxoethoxy]-3-methoxyphenyl}acetate) as the modulator. BF3 is significantly lower at 90% confidence than BF1 at 5 mins (p-value=0.083), 2 hours (p-value=0.073) and 4 hours (p-value=0.067) and BF5 is significantly lower at 95% confidence than BF1 at 4 hours (p-value=0.004).

Figure 10:
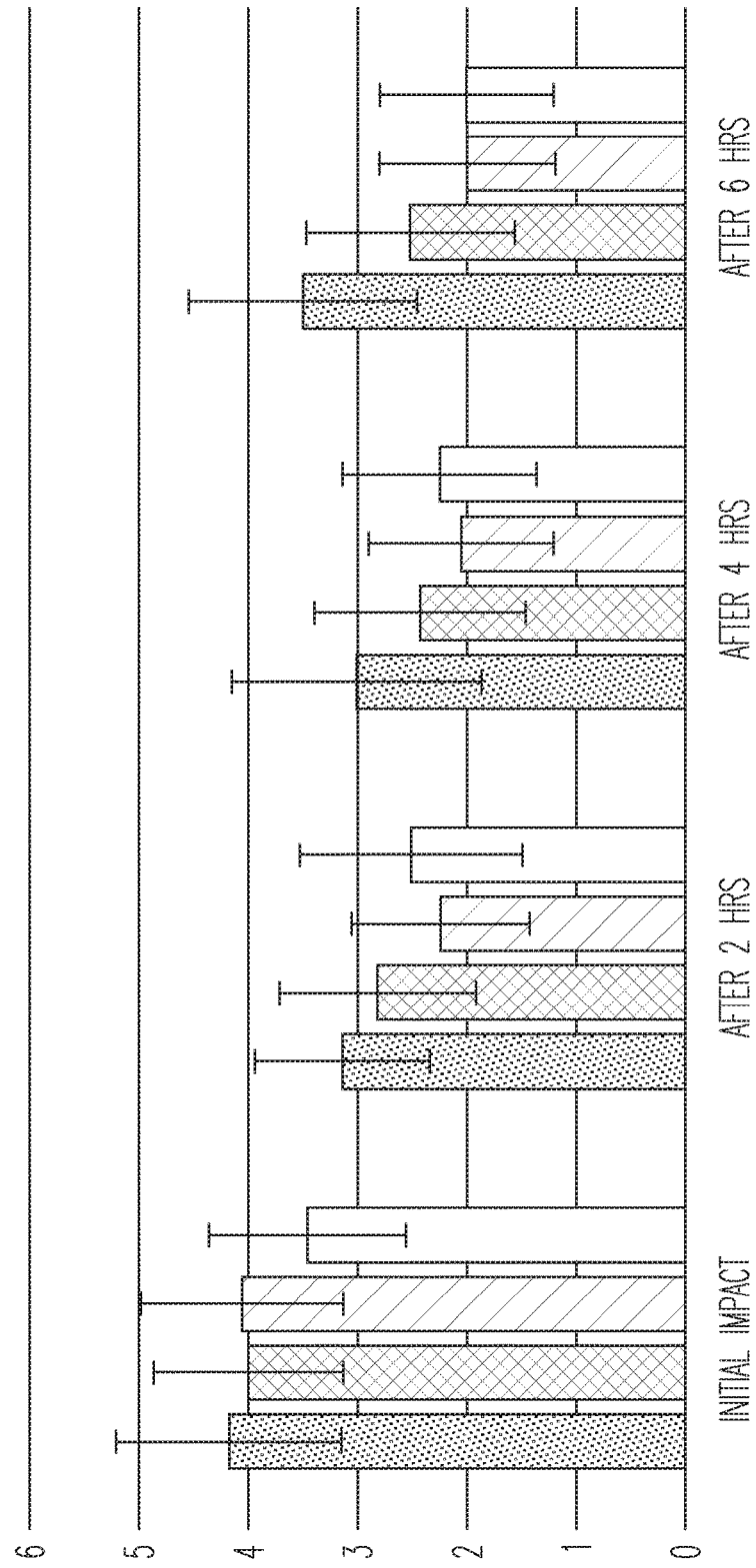
FIG. 10 shows a profile of a perceived harshness in a fragrance construction according to the instant disclosure.

FIG. 10 shows that harshness is reduced significantly in Example A3 by Kolliphor EL and Schercemol NGDO modulators with some reduction in harshness using ICA compared to Example B3 with no modulators. BH1 includes Oil Example 3 with no modulator. BH3 includes Oil Example 3 and isocetyl alcohol as the modulator. BH4 includes Oil Example 3 and Kolliphor EL (propyl[{4-[2-(diethyl amino)-2-oxoethoxy]-3-methoxyphenyl}acetate) as the modulator. BH5 includes Oil Example 3 and Schercemol NGDO (Neopentyl Glycol Diethylhexanoate) as the modulator. BH4 is significantly lower at 95% confidence than BH1 at 6 hours (p-value=0.030) and BH5 is significantly lower at 95% confidence than BH1 at 6 hours (p-value=0.033).

Additional Embodiments

The following exemplary embodiments are provided, the numbering of which is not to be construed as designating levels of importance:

Embodiment 1 provides a composition comprising:
a fragrance component present in an amount of from about 0.04 wt % to about 30 wt %, relative to the total weight of the composition, and wherein the fragrance component comprises:
at least one low volatile fragrance material having a vapor pressure less than 0.001 Torr (0.000133 kPa) at 25° C. present in an amount greater than 30 wt %, relative to the total weight of the fragrance component;
at least one moderate volatile fragrance material having a vapor pressure in the range of 0.1 Torr to 0.001 Torr (0.0133 kPa to 0.000133 kPa) at 25° C. present in an amount of from about 30 wt % to about 70 wt %, relative to the total weight of the fragrance component; and
at least one high volatile fragrance material having a vapor pressure greater than 0.1 Torr (0.0133 kPa) at 25° C. present in an amount of from about 0.1 wt % to about 30 wt % relative to the total weight of the fragrance component;
at least one substantially non-odorous fragrance modulator present in the amount of from about 0.1 wt % to about 20 wt %, relative to the total weight of the composition.

Embodiment 2 provides the composition of Embodiment 1, wherein the at least one low volatile fragrance material is present in an amount of from 31 wt % to about 60 wt % relative to the total weight of the fragrance material.

Embodiment 3 provides the composition of any one of Embodiments 1 or 2, wherein the at least one moderate volatile fragrance material is present in an amount of from about 35 wt % to about 60 wt % relative to the total weight of the fragrance material.

Embodiment 4 provides the composition of any one of Embodiments 1-3, wherein the at least one high volatile fragrance material is present in an amount of from about 1 wt % to about 30 wt % relative to the total weight of the fragrance material.

Embodiment 5 provides the composition of any one of Embodiments 1-4, wherein the high volatile fragrance material is chosen from any of the materials or combinations of materials listed in any one of Tables 3A and 3B.

Embodiment 6 provides the composition of any one of Embodiments 1-5, wherein the low volatile fragrance material is chosen from chosen from any of the materials or combinations of materials listed in any one of Tables 1A and 1B.

Embodiment 7 provides the composition of any one of Embodiments 1-6, wherein the at least one substantially non-odorous fragrance modulator is chosen from methyl glucoside polol, ethyl glucoside polyol, propyl glucoside polyol, or mixtures thereof.

Embodiment 8 provides the composition of any one of Embodiments 1-7, wherein the at least one substantially non-odorous fragrance modulator is chosen from polypropylene glycol-10 methyl glucose ether, ethoxylated methyl glucose ether, polypropylene glycol-20 methyl glucose ether, caprylyl, capryl glucoside, undecyl glucoside, and mixtures thereof.

Embodiment 9 provides the composition of any one of Embodiments 1-8, wherein the composition is substantially free of isocetyl alcohol, diisobutyl adipate, diisoamyl adipate, polypropylene glycol-3 myristyl ether, and neopentyl glycol diethyl hexanoate, neopentyl glycol diisononanoate, cetearyl ethyl hexanoate, and their mixtures, or a mixture thereof.

Embodiment 10. The composition of any one of Embodiments 1-9, wherein the at least one substantially non-odorous fragrance modulator is chosen from:

a compound of formula (I):

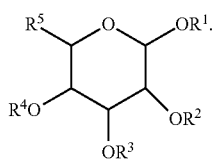

I wherein:
$R^1$ is hydrogen, alkyl, alkenyl or alkynyl;
$R^2$ is selected from hydrogen, $(C_2-C_{20})$alkyl, $(C_2-C_{20})$alkenyl, $(C_2-C_{20})$alkynyl, $—[R^6R^7(R^8)0]_wR^9$, wherein w is from 1 to 10, preferably 2 to 9;
$R^3$ is selected from hydrogen, alkyl, alkenyl, alkynyl, $—[R^6R\backslash R^8)0]yR^9$, wherein y is from 1 to 10 or 2 to 9;
$R^4$ is selected from hydrogen, alkyl, alkenyl, alkynyl, $—[R^6R\backslash R^8)0]xR^9$, wherein x is from 1 to 10, preferably 2 to 9;
$R^5$ is selected from hydrogen, alkyl, alkenyl, alkynyl, $—R^60 R^9$, $—R^60 [R^6R^7(R^8)0]zR^9$, wherein z is from 1 to 10, preferably 2 to 9;
each $R^6$ and $R^7$ are independently selected from $(C_2-C_{20})$alkylene, $(C_2-C_{20})$alkenylene, or $(C_2-C_{20})$alkynylene; and
each $R^8$ and $R^9$ is independently selected from hydrogen or alkyl, a compound of formula (II):

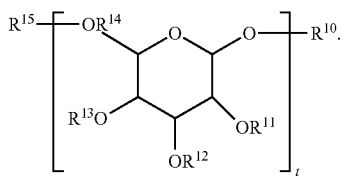

II wherein:
$R^{10}$ is hydrogen, $(C_2-C_{20})$alkyl, $(C_2-C_{20})$alkenyl or $(C_2-C_{20})$alkynyl;
each $R^{11}$ is independently selected from hydrogen, $(C_2-C_{20})$alkyl, $(C_2-C_{20})$alkenyl, $(C_2-C_{20})$alkynyl;
each $R^{12}$ is independently selected from hydrogen, $(C_2-C_{20})$alkyl, $(C_2-C_{20})$alkenyl, or $(C_2-C_{20})$alkynyl;
each $R^{13}$ is independently selected from hydrogen, $(C_2-C_{20})$alkyl, $(C_2-C_{20})$alkenyl, or $(C_2-C_{20})$alkynyl;

each $R^{14}$ is selected from $(C_2-C_{20})$alkylene, $(C_2-C_{20})$alkenylene, or $(C_2-C_{20})$alkynylene; and
$R^{15}$ is hydrogen, $(C_2-C_{20})$alkyl, $(C_2-C_{20})$alkenyl or $(C_2-C_{20})$ alkynyl; wherein tis 5 or less, preferably 1, 2 or 3;

Sucrose Laurate, Sucrose Dilaurate, Sucrose Myristate, Sucrose Palmitate, Sucrose Stearate, Sucrose Distearate, Sucrose Tristearate, and their mixtures;

Trimethylcyclohexane derivatives having the formula (III):

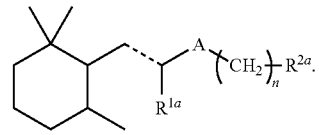

(III)

wherein:
n is 0, 1 or 2;
A is C=O or CH—OH;
$R^{1a}$ is hydrogen or methyl;
$R^{2a}$ is a $C_2-C_{10}$ hydrocarbon group; and
is a saturated or unsaturated carbon-carbon bond;

L-menthoxy ether derivatives having the formula (IV):

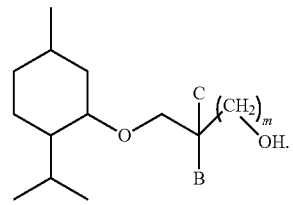

(IV)

wherein:
m is 0, 1 or 2;
B is hydrogen or OH;
and C is hydrogen or
methyl;

Tetra-hydronaphthalene derivatives having the formula (V):

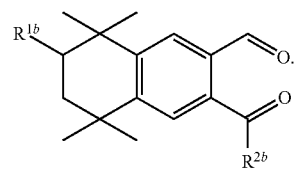

(V)

wherein:
$R^{1b}$ is hydrogen or methyl; and
$R^{2b}$ is alkyl;
140
Hyaluronic acid disaccharide sodium salt, sodium hyaluronate and their mixtures;

Ether derivatives having the formula (VI) or formula (VII):

$$C_5H_lO_m—(OR^{1c})$$ (VI).

wherein:
$C_5H_lO_m$ is a pentose residue, wherein l is an integer from 6 to 9, and m is an integer from 1 to 4;
n is an integer from 1 to 4; and
$R^{1c}$ is $C_4$-$C_{20}$ hydrocarbon group; and

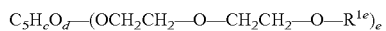  (VII).

wherein:
$C_6H_xO_y$ is a hexose residue, wherein x is an integer from 7 to 11, and y is
an integer from 1 to 5;
z is an integer from 1 to 5; and
$R^{1d}$ is $C_4$-$C_{20}$ hydrocarbon group; and
Diethylene Glycol Ether derivatives having the formula (VIII) or formula (IX):

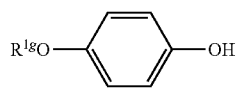 (VIII)

wherein:
$C_5H_cO_d$ is a pentose residue, wherein c is an integer from 6 to 8,
and d is an integer from 1 to 3;
e is an integer from 2 to 4;
and $R^{1e}$ is $C_1$-$C_6$ alkyl
group; and

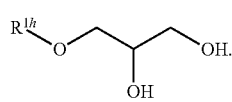 (IX)

wherein:
$C_6H_fO_g$ is a hexose residue, wherein f is an integer from 7 to 10, and g is an integer from 1 to 4;
h is an integer from 2 to 5;
and $R^{1f}$ is $C_1$-$C_6$ alkyl
group;
Hydroquinone Glycoside derivatives having the formula (X):

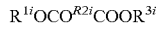 (X).

wherein:
$R^{1g}$ is selected from the group consisting of: (i) pentose residue, hexose residue, aminosaccharide residue, uronic acid residue and their mixtures; (ii) methylated versions of group (i); and (iii) mixtures of groups (i) and (ii); and Propylene Glycol Propyl Ether; Dicetyl Ether; Polyglycerin-4 Ethers; Isoceteth-5; Isoceteth-7, Isoceteth-10; Isoceteth-12; Isoceteth-15; Isoceteth-20; Isoceteth-25; Isoceteth-30; Disodium Lauroamphodipropionate; Hexaethylene glycol monododecyl ether; and their mixtures;
Glyceryl Ether derivatives having the formula (XI):

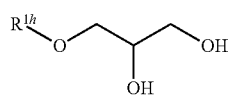 (XI)

wherein:
$R^{1h}$ is $C_4$-$C_{12}$ aliphatic hydrocarbon group;
Panthenol Ethyl Ether, DL-Panthenol and their mixtures;
Aliphatic Dibasic Acid Diester derivatives having the formula (XII):

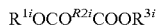 (XII).

wherein:
Rh is $C_4$-$C_5$ alkyl;
$R^{2i}$ is $C_4$ alkylene;
and $R^{3i}$ is $C_4$-$C_5$
alkyl; and
Aliphatic Ether derivatives having the formula (XIII):

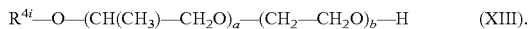 (XIII).

wherein:
a and b are integers such that the sum of a and b is from 1 to 4;
and $R^{4i}$ is an aliphatic chain comprising from 8 to 18 carbons; N-hexadecyl n-nonanoate, N-octadecyl n-nonanoate and their mixtures; Tricyclodecane Amide derivatives selected from the group consisting of:
the compounds of formula (XIV):

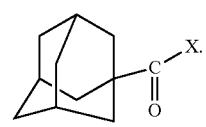 (XIV)

wherein:
X is selected from:

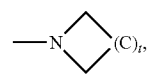 (Xa)

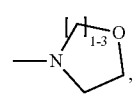 (Xb)

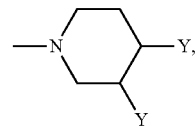 (Xc)

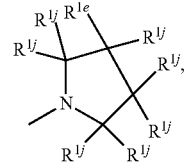 (Xd)

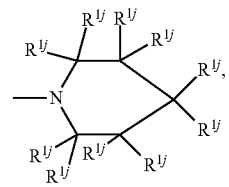 (Xe)

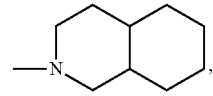 (Xf)

-continued (Xg)

(Xh)

or (Xi)

t is 1 to 8;
Y is hydrogen, or a halogen; and
each $R^{1j}$ is independently selected from a hydrogen, or $C_1$-$C_4$ alkyl; the compounds of formula (XV):

(XV)

wherein:
each $R^{2j}$ is independently selected from a hydrogen, methyl, ethyl or $C_3$-$C_{18}$
alkyl, cycloalkyl or cycloheteroalkyl, with the proviso that both $R^{2e}$ groups are not hydrogen; and
mixtures of the compounds of formulae (XII) and (XIII); and mixtures thereof.

Embodiment 11 provides the composition according to any one of Embodiments 1-10, in the form of a perfume, an eau de toilette, an eau de parfum, a cologne, a body splash, a lotion, a cream, a shampoo, a conditioner, a hair mist, a body oil, a deodorant, a solid fragrance, or a body spray.

Embodiment 12 provides a method of using the composition of any one of Embodiments 1-11, comprising contacting the fragrance component with at least one of skin, hair, and fabric.

Embodiment 13 provides the method of Embodiment 12, comprising contacting the fragrance with skin.

Embodiment 14 provides a method to enhance the fragrance profile of a composition or improve the longevity of an aroma, comprising bringing into contact or mixing at least one non-odorous fragrance modulator with at least one low volatile fragrance material, high volatile fragrance material, and moderate volatile fragrance material according to a composition of any one of Embodiments 1-13.

Embodiment 15 provides the fragrance component of any one of Embodiments 1-14, wherein the fragrance material is selected from a citrus-type note, green-type note, spicy-type note, cinnamon-type notes, pepper-type notes, cumin-type notes, ginger-type notes, juniper-type notes, fruity-type notes, peachy-type notes, lactonic-type notes, floral-type notes, woody-type notes, cedarwoood-type notes, sandalwood type notes, vetyver-type notes, suede-type notes, sappy-type notes, earthy-type notes, rooty-type notes, birch-type notes, leather-type note, smoky-type note, animalic-type notes, balsamic-type notes, musk-type notes, and mixtures thereof.

Embodiment 16 provides a method for producing a consumer product comprising bringing into contact or mixing into the product an organoleptically active quantity of a fragrance composition according to any one of Embodiments 1-15.

Embodiment 17 provides a perfuming consumer product or article comprising a fragrance composition according to any one of Embodiments 1-16 wherein the perfuming consumer product is chosen from a fabric care product, an air care product, a home care product, a beauty care product or a mixture thereof.

Embodiment 18 provides a method of modifying or enhancing the odor properties of a body surface, comprising contacting or treating the body surface with a composition according to any one of Embodiments 1-17.

Embodiment 19 provides the composition of any one of Embodiments 1-18, further comprising:
  a volatile solvent present in an amount of from about 50 wt % to about 80 wt %, relative to the total weight of the composition; and
  optionally water.

Embodiment 20 provides a composition comprising:
  a fragrance component present in an amount of from about 0.04 wt % to about 30 wt %, relative to the total weight of the composition, and wherein the fragrance component comprises:
    at least one low volatile fragrance material having a vapor pressure less than 0.001 Torr (0.000133 kPa) at 25° C. present in an amount greater than 30 wt %, relative to the total weight of the fragrance component, wherein the low volatile fragrance material is chosen from any of the materials or combinations of materials listed in any one of Tables 1A and 1B;
    at least one moderate volatile fragrance material having a vapor pressure in the range of 0.1 Torr to 0.001 Torr (0.0133 kPa to 0.000133 kPa) at 25° C. present in an amount of from about 30 wt % to about 70 wt %, relative to the total weight of the fragrance component; and
    at least one high volatile fragrance material having a vapor pressure greater than 0.1 Torr (0.0133 kPa) at 25° C. present in an amount of from about 0.1 wt % to about 30 wt % relative to the total weight of the fragrance component;
  at least one substantially non-odorous fragrance modulator present in the amount of from about 0.1 wt % to about 20 wt %, relative to the total weight of the composition.

Embodiment 21 provides the composition of Embodiment 20, wherein the at least one low volatile fragrance material is present in an amount of from 31 wt % to about 60 wt % relative to the total weight of the fragrance material.

Embodiment 22 provides the composition of any one of Embodiments 20 or 21, wherein the at least one moderate volatile fragrance material is present in an amount of from about 35 wt % to about 60 wt % relative to the total weight of the fragrance material.

Embodiment 23 provides the composition of any one of Embodiments 20-22, wherein the at least one high volatile fragrance material is present in an amount of from about 1 wt % to about 30 wt % relative to the total weight of the fragrance material.

Embodiment 24 provides the composition of any one of Embodiments 20-23, wherein the high volatile fragrance material is chosen from any of the materials or combinations of materials listed in any one of Tables 3A and 3B.

Embodiment 25 provides the composition of any one of Embodiments 20-24, wherein the at least one substantially non-odorous fragrance modulator is chosen from methyl glucoside polol, ethyl glucoside polyol, propyl glucoside polyol, or mixtures thereof.

Embodiment 26 provides the composition of any one of Embodiments 20-25, wherein the at least one substantially non-odorous fragrance modulator is chosen from polypropylene glycol-10 methyl glucose ether, ethoxylated methyl glucose ether, polypropylene glycol-20 methyl glucose ether, caprylyl, capryl glucoside, undecyl glucoside, and mixtures thereof.

Embodiment 27 provides the composition of any one of Embodiments 20-26, wherein the composition is substantially free of isocetyl alcohol, diisobutyl adipate, diisoamyl adipate, polypropylene glycol-3 myristyl ether, and neopentyl glycol diethyl hexanoate, neopentyl glycol diisononanoate, cetearyl ethyl hexanoate, and their mixtures, or a mixture thereof.

Embodiment 28 provides the composition of any one of Embodiments 20-27, wherein the at least one substantially non-odorous fragrance modulator is chosen from:

a compound of formula (I):

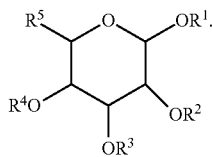

wherein:
$R^1$ is hydrogen, alkyl, alkenyl or alkynyl;
$R^2$ is selected from hydrogen, $(C_2-C_{20})$alkyl, $(C_2-C_{20})$alkenyl, $(C_2-C_{20})$alkynyl, $-[R^6R^7(R^8)O]_wR^9$, wherein w is from 1 to 10, preferably 2 to 9;
$R^3$ is selected from hydrogen, alkyl, alkenyl, alkynyl, $-[R^6R\backslash R^8)O]yR^9$, wherein y is from 1 to 10 or 2 to 9;
$R^4$ is selected from hydrogen, alkyl, alkenyl, alkynyl, $-[R^6R\backslash R^8)O]xR^9$, wherein x is from 1 to 10, preferably 2 to 9;
$R^5$ is selected from hydrogen, alkyl, alkenyl, alkynyl, $-R^6O R^9$, $-R^6O [R^6R^7(R^8)O]zR^9$, wherein z is from 1 to 10, preferably 2 to 9;
each $R^6$ and $R^7$ are independently selected from $(C_2-C_{20})$alkylene, $(C_2-C_{20})$alkenylene, or $(C_2-C_{20})$alkynylene; and
each $R^8$ and $R^9$ is independently selected from hydrogen or alkyl, a compound of formula (II):

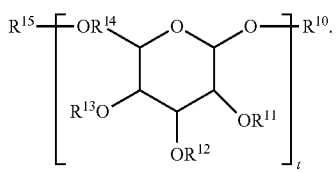

wherein:
$R^{10}$ is hydrogen, $(C_2-C_{20})$alkyl, $(C_2-C_{20})$alkenyl or $(C_2-C_{20})$alkynyl;
each $R^{11}$ is independently selected from hydrogen, $(C_2-C_{20})$alkyl, $(C_2-C_{20})$alkenyl, $(C_2-C_{20})$alkynyl;
each $R^{12}$ is independently selected from hydrogen, $(C_2-C_{20})$alkyl, $(C_2-C_{20})$alkenyl, or $(C_2-C_{20})$alkynyl;
each $R^{13}$ is independently selected from hydrogen, $(C_2-C_{20})$alkyl, $(C_2-C_{20})$alkenyl, or $(C_2-C_{20})$alkynyl;
each $R^{14}$ is selected from $(C_2-C_{20})$alkylene, $(C_2-C_{20})$alkenylene, or $(C_2-C_{20})$alkynylene; and
$R^{15}$ is hydrogen, $(C_2-C_{20})$alkyl, $(C_2-C_{20})$alkenyl or $(C_2-C_{20})$alkynyl; wherein t is 5 or less, preferably 1, 2 or 3;

Sucrose Laurate, Sucrose Dilaurate, Sucrose Myristate, Sucrose Palmitate, Sucrose Stearate, Sucrose Distearate, Sucrose Tristearate, and their mixtures;

Trimethylcyclohexane derivatives having the formula (III):

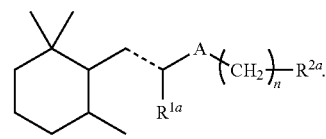

wherein:
n is 0, 1 or 2;
A is C=O or CH—OH;
$R^{1a}$ is hydrogen or methyl;
$R^{2a}$ is a $C_2-C_{10}$ hydrocarbon group; and
is a saturated or unsaturated carbon-carbon bond;

L-menthoxy ether derivatives having the formula (IV):

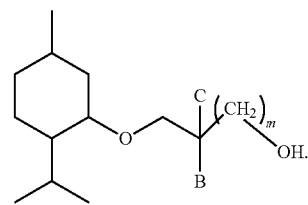

wherein:
m is 0, 1 or 2;
B is hydrogen or OH;
and C is hydrogen or methyl;

Tetra-hydronaphthalene derivatives having the formula (V):

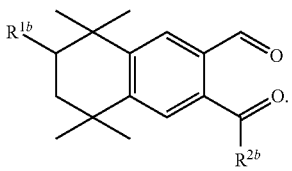

wherein:
$R^{1b}$ is hydrogen or methyl; and
$R^{2b}$ is alkyl;

Hyaluronic acid disaccharide sodium salt, sodium hyaluronate and their mixtures;

Ether derivatives having the formula (VI) or formula (VII):

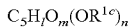 (VI).

wherein:

$C_5H_lO_m$ is a pentose residue, wherein l is an integer from 6 to 9, and m is
an integer from 1 to 4;
n is an integer from 1 to 4; and
$R^{1c}$ is $C_4$-$C_{20}$ hydrocarbon group; and

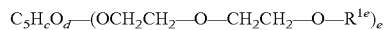 (VII)

wherein:

$C_6H_xO_y$ is a hexose residue, wherein x is an integer from 7 to 11, and y is an integer from 1 to 5;
z is an integer from 1 to 5; and
$R^{1d}$ is $C_4$-$C_{20}$ hydrocarbon group; and Diethylene Glycol Ether derivatives having the formula (VIII) or formula (IX):

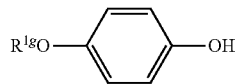 (VIII)

wherein:

$C_5H_cO_d$ is a pentose residue, wherein c is an integer from 6 to 8,
and d is an integer from 1 to 3;
e is an integer from 2 to 4;
and $R^{1e}$ is $C_1$-$C_6$ alkyl
group; and

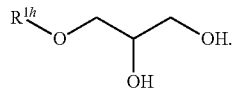 (IX)

wherein:

$C_6H_fO_g$ is a hexose residue, wherein f is an integer from 7 to 10, and g is an integer from 1 to 4;
h is an integer from 2 to 5;
and $R^1$ is $C_1$-$C_6$ alkyl
group;

Hydroquinone Glycoside derivatives having the formula (X):

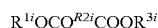 (X).

wherein:

$R^{1g}$ is selected from the group consisting of: (i) pentose residue, hexose residue, aminosaccharide residue, uronic acid residue and their mixtures; (ii) methylated versions of group (i); and (iii) mixtures of groups (i) and (ii); and Propylene Glycol Propyl Ether; Dicetyl Ether; Polyglycerin-4 Ethers; Isoceteth-5; Isoceteth-7; Isoceteth-10; Isoceteth-12; Isoceteth-15; Isoceteth-20; Isoceteth-25; Isoceteth-30; Disodium Lauroamphodipropionate; Hexaethylene glycol monododecyl ether; and their mixtures;

Glyceryl Ether derivatives having the formula (XI):

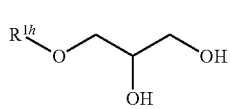 (XI)

wherein:

$R^{1h}$ is $C_4$-$C_{12}$ aliphatic hydrocarbon group;
Panthenol Ethyl Ether, DL-Panthenol and their mixtures;
Aliphatic Dibasic Acid Diester derivatives having the formula (XII):

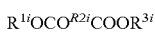 (XII).

wherein:

$R^{1i}$ is $C_4$-$C_5$ alkyl;
$R^{2i}$ is $C_4$ alkylene;
and $R^{3i}$ is $C_4$-$C_5$
alkyl; and Aliphatic Ether derivatives having the formula (XIII):

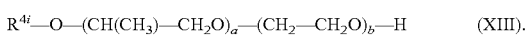 (XIII).

wherein:

a and b are integers such that the sum of a and b is from 1 to 4;
and $R^{4i}$ is an aliphatic chain comprising from 8 to 18 carbons; N-hexadecyl n-nonanoate, N-octadecyl n-nonanoate and their mixtures; Tricyclodecane Amide derivatives selected from the group consisting of:
the compounds of formula (XIV):

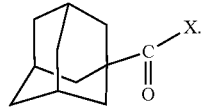 (XIV)

wherein:
X is selected from:

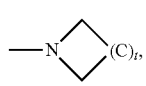 (Xa)

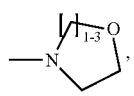 (Xb)

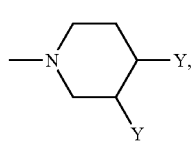 (Xc)

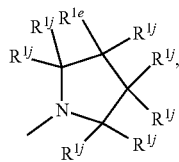 (Xd)

-continued

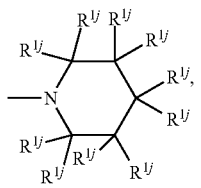
(Xe)

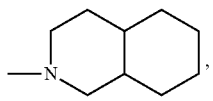
(Xf)

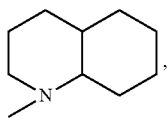
(Xg)

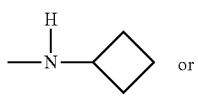
(Xh)

or

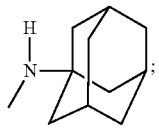
(Xi)

t is 1 to 8;
Y is hydrogen, or a halogen; and
each $R^{1j}$ is independently selected from a hydrogen, or $C_1$-$C_4$ alkyl; the compounds of formula (XV):

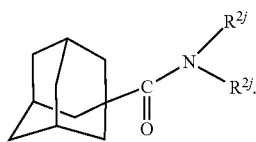
(XV)

wherein:
each $R^{2j}$ is independently selected from a hydrogen, methyl, ethyl or $C_3$-$C_{18}$ alkyl, cycloalkyl or cycloheteroalkyl, with the proviso that both $R^{2e}$ groups are not hydrogen; and
mixtures of the compounds of formulae (XII) and (XIII); and
mixtures thereof.

Embodiment 29 provides the composition according to any one of Embodiments 20-28, in the form of a perfume, an eau de toilette, an eau de parfum, a cologne, a body splash, a lotion, a cream, a shampoo, a conditioner, a hair mist, a body oil, a deodorant, a solid fragrance, or a body spray.

Embodiment 30 provides a method of using the composition of any one of Embodiments 20-29, comprising contacting the fragrance component with at least one of skin, hair, and fabric.

Embodiment 31 provides a method to enhance the fragrance profile of a composition or improve the longevity of an aroma, comprising bringing into contact or mixing at least one non-odorous fragrance modulator with at least one low volatile fragrance material, high volatile fragrance material, and moderate volatile fragrance material according to a composition of any one of Embodiments 20-30.

Embodiment 32 provides the fragrance component of any one of Embodiments 20-31, wherein the fragrance material is selected from a citrus-type note, green-type note, spicy-type note, cinnamon-type notes, pepper-type notes, cumin-type notes, ginger-type notes, floral-type notes, woody-type notes, cedarwoood-type notes, sandalwood type notes, vetyver-type notes, leather-type note, smoky-type note, musk-type notes, and mixtures thereof.

Embodiment 33 provides a perfuming consumer product or article comprising a fragrance composition according to any one of Embodiments 20-32 wherein the perfuming consumer product is chosen from a fabric care product, an air care product, a home care product, a beauty care product or a mixture thereof. Embodiment 34 provides a method for producing a consumer product comprising bringing into contact or mixing into the product an organoleptically active quantity of a fragrance composition according to any one of Embodiments 20-33.

Embodiment 35 provides a composition comprising:
a fragrance component present in an amount of from about 0.04 wt % to about 30 wt %, relative to the total weight of the composition, and wherein the fragrance component comprises:
at least one low volatile fragrance material having a vapor pressure less than 0.001 Torr (0.000133 kPa) at 25° C. present in an amount greater than 30 wt %, relative to the total weight of the fragrance component;
at least one moderate volatile fragrance material having a vapor pressure in the range of 0.1 Torr to 0.001 Torr (0.0133 kPa to 0.000133 kPa) at 25° C. present in an amount of from about 30 wt % to about 70 wt %, relative to the total weight of the fragrance component; and
at least one high volatile fragrance material having a vapor pressure greater than 0.1 Torr (0.0133 kPa) at 25° C. present in an amount of from about 0.1 wt % to about 30 wt % relative to the total weight of the fragrance component; and
at least one substantially non-odorous fragrance modulator is chosen from polypropylene glycol-10 methyl glucose ether, ethoxylated methyl glucose ether, and polypropylene glycol-20 methyl glucose ether, present in the amount of from about 0.1 wt % to about 20 wt %, relative to the total weight of the composition.

Embodiment 36 provides the composition of Embodiment 35, wherein the at least one low volatile fragrance material is present in an amount of from 31 wt % to about 60 wt % relative to the total weight of the fragrance material.

Embodiment 37 provides the composition of any one of Embodiments 35 or 36, wherein the at least one moderate volatile fragrance material is present in an amount of from about 35 wt % to about 60 wt % relative to the total weight of the fragrance material.

Embodiment 38 provides the composition of any one of Embodiments 35-37, wherein the at least one high volatile fragrance material is present in an amount of from about 1 wt % to about 30 wt % relative to the total weight of the fragrance material.

Embodiment 39 provides the composition of any one of Embodiments 35-38, wherein the high volatile fragrance material is chosen from any of the materials or combinations of materials listed in any one of Tables 3A and 3B.

Embodiment 40 provides the composition of any one of Embodiments 35-39, wherein the low volatile fragrance material is chosen from any of the materials or combinations of materials listed in any one of Tables 1A and 1B.

Embodiment 41 provides the composition of any one of Embodiments 35-40, wherein the composition is substantially free of isocetyl alcohol, diisobutyl adipate, diisoamyl adipate, polypropylene glycol-3 myristyl ether, and neopentyl glycol diethyl hexanoate, neopentyl glycol diisononanoate, cetearyl ethyl hexanoate, and their mixtures, or a mixture thereof.

Embodiment 42 provides the composition according to any one of Embodiments 35-41, in the form of a perfume, an eau de toilette, an eau de parfum, a cologne, a body splash, a lotion, a cream, a shampoo, a conditioner, a hair mist, a body oil, a deodorant, a solid fragrance, or a body spray.

Embodiment 43 provides a method to enhance the fragrance profile of a composition or improve the longevity of an aroma, comprising bringing into contact or mixing at least one non-odorous fragrance modulator with at least one low volatile fragrance material, high volatile fragrance material, and moderate volatile fragrance material according to a composition of any one of Embodiments 35-42.

Embodiment 44 provides the fragrance component of any one of Embodiments 35-43, wherein the fragrance material is selected from a citrus-type note, green-type note, spicy-type note, cinnamon-type notes, pepper-type notes, cumin-type notes, ginger-type notes, floral-type notes, woody-type notes, cedarwoood-type notes, sandalwood type notes, vetyver-type notes, leather-type note, smoky-type note, musk-type notes, and mixtures thereof.

Embodiment 45 provides a method for producing a consumer product comprising bringing into contact or mixing into the product an organoleptically active quantity of a fragrance composition according to any one of Embodiments 35-44.

Embodiment 46 provides a perfuming consumer product or article comprising a fragrance composition according to any one of Embodiments 35-45, wherein the perfuming consumer product is chosen from a fabric care product, an air care product, a home care product, a beauty care product, or a mixture thereof.

Embodiment 47 provides a method of modifying or enhancing the odor properties of a body surface, comprising contacting or treating the body surface with a composition according to any one of Embodiments 35-46.

Embodiment 48 provides the composition of any one of Embodiments 35-47, further comprising:
a volatile solvent present in an amount of from about 50 wt % % to about 80 wt %, relative to the total weight of the composition; and
optionally water.

Embodiment 49 provides a composition comprising:
a fragrance component present in an amount of from about 0.04 wt % to about 30 wt %, relative to the total weight of the composition, and wherein the fragrance component comprises:
  at least one low volatile fragrance material having a vapor pressure less than 0.001 Torr (0.000133 kPa) at 25° C. present in an amount greater than 30 wt %, relative to the total weight of the fragrance component;
  at least one moderate volatile fragrance material having a vapor pressure in the range of 0.1 Torr to 0.001 Torr (0.0133 kPa to 0.000133 kPa) at 25° C. present in an amount of from about 30 wt % to about 70 wt %, relative to the total weight of the fragrance component; and
  at least one high volatile fragrance material having a vapor pressure greater than 0.1 Torr (0.0133 kPa) at 25° C. present in an amount of from about 0.1 wt % to about 30 wt % relative to the total weight of the fragrance component; and
at least one substantially non-odorous fragrance modulator present in the amount of from about 0.1 wt % to about 20 wt %, relative to the total weight of the composition;
wherein at least one of the low volatile fragrance material, the moderate volatile fragrance material, and the high volatile fragrance material is present in the fragrance component for a period of time that is longer than a corresponding fragrance component that is free of the substantially non-odorous fragrance modulator.

Embodiment 50 provides the composition of Embodiment 49, wherein the at least one high volatile fragrance material is present in an amount of from about 1 wt % to about 30 wt % relative to the total weight of the fragrance material.

Embodiment 51 provides the composition of any one of Embodiments 49 or 50, wherein the at least one moderate volatile fragrance material is present in an amount of from about 35 wt % to about 60 wt % relative to the total weight of the fragrance material.

Embodiment 52 provides the composition of any one of Embodiments 49-51, wherein the at least one low volatile fragrance material is present in an amount of from about 31 wt % to about 60 wt % relative to the total weight of the fragrance material.

Embodiment 53 provides the composition of any one of Embodiments 49-52, wherein the high volatile fragrance material is chosen from any of the materials or combinations of materials listed in any one of Tables 3A and 3B.

Embodiment 54 provides the composition of any one of Embodiments 49-53, wherein the low volatile fragrance material is chosen from any of the materials or combinations of materials listed in any one of Tables 1A and 1B.

Embodiment 55 provides the composition of any one of Embodiments 49-54, wherein the at least one substantially non-odorous fragrance modulator is chosen from methyl glucoside polol, ethyl glucoside polyol, propyl glucoside polyol, or mixtures thereof.

Embodiment 56 provides the composition of any one of Embodiments 49-55, wherein the at least one substantially non-odorous fragrance modulator is chosen from polypropylene glycol-10 methyl glucose ether, ethoxylated methyl glucose ether, polypropylene glycol-20 methyl glucose ether, caprylyl, capryl glucoside, undecyl glucoside, and mixtures thereof.

Embodiment 57 provides the composition of any one of Embodiments 49-56, wherein the composition is substantially
free of isocetyl alcohol, diisobutyl adipate, diisoamyl adipate, polypropylene glycol-3 myristyl ether, and neopentyl glycol diethylhexanoate, polypropylene glycol-3 myristyl ether, neopentyl glycol diethylhexanoate, neopentyl glycol diisononanoate, cetearyl ethyl hexanoate, and their mixtures, or a mixture thereof.

Embodiment 58 provides the composition of any one of Embodiments 49-57, wherein the at least one substantially non-odorous fragrance modulator is chosen from:
a compound of formula (I):

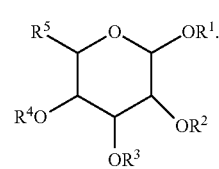

I wherein:
R¹ is hydrogen, alkyl, alkenyl or alkynyl;
R² is selected from hydrogen, $(C_2-C_{20})$alkyl, $(C_2-C_{20})$alkenyl, $(C_2-C_{20})$alkynyl, $—[R^6R^7(R^8)0]_wR^9$, wherein w is from 1 to 10, preferably 2 to 9;
R³ is selected from hydrogen, alkyl, alkenyl, alkynyl, $—[R^6R\backslash R^8)0]yR^9$, wherein y is from 1 to 10 or 2 to 9;
R⁴ is selected from hydrogen, alkyl, alkenyl, alkynyl, $—[R^6R\backslash R^8)0]xR^9$, wherein x is from 1 to 10, preferably 2 to 9;
R⁵ is selected from hydrogen, alkyl, alkenyl, alkynyl, $—R^60 R^9$, $—R^60 [R^6R^7(R^8)0]zR^9$,
wherein z is from 1 to 10, preferably 2 to 9;
each R⁶ and R⁷ are independently selected from $(C_2-C_2)$alkylene, $(C_2-C_{20})$alkenylene, or $(C_2-C_{20})$alkynylene; and
each R⁸ and R⁹ is independently selected from hydrogen or alkyl, a compound of formula (II):

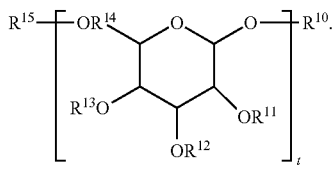

wherein:
R¹⁰ is hydrogen, $(C_2-C_{20})$alkyl, $(C_2-C_{20})$alkenyl or $(C_2-C_{20})$alkynyl;
each R¹¹ is independently selected from hydrogen, $(C_2-C_{20})$alkyl, $(C_2-C_{20})$alkenyl, $(C_2-C_{20})$alkynyl;
each R¹² is independently selected from hydrogen, $(C_2-C_{20})$alkyl, $(C_2-C_{20})$alkenyl, or $(C_2-C_{20})$alkynyl;
each R¹³ is independently selected from hydrogen, $(C_2-C_{20})$alkyl, $(C_2-C_{20})$alkenyl, or $(C_2-C_{20})$alkynyl;
each R¹⁴ is selected from $(C_2-C_{20})$alkylene, $(C_2-C_{20})$alkenylene, or $(C_2-C_{20})$alkynylene; and
R¹⁵ is hydrogen, $(C_2-C_{20})$alkyl, $(C_2-C_{20})$alkenyl or $(C_2-C_{20})$alkynyl; wherein t is 5 or less, preferably 1, 2 or 3;
Sucrose Laurate, Sucrose Dilaurate, Sucrose Myristate, Sucrose Palmitate, Sucrose Stearate, Sucrose Distearate, Sucrose Tristearate, and their mixtures;
Trimethylcyclohexane derivatives having the formula (III):

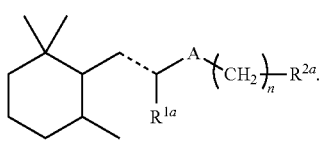

wherein:
n is 0, 1 or 2;
A is C=O or CH—OH;
R¹ᵃ is hydrogen or methyl;
R²ᵃ is a $C_2-C_{10}$ hydrocarbon group; and
is a saturated or unsaturated carbon-carbon bond;

L-menthoxy ether derivatives having the formula (IV):

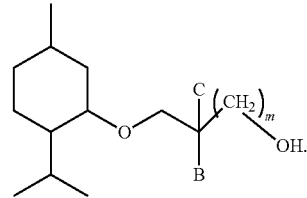

wherein:
m is 0, 1 or 2;
B is hydrogen or OH;
and C is hydrogen or methyl;
Tetra-hydronaphthalene derivatives having the formula (V):

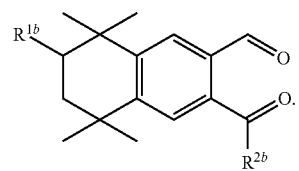

wherein:
Rib is hydrogen or methyl; and
R²ᵇ is alkyl;
140
Hyaluronic acid disaccharide sodium salt, sodium hyaluronate and their mixtures;
Ether derivatives having the formula (VI) or formula (VII):

$$C_5H_lO_m—(OR^{1c})_n \quad (VI).$$

wherein:
$C_5H_lO_m$ is a pentose residue, wherein l is an integer from 6 to 9, and m is an integer from 1 to 4;
n is an integer from 1 to 4; and
$R^{1c}$ is $C_4-C_{20}$ hydrocarbon group; and

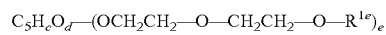
$$C_5H_cO_d—(OCH_2CH_2—O—CH_2CH_2—O—R^{1e})_e \quad (VII).$$

wherein:
$C_6H_xO_y$ is a hexose residue, wherein x is an integer from 7 to 11, and y is an integer from 1 to 5;
z is an integer from 1 to 5; and
$R^{1d}$ is $C_4-C_{20}$ hydrocarbon group; and
Diethylene Glycol Ether derivatives having the formula (VIII) or formula (IX):

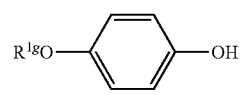

wherein:
$C_5H_cO_d$ is a pentose residue, wherein c is an integer from 6 to 8, and d is an integer from 1 to 3;
e is an integer from 2 to 4:
and $R^{1e}$ is $C_1$-$C_6$ alkyl
group; and (IX)

wherein:
$C_6H_fO_g$ is a hexose residue, wherein f is an integer from 7 to 10, and g is an integer from 1 to 4:
h is an integer from 2 to 5;
and $R^{1f}$ is $C_1$-$C_6$ alkyl
group;
Hydroquinone Glycoside derivatives having the formula (X):

$R^{1i}OCO^{R2i}COOR^{3i}$ (X).

wherein:
$R^{1g}$ is selected from the group consisting of: (i) pentose residue, hexose residue, aminosaccharide residue, uronic acid residue and their mixtures; (ii) methylated versions of group (i); and (iii) mixtures of groups (i) and (ii); and Propylene Glycol Propyl Ether; Dicetyl Ether; Polyglycerin-4 Ethers; Isoceteth-5: Isoceteth-7, Isoceteth-10: Isoceteth-12; Isoceteth-15; Isoceteth-20; Isoceteth-25; Isoceteth-30; Disodium Lauroamphodipropionate; Hexaethylene glycol monododecyl ether; and their mixtures;
Glyceryl Ether derivatives having the formula (XI):

(XI)

wherein:
$R^{1h}$ is $C_4$-$C_{12}$ aliphatic hydrocarbon group;
Panthenol Ethyl Ether, DL-Panthenol and their mixtures;
Aliphatic Dibasic Acid Diester derivatives having the formula (XII):

$R^{1i}OCO^{R2i}COOR^{3i}$ (XII).

wherein:
$R^1$ is $C_4$-$C_5$ alkyl;
$R^{2i}$ is $C_4$ alkylene;
and $R^{3i}$ is $C_4$-$C_5$
alkyl; and
Aliphatic Ether derivatives having the formula (XIII):

$R^{4i}$—O—$(CH(CH_3)$—$CH_2O)_a$—$(CH_2$—$CH_2O)_b$—H (XIII).

wherein:
a and b are integers such that the sum of a and b is from 1 to 4;
and $R^{4i}$ is an aliphatic chain comprising from 8 to 18 carbons; N-hexadecyl n-nonanoate, Noctadecyl n-nonanoate and their mixtures; Tricyclodecane Amide derivatives selected from the group consisting of:

the compounds of formula (XIV):

(XIV)

wherein:
X is selected from:

(Xa)

(Xb)

(Xc)

(Xd)

(Xe)

(Xf)

(Xg)

(Xh)

(Xi)

t is 1 to 8;
Y is hydrogen, or a halogen; and
each $R^{1i}$ is independently selected from a hydrogen, or $C_1$-$C_4$ alkyl; the compounds of formula (XV):

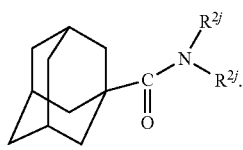

(XV)

wherein:

each $R^{2j}$ is independently selected from a hydrogen, methyl, ethyl or $C_3$-$C_{18}$ alkyl, cycloalkyl or cycloheteroalkyl, with the proviso that both $R^{2e}$ groups are not hydrogen; and mixtures of the compounds of formulae (XII) and (XIII); and mixtures thereof.

Embodiment 59 provides the composition according to any one of Embodiments 49-58, in the form of a perfume, an eau de toilette, an eau de parfum, a cologne, a body splash, a lotion, a cream, a shampoo, a conditioner, a hair mist, a body oil, a deodorant, a solid fragrance, or a body spray.

Embodiment 60 provides a method of using the composition of any one of Embodiments 49-59, comprising contacting the fragrance component with at least one of skin, hair, and fabric.

Embodiment 61 provides a method to enhance the fragrance profile of a composition or improve the longevity of an aroma, comprising bringing into contact or mixing at least one non-odorous fragrance modulator with at least one low volatile fragrance material, high volatile fragrance material, and moderate volatile fragrance material according to a composition of any one of Embodiments 49-60.

Embodiment 62 provides the fragrance component of any one of Embodiments 49-61, wherein the fragrance material is selected from a citrus-type note, green-type note, spicy-type note, cinnamon-type notes, pepper-type notes, cumin-type notes, ginger-type notes, floral-type notes, woody-type notes, cedarwoood-type notes, sandalwood type notes, vetyver-type notes, leather-type note, smoky-type note, musk-type notes, and mixtures thereof.

Embodiment 63 provides a method for producing a consumer product comprising bringing into contact or mixing into the product an organoleptically active quantity of a fragrance composition according to any one of Embodiments 49-62.

Embodiment 64 provides a perfuming consumer product or article comprising a fragrance composition according to any one of Embodiments 49-63 wherein the perfuming consumer product is chosen from a fabric care product, an air care product, a home care product, a beauty care product, or a mixture thereof.

Embodiment 65 provides a method of modifying or enhancing the odor properties of a body surface, comprising contacting or treating the body surface with a composition according to any one of Embodiments 49-64.

Embodiment 66 provides the composition of any one of Embodiments 49-65, further comprising: a volatile solvent present in an amount of from about 50 wt % to about 80 wt %, relative to the total weight of the composition; and optionally water.

What is claimed is:

1. A composition comprising:
   a fragrance component present in an amount of from about 0.04 wt % to about 30 wt %, relative to the total weight of the composition, and wherein the fragrance component comprises:
   at least one low volatile fragrance material having a vapor pressure less than 0.001 Torr (0.000133 kPa) at 25° C. comprising a mixture of (5E)-3-methylcyclopentadec-5-en-1-one, 1-(2,2,6-Trimethylcyclohexyl)-hexan-3-ol, cis-3-hexenyl salicylate, and evernyl present in an amount greater than 35 wt %, relative to the total weight of the fragrance component, such that the low volatile fragrance material is overdosed;
   at least one moderate volatile fragrance material having a vapor pressure in the range of 0.1 Torr to 0.001 Torr (0.0133 kPa to 0.000133 kPa) at 25° C. comprising a mixture of ambroxide, 1,1,2,3,3-pentamethyl-2,5,6,7-tetrahydroinden-4-one, and ethoxymethoxycyclododecane present in an amount of from about 30 wt % to about 65 wt %, relative to the total weight of the fragrance component; and
   at least one high volatile fragrance material having a vapor pressure greater than 0.1 Torr (0.0133 kPa) at 25° C. comprising a mixture of ethyl butyrate, 2,4-Dimethyl-3-cyclohexenecarboxaldehyde, beta gamma hexenol, cis-3-hexenyl acetate, and (2-tert-butylcyclohexyl) acetate present in an amount of from about 0.1 wt % to about 30 wt % relative to the total weight of the fragrance component;
   at least one substantially non-odorous fragrance modulator comprising polypropylene glycol-20 methyl glucose ether present in the amount of from about 0.1 wt % to about 20 wt %, relative to the total weight of the composition.

2. The composition of claim 1, wherein the at least one low volatile fragrance material is present in an amount of from 40 wt % to about 60 wt % relative to the total weight of the fragrance material.

3. The composition of claim 1, wherein the at least one moderate volatile fragrance material is present in an amount of from about 35 wt % to about 60 wt % relative to the total weight of the fragrance material.

4. The composition of claim 1, wherein the at least one high volatile fragrance material is present in an amount of from about 1 wt % to about 30 wt % relative to the total weight of the fragrance material.

5. The composition of claim 1, in the form of a perfume, an eau de toilette, an eau de parfum, a cologne, a body splash, a lotion, a cream, a shampoo, a conditioner, a hair mist, a body oil, a deodorant, a solid fragrance, or a body spray.

6. A method for producing a consumer product comprising bringing into contact or mixing into the product an organoleptically active quantity of a composition of claim 1.

* * * * *